(12) United States Patent
Belyaev et al.

(10) Patent No.: US 9,291,627 B2
(45) Date of Patent: Mar. 22, 2016

(54) ANALYTE DETECTION ASSAYS

(75) Inventors: Alexander Belyaev, San Diego, CA (US); Craig Monell, La Jolla, CA (US); Joseph Sorge, Wilson, WY (US)

(73) Assignee: Agilent Technologies Inc., Santa Clara, CA (US)

( * ) Notice: Subject to any disclaimer, the term of this patent is extended or adjusted under 35 U.S.C. 154(b) by 1523 days.

(21) Appl. No.: 12/375,570

(22) PCT Filed: Jul. 14, 2008

(86) PCT No.: PCT/US2008/069975
§ 371 (c)(1),
(2), (4) Date: Jan. 29, 2009

(87) PCT Pub. No.: WO2009/012220
PCT Pub. Date: Jan. 22, 2009

(65) Prior Publication Data
US 2010/0075307 A1    Mar. 25, 2010

Related U.S. Application Data

(63) Continuation-in-part of application No. 11/897,892, filed on Aug. 31, 2007, now Pat. No. 7,659,069.

(60) Provisional application No. 60/959,908, filed on Jul. 17, 2007.

(51) Int. Cl.
*C12Q 1/68* (2006.01)
*G01N 33/58* (2006.01)
*G01N 33/543* (2006.01)

(52) U.S. Cl.
CPC .............. *G01N 33/58* (2013.01); *C12Q 1/6804* (2013.01); *C12Q 1/6853* (2013.01); *G01N 33/543* (2013.01)

(58) Field of Classification Search
None
See application file for complete search history.

(56) References Cited

U.S. PATENT DOCUMENTS 5,665,539 A    9/1997  Sano et al.
5,985,548 A   11/1999  Collier et al.
(Continued)

FOREIGN PATENT DOCUMENTS

WO    WO2006037064    4/2006
WO    WO2006074217    7/2006

OTHER PUBLICATIONS

Gullberg et al. (PNAS, 2004, vol. 101, No. 22, p. 8420-8424).*
(Continued)

*Primary Examiner* — Stephanie K Mummert

(57) ABSTRACT

The present invention provides methods, kits and compositions for the detection of an analyte. In the methods of the invention, a binding molecule coupled to a first polymerase is incubated with a modified polynucleotide template to form a copy of the modified polynucleotide template without any modified nucleotides. The unmodified copy is detected in a second amplification/primer extension reaction using a second polymerase that is unable to amplify the modified polynucleotide template. Detection of the unmodified copy is indicative of the presence and/or amount of the analyte in the sample. In place of the binding molecule coupled to a first polymerase, a pair of analyte-specific probes can also be used. The first analyte specific probe comprises a first binding moiety and a first portion of a first polymerase and the second analyte specific probe comprises a second binding moiety and a second portion of the first polymerase. When the binding moieties are bound to the analyte the first and second portions of the polymerase interact to form a functional polymerase complex that is used to form a copy of the modified polynucleotide template without any modified nucleotides.

16 Claims, 15 Drawing Sheets

(56) References Cited

U.S. PATENT DOCUMENTS

| | | |
|---|---|---|
| 6,511,809 B2 | 1/2003 | Baez et al. |
| 2002/0132233 A1 | 9/2002 | Ren |
| 2005/0026161 A1 | 2/2005 | Jablonski et al. |
| 2005/0239108 A1 | 10/2005 | Barletta et al. |

OTHER PUBLICATIONS

Kelman et al. (Journal of Biological Chemistry, 1999, vol. 274, No. 40, p. 28751-28761).*
TaqStart Antibody User Manual (Clontech, Mar. 2005, p. 1-15).*
Lind (J. Immun. Meth. 2005, 304:107-116, IDS reference).*
van der Meer et al. (EMBO, 1983, 2(2):233-237).*
Liu et al. (Biotechniques, 2002, 33(1):129-138).*
Williams et al. (Gene, 1988, 43(3):319-324, cited Abstract only).*
H.-T. Zhang et al. In Proc. Natl. Sci. USA vol. 98(10):5497-5502 (May 8, 2001).
T.C. Chang and S.H. Huang. In J. Immunol. Methods vol. 208(1):35-42 (Oct. 13, 1997).
C.M. Niemeyer et al. 'Self-assembly of DNA-streptavidin nanostructures and their use as reagents in immuno-PCR.' In Nucleic Acids Res. vol. 27(23):4553-4561 (Dec. 1, 1999).
C.M. Niemeyer et al. 'Immuno-PCR: high sensitivity detection of proteins by nucleic acid amplification.' In Trends in Biotechnology vol. 23(4):208-216 (Apr. 2005).
Gullberg et al., Proc. Natl. Sci. USA, vol. 101(22):8420-24 (2004).
Barletta, Janet, et al., "Applications of real-time immune-polymerase chain reaction (rt-IPCR) for the rapid diagnoses of viral antigens and pathologic proteins", Molecular Aspects of Medicine 27 (2006) 224-253.
Choi, J.J. et al., "Protein Trans-splicing and Characterization of a S01;it Family B-type DNA Polymerase from the Hyperthermophilic Archaeal Parasite Nanoarchaeum equtans", Journal Molecular Biol. 356:1093-1106, 2006.
Kelman, Z. et al., "Isolation and Characterization of a Split B-type DNA Polymerase from the Archaeon Methanobacterium thermoautotrophicum delta H", J. Biol. Chem. 274(40):28751-28761, 1998.
Lind, K. et al., "Development and evaluation of three real-time immuno-PCR assemblages for quantification of PSA", J. Immunological Methods, 304:107-116, 2005.
Niemeyer, C.M., et al., "Detecting antigens by quantitative immuno-PCR", Nature Protocols, vol. 2, No. 8, pp. 1918-1930, 2007.
Pohler, J.R.G, et al. "An in vivo analysis of the localization and interactions of human p66 DNA polymerase gamma subunit", BMC Molecular Biology, 6:17-30, 2005.
Gullberg et al., PNAS, 2004, vol. 101, No. 22, p. 8420-8424.
Kelman et al., Journal of Biological Chemistry, 1999, vol. 274, No. 40, p. 28751-28761.
Platinum Taq, Invitrogen Catalog #10966-018/026.
Josefsson et al., Journal of Clinical Microbiology, 1999, vol. 37, No. 3, p. 490-496.
Liu et al., Biotechniques, 2002, 33(1):129-138.
Final Office Action in U.S. Appl. No. 11/897,892, mailed Jun. 2, 2009.
Official Communication, European Patent Application No. 08 781 799.5, mailed Oct. 20, 2011.
Barletta, J., Molecular Aspects of Medicine, vol. 27, pp. 224-254; 2006.
Choi, J.J. et al., Journal of Molecular Biology, vol. 356, pp. 1093-1106, 2006.
Kelman, Z. et al., Journal of Biological Chemistry, vol. 274, No. 40, pp. 28751-28761, 1999.
Niemeyer, C.M., Nature Protocols, vol. 2, No. 8, 1918-1930, 2007.

* cited by examiner

SEQUENCE LISTING

```
<160> NUMBER OF SEQ ID NOS: 28

<210> SEQ ID NO 1
<211> LENGTH: 605
<212> TYPE: PRT
<213> ORGANISM: Escherichia coli
<220> FEATURE:
<221> NAME/KEY: MOD_RES
<222> LOCATION: (1)
<223> OTHER INFORMATION: Met or Val
<220> FEATURE:
<221> NAME/KEY: MOD_RES
<222> LOCATION: (32)
<223> OTHER INFORMATION: Ala or Asp
<220> FEATURE:
<221> NAME/KEY: MOD_RES
<222> LOCATION: (34)
<223> OTHER INFORMATION: Ala or Glu

<400> SEQUENCE: 1

Xaa Ile Ser Tyr Asp Asn Tyr Val Thr Ile Leu Asp Glu Glu Thr Leu
  1               5                  10                  15

Lys Ala Trp Ile Ala Lys Leu Glu Lys Ala Pro Val Phe Ala Phe Xaa
             20                  25                  30

Thr Xaa Thr Asp Ser Leu Asp Asn Ile Ser Ala Asn Leu Val Gly Leu
         35                  40                  45

Ser Phe Ala Ile Glu Pro Gly Val Ala Ala Tyr Ile Pro Val Ala His
     50                  55                  60

Asp Tyr Leu Asp Ala Pro Asp Gln Ile Ser Arg Glu Arg Ala Leu Glu
 65                  70                  75                  80

Leu Leu Lys Pro Leu Leu Glu Asp Glu Lys Ala Leu Lys Val Gly Gln
                 85                  90                  95

Asn Leu Lys Tyr Asp Arg Gly Ile Leu Ala Asn Tyr Gly Ile Glu Leu
            100                 105                 110

Arg Gly Ile Ala Phe Asp Thr Met Leu Glu Ser Tyr Ile Leu Asn Ser
        115                 120                 125

Val Ala Gly Arg His Asp Met Asp Ser Leu Ala Glu Arg Trp Leu Lys
    130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His Lys Gly Pro Leu Asn Val Phe Glu Asn Ile Glu Met
        195                 200                 205

Pro Leu Val Pro Val Leu Ser Arg Ile Glu Arg Asn Gly Val Lys Ile
    210                 215                 220
```

```
Asp Pro Lys Val Leu His Asn His Ser Glu Glu Leu Thr Leu Arg Leu
225                 230                 235                 240

Ala Glu Leu Glu Lys Ala His Glu Ile Ala Gly Glu Glu Phe Asn
        245                 250                 255

Leu Ser Ser Thr Lys Gln Leu Gln Thr Ile Leu Phe Gly Lys Gln Gly
            260                 265                 270

Ile Lys Pro Leu Lys Lys Thr Pro Gly Gly Ala Pro Ser Thr Ser Glu
        275                 280                 285

Glu Val Leu Glu Glu Leu Ala Leu Asp Tyr Pro Leu Pro Lys Val Ile
        290                 295                 300

Leu Glu Tyr Arg Gly Leu Ala Lys Leu Lys Ser Thr Tyr Thr Asp Lys
305                 310                 315                 320

Leu Pro Leu Met Ile Asn Pro Lys Thr Gly Arg Val His Thr Ser Tyr
                325                 330                 335

His Gln Ala Val Thr Ala Thr Gly Arg Leu Ser Ser Thr Asp Pro Asn
            340                 345                 350

Leu Gln Asn Ile Pro Val Arg Asn Glu Glu Gly Arg Arg Ile Arg Gln
        355                 360                 365

Ala Phe Ile Ala Pro Glu Asp Tyr Val Ile Val Ser Ala Asp Tyr Ser
370                 375                 380

Gln Ile Glu Leu Arg Ile Met Ala His Leu Ser Arg Asp Lys Gly Leu
385                 390                 395                 400

Leu Thr Ala Phe Ala Glu Gly Lys Asp Ile His Arg Ala Thr Ala Ala
                405                 410                 415

Glu Val Phe Gly Leu Pro Leu Glu Thr Val Thr Ser Glu Gln Arg Arg
            420                 425                 430

Ser Ala Lys Ala Ile Asn Phe Gly Leu Ile Tyr Gly Met Ser Ala Phe
        435                 440                 445

Gly Leu Ala Arg Gln Leu Asn Ile Pro Arg Lys Glu Ala Gln Lys Tyr
450                 455                 460

Met Asp Leu Tyr Phe Glu Arg Tyr Pro Gly Val Leu Glu Tyr Met Glu
465                 470                 475                 480

Arg Thr Arg Ala Gln Ala Lys Glu Gln Gly Tyr Val Glu Thr Leu Asp
                485                 490                 495

Gly Arg Arg Leu Tyr Leu Pro Asp Ile Lys Ser Ser Asn Gly Ala Arg
            500                 505                 510

Arg Ala Ala Ala Glu Arg Ala Ala Ile Asn Ala Pro Met Gln Gly Thr
        515                 520                 525

Ala Ala Asp Ile Ile Lys Arg Ala Met Ile Ala Val Asp Ala Trp Leu
530                 535                 540

Gln Ala Glu Gln Pro Arg Val Arg Met Ile Met Gln Val His Asp Glu
545                 550                 555                 560

Leu Val Phe Glu Val His Lys Asp Asp Val Asp Ala Val Ala Lys Gln
                565                 570                 575

Ile His Gln Leu Met Glu Asn Cys Thr Arg Leu Asp Val Pro Leu Leu
            580                 585                 590

Val Glu Val Gly Ser Gly Glu Asn Trp Asp Gln Ala His
        595                 600                 605

<210> SEQ ID NO 2
<211> LENGTH: 225
<212> TYPE: PRT
<213> ORGANISM: Escherichia coli
```

```
<400> SEQUENCE: 2

Val Ile Ser Tyr Asp Asn Tyr Val Thr Ile Leu Asp Glu Glu Thr Leu
  1               5                  10                  15

Lys Ala Trp Ile Ala Lys Leu Glu Lys Ala Pro Val Phe Ala Phe Ala
                 20                  25                  30

Thr Ala Thr Asp Ser Leu Asp Asn Ile Ser Ala Asn Leu Val Gly Leu
             35                  40                  45

Ser Phe Ala Ile Glu Pro Gly Val Ala Ala Tyr Ile Pro Val Ala His
 50                  55                  60

Asp Tyr Leu Asp Ala Pro Asp Gln Ile Ser Arg Glu Arg Ala Leu Glu
 65                  70                  75                  80

Leu Leu Lys Pro Leu Leu Glu Asp Glu Lys Ala Leu Lys Val Gly Gln
                 85                  90                  95

Asn Leu Lys Tyr Asp Arg Gly Ile Leu Ala Asn Tyr Gly Ile Glu Leu
                100                 105                 110

Arg Gly Ile Ala Phe Asp Thr Met Leu Glu Ser Tyr Ile Leu Asn Ser
            115                 120                 125

Val Ala Gly Arg His Asp Met Asp Ser Leu Ala Glu Arg Trp Leu Lys
130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His Lys Gly Pro Leu Asn Val Phe Glu Asn Ile Glu Met
        195                 200                 205

Pro Leu Val Pro Val Leu Ser Arg Ile Glu Arg Asn Gly Val Lys Ile
        210                 215                 220

Asp
225

<210> SEQ ID NO 3
<211> LENGTH: 381
<212> TYPE: PRT
<213> ORGANISM: Escherichia coli

<400> SEQUENCE: 3

Asp Pro Lys Val Leu His Asn His Ser Glu Glu Leu Thr Leu Arg Leu
  1               5                  10                  15

Ala Glu Leu Glu Lys Lys Ala His Glu Ile Ala Gly Glu Glu Phe Asn
                 20                  25                  30

Leu Ser Ser Thr Lys Gln Leu Gln Thr Ile Leu Phe Glu Lys Gln Gly
             35                  40                  45

Ile Lys Pro Leu Lys Lys Thr Pro Gly Gly Ala Pro Ser Thr Ser Glu
 50                  55                  60

Glu Val Leu Glu Glu Leu Ala Leu Asp Tyr Pro Leu Pro Lys Val Ile
 65                  70                  75                  80

Leu Glu Tyr Arg Gly Leu Ala Lys Leu Lys Ser Thr Tyr Thr Asp Lys
                 85                  90                  95

Leu Pro Leu Met Ile Asn Pro Lys Thr Gly Arg Val His Thr Ser Tyr
                100                 105                 110

His Gln Ala Val Thr Ala Thr Gly Arg Leu Ser Ser Thr Asp Pro Asn
            115                 120                 125
```

```
Leu Gln Asn Ile Pro Val Arg Asn Glu Glu Gly Arg Ile Arg Gln
130                 135                 140

Ala Phe Ile Ala Pro Glu Asp Tyr Val Ile Val Ser Ala Asp Tyr Ser
145                 150                 155                 160

Gln Ile Glu Leu Arg Ile Met Ala His Leu Ser Arg Asp Lys Gly Leu
            165                 170                 175

Leu Thr Ala Phe Ala Glu Gly Lys Asp Ile His Arg Ala Thr Ala Ala
            180                 185                 190

Glu Val Phe Gly Leu Pro Leu Glu Thr Val Thr Ser Glu Gln Arg Arg
        195                 200                 205

Ser Ala Lys Ala Ile Asn Phe Gly Leu Ile Tyr Gly Met Ser Ala Phe
210                 215                 220

Gly Leu Ala Arg Gln Leu Asn Ile Pro Arg Lys Glu Ala Gln Lys Tyr
225                 230                 235                 240

Met Asp Leu Tyr Phe Glu Arg Tyr Pro Gly Val Leu Glu Tyr Met Glu
            245                 250                 255

Arg Thr Arg Ala Gln Ala Lys Glu Gln Gly Tyr Val Glu Thr Leu Asp
            260                 265                 270

Gly Arg Arg Leu Tyr Leu Pro Asp Ile Lys Ser Ser Asn Gly Ala Arg
        275                 280                 285

Arg Ala Ala Ala Glu Arg Ala Ala Ile Asn Ala Pro Met Gln Gly Thr
290                 295                 300

Ala Ala Asp Ile Ile Lys Arg Ala Met Ile Ala Val Asp Ala Trp Leu
305                 310                 315                 320

Gln Ala Glu Gln Pro Arg Val Arg Met Ile Met Gln Val His Asp Glu
            325                 330                 335

Leu Val Phe Glu Val His Lys Asp Asp Val Asp Ala Val Ala Lys Gln
            340                 345                 350

Ile His Gln Leu Met Glu Asn Cys Thr Arg Leu Asp Val Pro Leu Leu
        355                 360                 365

Val Glu Val Gly Ser Gly Glu Asn Trp Asp Gln Ala His
    370                 375                 380

<210> SEQ ID NO 4
<211> LENGTH: 83
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (56)..(56)
<223> OTHER INFORMATION: 2'-O-methoxy-c
<220> FEATURE:
<221> NAME/KEY: modified_base
<222> LOCATION: (57)..(57)
<223> OTHER INFORMATION: 2'-O-methoxy-g
<220> FEATURE:
<221> NAME/KEY: modified_base
<222> LOCATION: (59)..(60)
<223> OTHER INFORMATION: 2'-O-methoxy-c

<400> SEQUENCE: 4 ttttttgct cgacggtgaa ugaugtaggu accagcagua acucgagcac gucuucgacc    60
aaatcuggau attgcagcct cgt                                           83
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acgaggctgc aatatccaga                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgctcgacgg tgaatgatgt                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatccgaccc ctccaaggac t                                                  21

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcgcagatct cgagctgctg aacggcgtcg a                                       31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
catgggcagc agccatcatc atcatcatca c                                       31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccgtcgtcgg tagtagtagt agtagtgcgg c                                       31

<210> SEQ ID NO 11
```

<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
taatacgact cactatagg                                                  19

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcgacggatc gggcggtggc tccggtggcg gcagcggcc                             39

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcctagcccg ccaccgaggc caccgccgtc gccggagct                             39

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcgcgtcgac gaagaaaaat tcggtgtttc c                                    31

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcgcctcgag cttttcttca gcagcttcaa cc                                   32

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcgcgtcgac ggtggcggtg gctcggtgat ttcttatgac aactacgtca                 50

<210> SEQ ID NO 17
<211> LENGTH: 32

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgcaagctt agtgcgcctg atcccagttt tc                                    32

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgcaagctt aatcgatctt cacaccgtta c                                     31

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcgcgtcgac ggtggcagcg atccgaaagt cctgcacaa                             39

<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
actagtgatt ataaggatga cgatgacaaa gattacaaag atgatgacga taagtag         57

<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cactaatatt cctactgcta ctgtttctaa tgtttctact actgctattc atcttaa         57

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgtgcactcg agttgctaaa                                                  20

<210> SEQ ID NO 23
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 23
gcgcactagt atgcgcctga tcccagtttt c                                    31

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctacttgtca tcgtcatcct tat                                             23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cggcagaagt gtttggtttg                                                 20

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Ser Ser Gly Gly Gly Ser Gly
 1               5                  10

<210> SEQ ID NO 27
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 ttttttgct cgacggtgaa tgatgtaggt accagcagta actcgagcac gtcttcgacc      60
aaatctggat attgcagcct cgt                                             83

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggtgcggcaa gtttctttcg gaggctgcaa gc                                   32
```

ANALYTE DETECTION ASSAYS

This is the U.S. National Phase application of International Application PCT/US2008/069975, filed 14 Jul. 2008, which claims the benefit of U.S. Provisional Application No. 60/959,908, filed 17 Jul. 2007. This U.S. National Stage application is also a continuation-in-part of U.S. application Ser. No. 11/897,892, filed 31 Aug. 2007 now U.S. Pat. No. 7,659,069.

FIELD OF THE INVENTION

The present invention relates to the field of biotechnology. More specifically, it relates to convenient, rapid, and sensitive methods, compositions, and kits for detecting and quantifying analytes using analyte-specific binding molecules having a binding moiety coupled to a polymerase or a portion thereof. Upon binding of the analyte to the binding moiety, the polymerase provides a means to generate a template for a nucleic acid amplification reaction. Detection of the presence of the amplification product is indicative of the presence of the analyte in the sample.

BACKGROUND

The development of immunoassays and advances in nucleic acid detection have advanced the art of the detection of biological samples. The enzyme-linked immunosorbent assay (ELISA) allows for the high throughput screening of samples for the presence of proteins in samples. The presence of the analyte is frequently detected by the use of an enzymatic, colorimetric assay based on alkaline phosphatase or horseradish peroxidase. This limits the sensitivity and the range of the assay depending on the range of detection of colorimetric changes of the enzyme substrate. This requires either initial screening to determine an approximate amount of the analyte in the serum, or the use of a large series of dilutions to ensure that a sample is tested within the detection range of the specific methods and reagents used. Other problems with this method include high background levels as well as low sensitivity. For example, direct binding of horseradish peroxidase to an ELISA plate results in unspecific background signal. To reduce unspecific binding, blocking solutions containing relatively inert proteins (milk or serum albumin) are added to the assay. However, the unspecific binding resulting in a background signal is not eliminated, thereby resulting in lower sensitivity of the assay.

To address these limitations, nucleic acid based detection methods for use in conjunction with enzyme-based detection of analytes in samples have been developed. Several so called "immuno-PCR assays" are known in the art and combine aspects of an ELISA assay with PCR. The assays produce a detectable signal when the probes/antibodies bind an analyte in a sample allowing for the amplification of a target nucleic acid.

For example, U.S. Pat. No. 5,665,539 combines detection with an antibody and the polymerase chain reaction (PCR) to increase sensitivity for the detection of a specific protein. In a standard immuno-PCR protocol, an antibody attached to a nucleic acid sequence binds to an epitope on an antigen molecule. The attachment between the antibody and nucleic acid occurs via a linker with bispecific affinity for nucleic acids and antibodies, thus resulting in the formation of a specific antigen-antibody-DNA conjugate. Subsequently, a segment of the attached nucleic acid sequence is amplified by PCR and the PCR products are detected by gel electrophoresis. However, linking DNA to antibodies has been problematic because DNA is sticky and any unbound DNA is not easily washed from the system prior to detection, giving rise to non-specific binding and high background in the assay.

Other such assays are described in U.S. Publication No. 2002/0132233, U.S. Pat. No. 5,985,548, U.S. Publication No. 2005/0026161 and U.S. Publication No. 2005/0239108. U.S. Patent Publication Nos. 2002/0132233, 2005/0026161, and 2005/0239108 are directed to sandwich immuno-PCR methods using analyte-specific antibodies coupled directly or indirectly (e.g., using a biotin/avidin binding pair) to an oligonucleotide. Binding of the antibody to the analyte in the sample results in an analyte-antibody-DNA complex. Antibody binding is detected by subjecting the complex to amplification conditions, where the attached oligonucleotide is used as a template to generate an amplification product. None of these methods, however, couples an antibody, or other binding molecule, with a polymerase. Rather they all require the use of an antibody coupled directly or indirectly to an oligonucleotide. Non-specific binding of the antibody/DNA conjugate contributes to high background and interferes with the ability to detect small quantities of analyte. In addition, none of the methods uses two different polymerase reactions to generate the amplification product and increase the sensitivity of the assay.

U.S. Pat. No. 5,985,548 discloses another sandwich immuno PCR method in which a binding molecule, such as an antibody, is conjugated to a target oligonucleotide. As with the immuno-PCR methods discussed above, non-specific binding of the antibody/DNA conjugate contributes to high background and interferes with the ability to detect small quantities of analyte. In another embodiment, U.S. Pat. No. 5,985,548 discloses a sandwich immuno PCR method in which a binding molecule, such as an antibody, is conjugated to an enzyme, such as horseradish peroxidase, that can activate a moiety (e.g., tyramine) on the target oligonucleotide. Once the tyramine is activated, it forms a reactive intermediate that binds to a receptor on the solid support, thereby immobilizing the target oligonucleotide. The immobilized target oligonucleotide is then subjected to an amplification reaction. Although this embodiment avoids the use of reporter conjugates comprising DNA linked to an antibody or other binding moiety, it requires the use of a target nucleic acid having a moiety that is activated by the enzyme attached to the reporter conjugate and that upon activation forms a reactive intermediate that must bind to an immobilized receptor before amplification. Furthermore, none of the methods in U.S. Pat. No. 5,985,548 uses two different polymerase reactions to generate the amplification product.

SUMMARY OF THE INVENTION

This disclosure provides methods, kits and compositions for the detection of an analyte. The methods, kits and compositions are particularly suited for the detection and quantification of analytes in solution. In certain methods a binding molecule, coupled to a first polymerase, binds an analyte forming a complex comprising the analyte, the binding molecule and the first polymerase. This complex is incubated with a primer and a modified nucleic acid template comprising one or more modified nucleotides that prevent certain polymerases from amplifying the modified template. When the primer anneals to the modified nucleic acid template, it is extended by the first polymerase to synthesize a copy of the modified nucleic acid template that does not contain any of the modified nucleotides. The unmodified copy is then detected in an amplification reaction using a different polymerase that cannot amplify the modified nucleic acid template but can amplify the unmodified copy. Detection of the unmodified copy is indicative of the presence and/or amount of the analyte in the sample. In this way, the use of two different polymerase reactions increases sensitivity, reduces background, and improves reproducibility as the second polymerase will not amplify the modified polynucleotide template unless the modified polynucleotide template is copied by the first polymerase coupled to the binding molecule. In other words, if the binding molecule does not bind to analyte in the sample, the modified polynucleotide will not be copied by the first polymerase and thus will not generate a template for the second polymerase to amplify.

These methods, compositions, and kits combine the specificity of specific binding pair binding reactions (e.g., immunodetection) with the sensitivity of polymerase-based detection reactions. They further allow for an increase in sensitivity and a reduction of background levels over systems that are commercially available by providing a binding molecule, such as an antibody, coupled to a polymerase that can be used to amplify a target nucleic acid that need not be coupled to another binding molecule. In addition, these methods, kits and compositions can be adapted for use with two different polymerase reactions that reduce or eliminate various sources of background seen in commercially available systems.

In one aspect, a method for detecting an analyte is provided. The method involves contacting a sample with a reaction mixture so as to allow the binding of a binding molecule, such as an antibody, to an analyte. The binding molecule is coupled to a first polymerase which is capable of amplifying a modified polynucleotide template comprising one or more modified nucleotides. A first primer anneals to the modified polynucleotide template and is extended by the first polymerase, synthesizing a copy of the modified polynucleotide template that does not contain any of the one or more modified nucleotides ("unmodified copy"). The unmodified copy is then amplified with a second polymerase. The second polymerase is incapable of amplifying the modified polynucleotide template, but is capable of amplifying a non-modified polynucleotide (unmodified copy). The detection of the amplified unmodified copy is indicative of the presence or amount of the analyte in the sample.

In yet another aspect, a composition is provided. The composition includes binding molecule coupled to a first polymerase that is capable of amplifying a modified polynucleotide template. The composition further includes a modified polynucleotide template or a second polymerase that is capable of amplifying a non-modified polynucleotide template (i.e., a copy of the modified polynucleotide template without any modified nucleotides), but which is not capable of amplifying a modified polynucleotide template.

The modified polynucleotide template includes one or more modified nucleotides which interfere/prevent the second polymerase from amplifying the modified polynucleotide template. Suitable modifications include deoxyuracil and 2'-O-methyl modifications. In one embodiment, the polymerase coupled to the binding molecule is a Klenow or T4 polymerase. In a further embodiment, the second polymerase is Pfu DNA polymerase. One of skill in the art can design other polymerase/modified polynucleotide combinations permitting the first polymerase to copy the modified polynucleotide while at the same time preventing the second polymerase from amplifying the modified polynucleotide template.

The binding molecule can be coupled to the first polymerase covalently or non-covalently, including, for example, as an antibody-polymerase fusion protein or via binding through a streptavidin-biotin or an avidin-biotin interaction.

In a preferred embodiment, the binding molecule is a biotinylated antibody and the first polymerase is coupled to a biotin-binding molecule, such as streptavidin or avidin, for example, as a fusion protein.

In another aspect, a method for detecting an analyte in a sample is provided. The method involves incubating a reaction mixture so as to allow binding of binding molecule, such as an antibody, to an analyte. The binding molecule is coupled to a first polymerase that has 3' exonuclease activity and incubated in the presence of a polynucleotide template and an extension primer comprising a 3' flap and a 5' region that introduces a new primer binding site upon extension. The incubation allows the annealing of the primer to the polynucleotide template, the cleavage of the 3' flap by the first polymerase, and the extension of the cleaved primer with the first polymerase. Extension of the cleaved primer forms a template for amplification comprising the new primer binding site introduced by the extension primer. The template for amplification is incubated with at least two primers, one of which anneals to the new primer binding site introduced by the extension primer, and a second polymerase that substantially lacks 3' exonuclease activity and subjected to an amplification reaction. The detection of the amplified template for amplification is indicative of the presence or amount of the analyte in the sample. In one embodiment, the extension primer is designed so that it does not anneal to a target nucleic acid at a reaction temperature about 41° C. or above. In this embodiment, the incubation with the first polymerase is carried out at a first reaction temperature that permits binding of the binding molecule to the analyte, annealing of the extension primer to the polynucleotide template, cleavage of the 3' flap and extension of the cleaved primer and the amplification reaction with the second polymerase is carried out at a second reaction temperature that is about 41° C. or above. Furthermore, in this embodiment, the second polymerase can have 3' exonuclease activity so long as the second polymerase is inactive below 41° C. In another embodiment, the polynucleotide template comprises one or more modified nucleotides and the second polymerase cannot amplify the modified polynucleotide template. The binding molecule can be coupled to the first polymerase covalently or non-covalently, including, for example, as an antibody-polymerase fusion protein or via binding through a streptavidin-biotin interaction.

In still another embodiment, a composition for practicing the above method is provided. The composition includes binding molecule, such as an antibody, coupled to a polymerase having 3' exonuclease activity, an extension primer having a 3' flap and a 5' region that introduces a new primer binding site into a template for amplification when the extension primer is extended by the polymerase having 3' exonuclease activity and optionally a second polymerase and/or a second primer complementary to the new primer binding site in the template for amplification. Preferably the second polymerase substantially lacks 3' exonuclease activity. In one embodiment, the primer does not anneal to the target at a reaction temperature of about 41° C. or above. The composition may further comprise a polynucleotide template that may or may not be modified.

In addition, in any of the above methods, compositions, and kits, the binding molecule coupled to the polymerase further comprises a spacer molecule, such as a polypeptide linker, located between the binding molecule and the polymerase.

In another aspect, called the split polymerase system, a complex is formed between a first and second analyte specific probe (ASP) and an analyte. Each analyte specific probe comprises a binding moiety coupled to a first or second portion of a first polymerase, such as Klenow. The first and second portions of the polymerase are essentially inactive in isolation but become active if they bind to each other, thus reconstituting essentially complete enzymatic activity. When the first and second ASPs bind the analyte in close proximity to one another the first and second portions of the polymerase are able to interact, forming a functional polymerase complex. The functional polymerase complex then generates a detectable signal which is indicative of the presence and/or amount of the analyte in the sample. The detection method is based on the interplay of two polymerases and a modified polynucleotide template comprising one or more modified nucleotides. More specifically, the reconstituted, functional polymerase complex extends a primer annealed to the modified polynucleotide template to synthesize a copy of the modified polynucleotide template that does not contain any of the one or more modified nucleotides ("unmodified copy"). The unmodified copy is then amplified with a second polymerase and detected. The second polymerase is incapable of amplifying the modified polynucleotide template, but is capable of amplifying the unmodified copy.

In one embodiment, the first polymerase, a first and second portion of which is coupled to a binding molecule, is a Klenow or T4 polymerase. In a further embodiment, the second polymerase is Pfu DNA polymerase. One of skill in the art can design other polymerase/modified polynucleotide combinations permitting the first polymerase to copy the modified polynucleotide while at the same time preventing the second polymerase from amplifying the modified polynucleotide template.

In one aspect of the split polymerase system, a method of detecting an analyte is provided. The method entails contacting a sample with a reaction mixture so as to permit binding of a first ASP and a second ASP to an analyte, annealing of a first primer to a modified polynucleotide template comprising one or more modified nucleotides and extension of the first primer. The first ASP includes a first binding moiety coupled to a first portion of a first polymerase, and the second ASP includes a second binding moiety coupled to a second portion of a first polymerase. When the first and second ASPs bind the analyte in close proximity to one another the first and second portions of the first polymerase are able to interact, forming a functional polymerase complex. The functional polymerase complex may then extend the first primer, which is annealed to the modified polynucleotide template, so as to form a copy of the modified template that does not contain any of the one or more modified nucleotides ("unmodified copy"). Next, the unmodified copy is amplified with a second polymerase so as to produce a detectable signal. The second polymerase is incapable of amplifying the modified polynucleotide template but is capable of amplifying the unmodified copy. The detection of the amplified unmodified copy is indicative of the presence and/or amount of the analyte in the sample.

In yet another aspect of the split polymerase system, a composition is provided. In this embodiment the composition includes a first analyte specific probe, second analyte specific probe and optionally a modified polynucleotide template and/or a second polymerase. The first ASP includes a binding moiety coupled to a first portion of a first polymerase and the second ASP includes a binding moiety coupled to a second portion of a first polymerase. The first and second portions of the first polymerase form a functional polymerase complex when they associate with one another. In one embodiment, the first polymerase is a Klenow or T4. In another embodiment, the first and second binding molecule are coupled to the first and second portions of the polymerase, such as Klenow or T4, covalently or non-covalently, including, for example, as an antibody-polymerase fusion protein or via binding through a streptavidin-biotin interaction. In a preferred embodiment, the first binding molecule is a biotinylated antibody coupled to the first portion of the polymerase by a streptavidin or avidin linkage, and the second binding molecule is a biotinylated antibody coupled to the second portion of the polymerase via a streptavidin or avidin linkage.

The split polymerase system may also be used in and adapted to the methods and compositions described herein that use a primer having a 3' flap and a 5' region that introduces a new primer binding site into a template for amplification.

In yet another aspect, the composition comprises a Klenow fragment, wherein said Klenow fragment has synthetic activity and consists of an amino acid sequence which is 95% or more identical to amino acids 201-605 of SEQ ID NO:1.

In any of the split polymerase methods, compositions, and kits, the ASP optionally comprises a spacer molecule, such as a polypeptide linker, located between the binding moiety and the first or second portion of the polymerase.

In other aspects, kits containing any of the compositions described herein and packaging materials therefor are provided.

In all of these methods, the detection of the unmodified copy or the template for amplification can be performed by numerous methods known in the art, including real-time PCR detection assays (e.g., TAQMAN® (Roche Molecular Systems Inc., Alameda, Calif.) reaction). The first and second polymerase reactions, (synthesis of the unmodified copy and the detection reaction) may be performed as a single step reaction (e.g., same reaction mixture and incubation step) or sequentially (e.g. separate reaction mixtures and incubation steps).

In addition, any of the aspects of the invention may be practiced as a solid-phase detection reaction (e.g., utilizing a capture molecule (e.g., antibody) bound to a plate and a polynucleotide template, which is optionally coupled to a binding molecule, such as an antibody or streptavidin) or a non-solid phase detection reaction (e.g., solution based detection reaction, using a binding molecule, such as an antibody or streptavidin, coupled to a polynucleotide template and a first binding molecule, such as an antibody, coupled to a polymerase or a first and a second analyte-specific probe).

BRIEF DESCRIPTION OF THE DRAWINGS

The accompanying drawings, which are incorporated in and constitute a part of this specification, illustrate certain embodiments of the invention, and together with the written description, serve to explain certain principles of the invention.

DETAILED DESCRIPTION

Figure 1A:
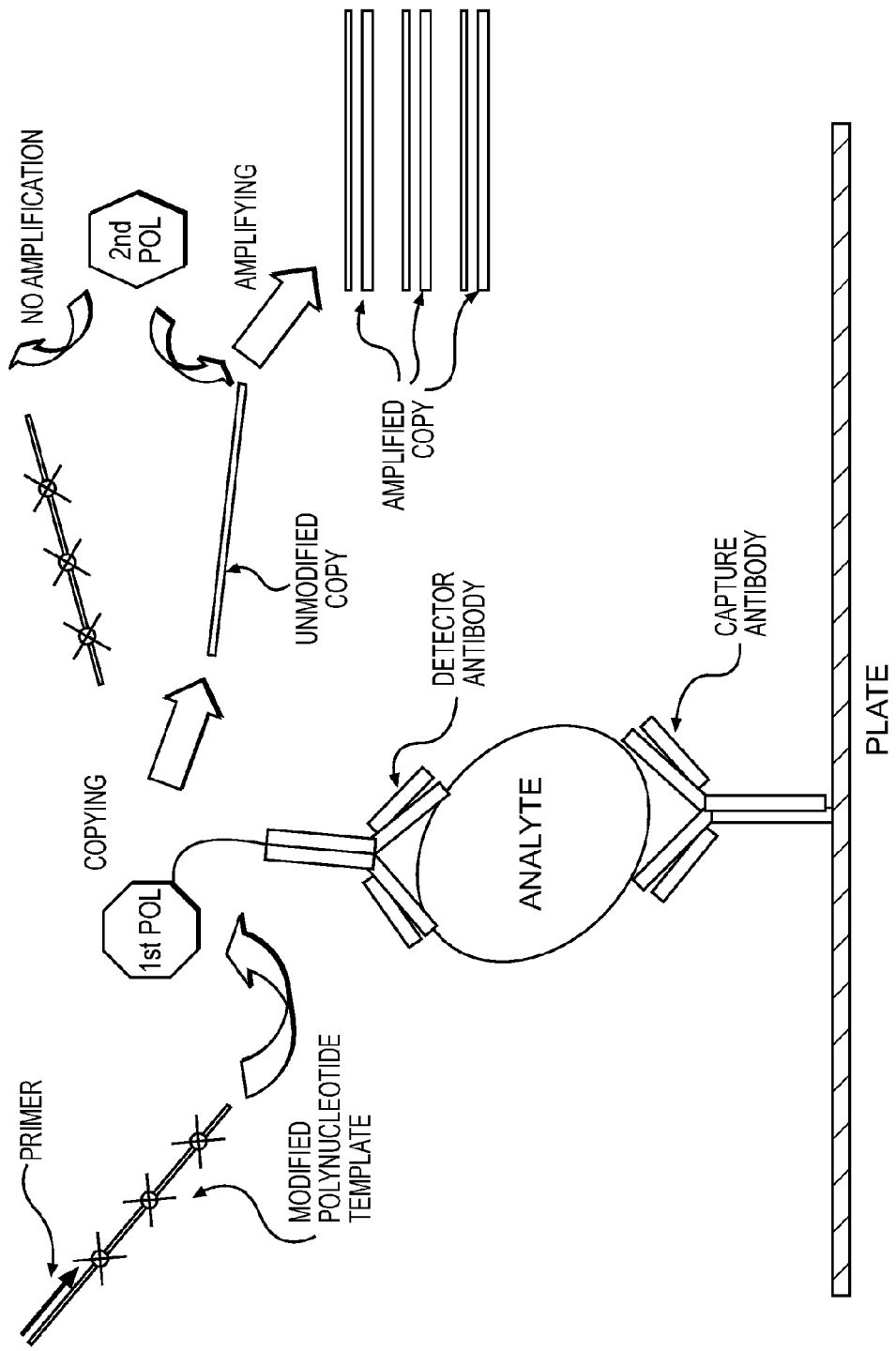
FIG. 1A illustrates one embodiment of a solid-phase detection assay utilizing a modified polynucleotide template.

Reference will now be made in detail to various exemplary embodiments of the invention, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

As discussed above, reagents and methods for immunodetection of substances of interest are known and commercially available. However, these reagents and methods suffer from significant drawbacks, most notably either relatively low sensitivity, poor signal-to-noise ratio (high background signal), or both. In addition, some are specifically designed to function in only a certain manner, and are thus not adaptable for use broadly to detect substances of interest. While immuno-PCR techniques have been devised to improve sensitivity, commercially available technologies still suffer from high signal-to-noise ratio, limiting their usefulness.

The present application discloses methods, compositions and kits that improve signal-to-noise ratio while simultaneously retaining or improving specificity and/or sensitivity of detection assays by using an analyte-specific binding agent that comprises a highly specific binding portion (e.g., an antibody portion) bound to a highly sensitive polymerase portion, where the agent can be incubated with a modified polynucleotide template for the polymerase under conditions that permit the polymerase to synthesize a template for an amplification reaction (e.g., PCR). The template for the amplification reaction is amplified with a second polymerase that is not capable of amplifying the modified polynucleotide template. Using two different polymerases increases sensitivity, reduces background, and improves reproducibility as any residual, nonspecific modified polynucleotide template cannot be amplified by the second polymerase and, therefore, will not become part of the detection signal. Furthermore, the detection reaction may be physically separated from the binding reaction, and background signal due to non-specifically bound reagent can be reduced or eliminated, while sensitivity retained or improved.

DEFINITIONS

As used herein the term "analyte" refers to a substance to be detected or assayed by the method of the present invention. Typical analytes may include, but are not limited to proteins, peptides, cell surface receptor, receptor ligand, nucleic acids, molecules, cells, microorganisms and fragments thereof, or any substance for which a binding moiety, e.g., antibodies, can be developed.

As used herein, a "binding molecule" refers to a molecule which specifically binds to an analyte. Binding molecules include monoclonal, polyclonal, or phage derived antibodies, antibody fragments, peptides, ligands, haptens, nucleic acids, nucleic acid aptamers, protein A, protein G, folate, folate binding proteins, plasminogen, and maleimide and sulfhydryl reactive groups. Additional useful binding molecules are known in the art.

As used herein the term "binding moiety" refers to a molecule which stably binds an analyte. Binding moieties include, but are not limited, to a monoclonal antibody, polyclonal antibody, aptamer, cell surface receptor, receptor ligand, biotin, streptavidin, avidin, protein A and protein G and binding fragments thereof, e.g., Fab. The binding moiety is directly or indirectly coupled to a reactive molecule.

As used herein the terms "analyte specific probe" or "ASP", refers to a molecule having a binding moiety and a reactive moiety (e.g., a first or second portion of a polymerase). The binding moiety is operatively coupled to the reactive moiety. When two or more probes bind in close proximity to one another, the reactive moieties effectively interact. The analyte specific probes are in close proximity to one another when the two probes bind to their respective binding sites on the analyte and their active moieties interact. The binding molecule is directly or indirectly coupled to a reactive moiety.

As used herein, the term "interact", as applied to the reactive moieties of the ASPs, refers to bringing two or more reactive moieties (e.g., first and second portion of a polymerase) within close proximity to one another so as to allow the reactive moieties to physically associate. For example, when a pair of analyte specific probes having a first and second portion of a Polymerase bind to an analyte, the first and second portions of the polymerase are brought into close proximity so as to interact and form a functional polymerase complex. This functional polymerase complex will then extend the 3' end of a primer hybridized to a polynucleotide template so as to form an amplification template. When the first and second portions of the polymerase are separated (do not interact) the portions substantially lack synthetic activity.

As used herein, the term "substantially lacking synthetic activity" refers to a first or second portion of a polymerase that has no more than 50%, 40%, 30%, 20% or 10% and preferably less than 1% of the synthetic activity of a functional polymerase complex.

As used herein, the term "portion" with reference to a first polymerase refers to a fragment of a nucleic acid polymerase that substantially lacks nucleic acid synthetic activity when isolated, but which has nucleic acid synthetic activity when it interacts with a second portion of the nucleic acid polymerase. As used herein a "portion" with respect to a first polymerase refers to fragments of 50-1000 amino acids, but which are less than the full-length polymerase. In one embodiment, the portion has at least 50, 60, 70, 80, 90, 100, 150, 200, 250, 300, 350, 400, 450, 500, 550, or 600 or more amino acids of a nucleic acid polymerase, but less than the full-length polymerase. For example, a first portion of Klenow can have the amino acid sequence of SEQ ID NO: 2, a second portion of the Klenow can have the amino acid sequence of SEQ ID NO:3, while the full-length Klenow comprises the amino acid sequence of SEQ ID NO:1.

As used herein, the term "functional polymerase complex" refers to two or more portions of a polymerase, as defined herein, which interact to form a polypeptide complex having synthetic activity (polymerase activity) that is at least 2× the synthetic activity of either portion alone (e.g., not in complex).

In a preferred embodiment, the binding moiety of the ASP is an antibody.

As used herein, the term "antibody" refers to an immunoglobulin protein which is capable of binding an antigen, e.g., analyte. Antibody includes any portion of an antibody that retains the ability to bind to the epitope recognized by the full length antibody, generally termed "epitope-binding fragments." Examples of antibody fragments preferably include, but are not limited to, Fab, Fab', and F(ab')$_2$, Fd, single-chain Fvs (scFv), single-chain antibodies, disulfide-linked Fvs (sdFv) and fragments comprising either a $V_L$ or $V_H$ domain. Epitope-binding fragments, including single-chain antibodies, may comprise the variable region(s) alone or in combination with the entirety or a portion of the following: hinge region, $C_H1$, $C_H2$, and $C_H3$ domains.

As used herein, "nucleic acid polymerase" or "polymerase" refers to an enzyme that catalyzes the polymerization of nucleotides. Generally, the enzyme will initiate synthesis at the 3'-end of the primer annealed to a nucleic acid template sequence, and will proceed toward the 5' end of the template strand. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475: 32), *Thermococcus litoralis* (Tli) DNA polymerase (also referred to as Vent DNA polymerase, Cariello et al., 1991, Nucleic Acids Res, 19: 4193), 9° Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), *Pyrococcus GB-D* (PGB-D) DNA polymerase (Juncosa-Ginesta et al., 1994, Biotechniques, 16:820), T4 DNA polymerase and the Klenow fragment of the *E. coli* DNA polymerase I ("Klenow"). The polymerase activity of any of the above enzymes can be determined by methods well known in the art. In one embodiment, a method of the invention utilizes a polymerase that possesses 3' nuclease activity and a second polymerase that substantially lacks 3' nuclease activity. Polymerases that possess 3' nuclease activity or substantially lack 3' nuclease activity are known in the art and described herein. In another embodiment, the method utilizes a first nucleic acid polymerase that is capable of amplifying a modified polynucleotide template and a second nucleic acid polymerase that is incapable or substantially incapable of amplifying a modified polynucleotide template. Polymerases capable of amplifying a modified polynucleotide template and polymerases that are incapable or substantially incapable of amplifying a modified polynucleotide template are known in the art and described herein. In the context of the methods, compositions, and kits disclosed herein, a second polymerase "incapable" of amplifying or that "cannot" amplify or copy a modified polynucleotide template does not mean that the second polymerase cannot under certain conditions amplify or copy the modified polynucleotide template but rather that the second polymerase is substantially less efficient than the first polymerase at amplifying or copying the modified polynucleotide template, including, for example, at least 100-fold, at least 1,000-fold, at least 10,000 fold, at least 100,000 fold, or at least 1,000,000 fold less efficient at amplifying the modified polynucleotide template as compared to the first polymerase. In the split polymerase system, the methods utilize a first polymerase that is split into a first and second portion. In one embodiment, the first polymerase is a family A polymerase. In another embodiment, the polymerase that is split into a first and second portion is Klenow.

As used herein, "coupled" refers to the association of two molecules though covalently and non-covalent interactions, e.g., by hydrogen, ionic, or Van-der-Waals bonds. Such bonds may be formed between at least two of the same or different atoms or ions as a result of redistribution of electron densities of those atoms or ions. For example, an enzyme may be coupled to an antibody as an antibody-enzyme fusion protein, via binding through a streptavidin-biotin interaction or through binding via an Fc protein A/G interaction (e.g., polymerase is coupled to protein A/G which in turn binds the Fc region of the antibody).

An "antibody binding molecule" as described herein is a ligand that binds to an antibody. Generally the ligand is not bound to the antibody through the antigen binding site. Non-limiting examples include protein A, protein L and protein G.

As used herein, a "fusion polypeptide" refers to a polypeptide comprising two or more polypeptides that are linked in frame to each other. As used herein, the term "linked" or "fused" means the linking together of two or more segments of a polypeptide or nucleic acid to form a fusion molecule that encodes two or more polypeptides linked in frame to each other. The two or more polypeptides may be linked directly or via a linker.

As used herein, the term "oligonucleotide" or "polynucleotide" refers to polydeoxyribonucleotides (containing 2-deoxy-D-ribose), to polyribonucleotides (containing D-ribose) and to any polynucleotide which is an N-glycoside of a purine or pyrimidine base, or modified purine or pyrimidine base. An oligonucleotide may hybridize to other oligonucleotide or may self-hybridize, e.g., hairpin structure. An oligonucleotide includes, without limitation, single- and double-stranded oligonucleotides.

As used herein, the term "polynucleotide template" refers to nucleic acid sequence to which a primer hybridizes and which is replicated by a nucleic acid polymerase, e.g., in a PCR or primer extension reaction. In one embodiment, the polynucleotide template is replicated when a first and second portion of a first polymerase interact so as to form a functional polymerase complex. As used herein, an "unmodified copy" is a copy of the modified polynucleotide template synthesized by the first polymerase or the functional polymerase complex that does not contain any of the modified nucleotides that are present in the modified polynucleotide template. The unmodified copy is amplified by a second polymerase that is incapable of amplifying the modified polynucleotide template.

As used herein, "a modified polynucleotide template" or "modified nucleic acid template" refers to a polynucleotide template with one or more non-natural nucleotides that prevents the template from being copied by a second polymerase (e.g., Pfu polymerase) but not by a first polymerase (e.g., Klenow or T4 polymerase). Such non-natural modifications include replacing thymine with a uracil and replacing 2' hydroxyls with 2'-O-methyl. Other suitable modifications may include 3' to 5' reversed deoxyribonucleotides (Qiang Liu et al. Biotechniques. 33:129-138 (July 2002)), hypoxanthine and other non-traditional nucleotides known in the art and described herein. A "modified nucleic acid template" cannot be copied, (e.g., amplified) by a Pfu polymerase (*Pyrococcus furiosus* (Pfu) DNA polymerase (Lundberg et al., 1991, Gene, 108:1)), under the reaction conditions described herein (e.g., 1×Pfu buffer at 60-72° C.) but can be replicated by Klenow under conditions suitable for Klenow (10 mM Tris-HCl (pH 7.5), 5 mM MgCl$_2$, 7.5 mM DTT at room temperature). Assays for determining whether a template is a modified polynucleotide template are described herein and known in the art.

As used herein, the term "complementary" refers to the concept of sequence complementarity between regions of two polynucleotide/oligonucleotide strands. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Complementary" can refer to a first polynucleotide that is 100% or "fully" complementary to a second polynucleotide and thus forms a base pair at every nucleotide position. "Complementary" also can refer to a first polynucleotide that is not 100% complementary (e.g., 90%, 80%, 70%, 60% complementary) contains mismatched nucleotides at one or more nucleotide positions.

As used herein, the terms "hybridization" or "annealing" is used to describe the pairing of complementary (including partially complementary) polynucleotide/oligonucleotide strands, e.g., primer and template. Hybridization and the strength of hybridization (i.e., the strength of the association between polynucleotide strands) is impacted by many factors well known in the art including the degree of complementarity between the polynucleotides, stringency of the conditions involved, the melting temperature ($T_m$) of the formed hybrid, the presence of other components (e.g., the presence or absence of polyethylene glycol), the molarity of the hybridizing strands, and the G:C content of the polynucleotide strands.

As used herein, when one polynucleotide is said to "hybridize" or "anneal" to another polynucleotide, it means that there is some complementarity between the two polynucleotides or that the two polynucleotides form a hybrid under high stringency conditions. When one polynucleotide is said to not hybridize to another polynucleotide, it means that there is no sequence complementarity between the two polynucleotides or that no hybrid forms between the two polynucleotides at a high stringency condition.

The term "nuclease" refers to an enzyme that possesses 5' to 3' endonuclease activity and/or 5' to 3' exonuclease activity (5' exonuclease). Enzymes possessing 5' to 3' exonuclease activity include DNA polymerase, e.g. DNA polymerase I from *E. coli*, and DNA polymerase from *Thermus aquaticus* (Taq), *Thermus thermophilus* (Tth), and *Thermus flavus* (Tfl). The term "nuclease" also embodies FEN nucleases. FEN enzymes possess 5' to 3' exonuclease activity and cleave 5' nucleic acid flaps through the hydrolytic cleavage of the phosphodiester bond at the junction of single stranded and double stranded DNA. FEN nuclease enzymes include FEN enzymes derived from *Archaeglobus fulgidus*, *Methanococcus jannaschii*, *Pyrococcus furiosus*, human, mouse or *Xenopus laevis*. A nuclease also includes *Saccharomyces cerevisiae* RAD27, and *Schizosaccharomyces pombe* RAD2, Pol I DNA polymerase associated 5' to 3' exonuclease domain, (e.g. *E. coli*, *Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease.

The term "3' nuclease" or "3' exonuclease" refers to an enzyme (e.g., polymerase) that possesses 3' to 5' endonuclease activity (3' endonuclease) and/or 3' to 5' exonuclease activity (3' exonuclease). Enzymes possessing 3' nuclease activity are described herein or known in the art.

The term "substantially lacks 3' nuclease activity" means that the enzyme possesses no more than 5% or 10% and preferably less than 0.1%, 0.5%, or 1% of the 3' nuclease activity of a wild type polymerase, such as T4, T7, Pfu, or Klenow DNA polymerase.

As used herein, a "3' flap" refers to a single stranded nucleic acid flap that protrudes as a 3' single strand when hybridized to a target nucleic acid. The 3' flap is non-complementary to the target nucleic acid and is cleaved by a 3' nuclease.

As used herein, "cleavage reaction" refers to enzymatically separating an oligonucleotide (i.e. not physically linked to other fragments or nucleic acids by phosphodiester bonds) into fragments or nucleotides and fragments that are released from the oligonucleotide. A cleavage reaction is performed by an exonuclease activity, endonuclease activity or restriction enzyme activity. Cleavage reactions utilizing an endonuclease activity include the INVADER® detection assay (Third Wave Technologies; Madison, Wis.) which is described in U.S. Pat. No. 6,348,314 and is herein incorporated by reference in their entirety. Cleavage reaction assays encompassed by the present methods also include molecular beacon detection assays (supplied by a variety of commercial sources) and TAQMAN® (Roche Molecular Systems Inc., Alameda, Calif.) detection assays which are described in U.S. Pat. Nos. 5,723,591; 5,925,517 and 5,804,375, each of which is herein incorporated by reference in its entirety. Cleavage reactions useful in the present invention are also described in U.S. Pat. No. 6,548,250 which is herein incorporated by reference. Such cleavage reactions may be practiced by the nuclease in the methods of the invention.

As used herein, the term "cleavage product" is an oligonucleotide fragment that has been cleaved and released into solution in a cleavage reaction by a nuclease.

As used herein, the term "amplification", when applied to a nucleic acid sequence, refers to a process whereby one or more copies of a particular nucleic acid sequence is generated from a template nucleic acid. Generally, amplification is carried out using a polymerase chain reaction (PCR) or ligase chain reaction (LCR) technologies well known in the art (Dieffenbach, C. W. and G. S. Dveksler (1995) *PCR Primer, a Laboratory Manual*, Cold Spring Harbor Press, Plainview, N.Y.). However, as used herein, amplification is also intended to include a single step replication/copying of a nucleic acid sequence (e.g., primer extension reaction).

In any of the methods described herein, synthesis of the amplification template and the detection reaction may be performed as a single step reaction (e.g., same reaction mixture and incubation step) or sequentially (e.g. separate reaction mixtures and incubation steps). The second polymerase can be any polymerase which is capable of amplifying a non-modified polynucleotide template but which is not capable of amplifying a modified polynucleotide template, for example, under the first primer extension reaction conditions (e.g., Pfu polymerase).

In another embodiment, the second polymerase is a Taq polymerase, such as a chemically-treated hot start version of Taq DNA polymerase (e.g., SURESTART® Taq DNA polymerase; Stratagene, La Jolla, Calif.). In this embodiment, it is preferable to remove the modified polynucleotide template prior to amplification with the second polymerase, particularly since Taq polymerase recognizes uracil bases. Agents and methods suitable for the removal of the modified polynucleotide template are known in the art and include treating the sample after the first primer extension reaction but before amplification with the second polymerase with Uracil DNA Glycosylase (UDG). UDG is available from New England Biolabs, Beverly, Mass. UDG cleaves the uracil base from the phosphodiester backbone of uracil-containing DNA, but has no effect on natural (i.e., thymine-containing) DNA. The resulting apyrimidinic sites block replication by DNA polymerases, and are very labile to acid/base hydrolysis. Therefore, treating the sample with UDG after the first primer extension reaction but before amplification with the Taq polymerase will remove any remaining modified polynucleotide template and thus help to minimize any background signal.

In a preferred embodiment, the first polymerase is Klenow or T4 polymerase. The first polymerase and the binding molecule, for example an antibody, can associate with each other as a fusion protein or they may be linked via a chemical linker. Suitable chemical linkers include biotin-streptavidin interactions. In still another embodiment, the first polymerase is coupled to the antibody via an antibody binding molecule (e.g., protein A or protein G or biotin, avidin, or streptavidin).

In a preferred embodiment, the binding molecule is a biotinylated antibody and the first polymerase is fused to streptavidin or avidin.

In a preferred embodiment, a method of detecting an analyte in a sample is provided. The method comprises
    binding of a biotinylated antibody to an analyte, wherein the analyte is immobilized on a surface;
    washing the surface to remove unbound antibody;
    incubating the surface with a fusion protein comprising a first polymerase fused to streptavidin under conditions permitting coupling between the biotin on the antibody and the streptavidin in the fusion protein and the formation of an immobilized analyte/biotinylated antibody/fusion protein complex;
    washing the surface to remove unbound fusion protein;
    incubating the immobilized analyte/biotinylated antibody/fusion protein complex with a modified polynucleotide template that comprises one or more modified nucleotides, such as deoxyuracil or 2'-O-methyl modified nucleotides, four deoxytriphosphates, and a first primer that binds to the modified polynucleotide template under conditions permitting the first polymerase to extend the first primer and synthesize a copy of the modified polynucleotide template without the one or more modified nucleotides ("unmodified copy");
    transferring an aliquot of the incubation reaction comprising the unmodified copy into a new reaction vessel;
    amplifying the unmodified copy with a second polymerase, such as Pfu DNA polymerase, that cannot amplify the modified polynucleotide template; and
    detecting an amplification product, wherein detection of the amplification product is indicative of the presence or amount of analyte in the sample.

In another aspect, the invention is directed to a method of detecting an analyte in a sample by forming a reaction mixture which includes a binding molecule, such as an antibody, coupled to a first polymerase, such as a Klenow or T4 polymerase, a modified polynucleotide template, a first primer complementary to the modified polynucleotide template, a second polymerase, such as Pfu polymerase, and a second primer complementary to an unmodified copy of the modified polynucleotide template. The modified polynucleotide template includes one or more modified nucleotides, such as deoxyuracil or 2'-O-methyl modifications. The reaction mixture is incubated so as to permit binding of the binding molecule to the analyte, annealing of the first primer to the modified polynucleotide template and extension of the first primer by the first polymerase. Extension of the first primer produces a copy of the modified polynucleotide template that does not contain any of the modified nucleotides ("unmodified copy"). The unmodified copy is detected by annealing the second primer to the unmodified copy and extending the primer with the second polymerase. The second polymerase cannot amplify the modified polynucleotide template but can amplify the unmodified copy generated by the first polymerase. Detection of the unmodified copy is indicative of the presence or amount of analyte in the sample.

In certain aspects where the primer used to extend the polynucleotide template has a 3' flap, the binding molecule, such as an antibody, is coupled to a first polymerase having 3' exonuclease activity. The first polymerase can be any polymerase that has 3' nuclease activity such as Klenow (exo$^+$). The second polymerase can be any polymerase that does not have 3' nuclease activity such as Pfu (exo$^-$) DNA polymerase. The first polymerase and the antibody can associate with each other in the form of a fusion protein or they may be linked via a chemical linker. Suitable chemical linkers include biotin-streptavidin interactions. In still another embodiment, the first polymerase is coupled to the antibody via an antibody binding molecule (e.g., protein A or protein G).

The polynucleotide template (modified or unmodified) is preferably free in solution, however in some embodiments, including both solid phase and solution based embodiments, it is contemplated that it is coupled to an additional antibody or other moiety, such as streptavidin, which can interact with a biotinylated detector molecule, such as an antibody. In this embodiment, the copy of the polynucleotide template is only synthesized when the first and second antibody (or other moiety) bind within close proximity to one another (e.g., same analyte) therefore allowing the first polymerase and polynucleotide template to interact.

Detection of the replicated polynucleotide template can be performed by numerous methods known in the art, including a real-time PCR detection assays (e.g. MX3005P real-time PCR from Stratagene) using art-available detection reagents, such as TAQMAN® (Roche Molecular Systems Inc., Alameda, Calif.) probe or SYBR® (Molecular Probes, Eugene, Oreg.) Green dye. Suitable detection assays also include cleavage reactions. For example, the detection reaction may further include a labeled probe that anneals downstream of the second primer. In this embodiment, the second primer is extended so as to cleave a labeled downstream probe in a nucleic acid cleavage reaction (e.g., TAQMAN® (Roche Molecular Systems Inc., Alameda, Calif.) detection assay). Alternatively, the detection step may employ the direct detection of the extension product from the second primer. In this embodiment, the amplification product of the extended second primer may be detected by gel electrophoresis and visualization. The presence of the amplification product is indicative of the presence of the analyte in the sample.

Compositions for use in the methods and kits disclosed herein are provided. In one aspect, the composition comprises an antibody coupled to a first polymerase or portion thereof. In one embodiment, the antibody is fused with the first polymerase or portion thereof. In a preferred embodiment, the antibody is coupled to the polymerase or portion thereof by a biotin/avidin interaction. For example, a biotinylated antibody may be used with a fusion protein comprising the first polymerase or a portion thereof linked to streptavidin or avidin. The compositions can be combined with at least one other substance that is suitable for use in conjunction with practicing the methods described herein. Suitable substances include those that may be caused to contact the binding molecule or the first polymerase without adversely affecting their ability to perform as desired in a method disclosed herein. Alternatively or in addition, compositions may comprise a binding molecule and one or more substances to which the molecule specifically binds (e.g., an antigen to be detected) or one or more substances that interact with the polymerase moiety (e.g., a modified polynucleotide template). In another aspect the composition comprises a binding molecule other than an antibody, such as Protein A, G, or L, or biotin, avidin, or streptavidin, coupled to a polymerase moiety, which can be combined with at least one other substance that is suitable for use in conjunction with practicing the methods described herein. Compositions may be found in liquid or solid form, such as, for example, in a lyophilized dried powder or in an aqueous mixture. Use of the composition in a binding and detection assay is accordingly provided.

In one aspect of the split polymerase system, the polymerase is Klenow and the first portion of the first polymerase has the amino acid sequence of SEQ ID NO: 2 and the second portion of the first polymerase has the amino acid sequence of SEQ ID NO: 3. As disclosed in the Entrez Structure database (available from the National Center for Biotechnology Information ("NCBI") website), Klenow belongs to the DNA polymerase A superfamily and shares a conserved polymerase domain spanning from about amino acid 225 to amino acid 605 of SEQ ID NO:1; see also, Villbrandt et al., Protein Eng. 2000 13(9):645-54, the disclosure of which is hereby incorporated by reference. Using the known domain structure, one of skill in the art could readily construct other versions of a split Klenow polymerase, as illustrated, for example, in FIG. 7. As the polymerase domain of Klenow is known in the art, one of skill in the art could readily make substitutions or deletions to the sequences of SEQ ID NO:2 and SEQ ID NO:3 (or other Klenow fragments, such as those depicted in FIG. 7) without affecting the polymerase activity of the polymerase complex formed when the two portions associate. Therefore, in another aspect, the first portion of the first polymerase has at least 95%, at least 98%, or at least 99% identity with the amino acid sequence of SEQ ID NO:2 (or whatever other Klenow fragment is used) and the second portion of the first polymerase has at least 95% at least 98%, or at least 99% identity with the amino acid sequence of SEQ ID NO:3 (or whatever other Klenow fragment is used), so long as the first and second portions of the first polymerase form a functional polymerase complex when they interact. Split polymerases other than Klenow can be constructed by those skilled in the art. Three-dimensional structures of Klenow and other polymerases are available from public databases, such as the Structure database at the NCBI web site. Positioning a split point in a non-structured region that separates structural domains is preferred. Reconstitution of the polymerase activity can be facilitated by any approach that brings the portions of the polymerase into close proximity. The binding moiety can be a monoclonal or polyclonal antibody, lectin, cell surface receptor, receptor ligand, peptide, carbohydrate, aptamer, biotin, streptavidin, avidin, protein A or protein G. In a preferred embodiment two complementary portions of Klenow are provided with streptavidin tags that can bind to biotins on the same antibody or to the biotins on different antibodies that are in proximity to each other on the analyte, In another aspect, a spacer molecule separates the binding molecule from the first polymerase or the first and second binding moiety from the first and second portion of the first polymerase, respectively. The spacer molecule may be comprised of any substance or combination of substances. Typically, however, it will be comprised of a polypeptide or a polynucleotide. In one embodiment, the spacer molecule is a polypeptide linker comprising small amino acids, such as glycine, serine, alanine, and threonine. In another embodiment, a naturally occurring flexible unstructured region can be used. Such regions can be selected from abundantly expressed proteins, for example from L7/L12 ribosomal protein (Bocharov et al., "From structure and dynamics of protein L7/L12 to molecular switching in ribosome," J. Biol. Chem., 2004 279(17):17697-706). Many unstructured regions are known to those skilled in the art and are available from protein structures in databases, for example from Entrez Structure NCBI database. Furthermore, unstructured regions can be predicted in proteins by bioinformatics methods, for example using a Scooby-Domain method (Pang C N et al., "Identifying foldable regions in protein sequence from the hydrophobic signal," Nucleic Acids Res., 2008 36(2):578-88).

Separating the binding molecule from the polymerase by using a spacer molecule is useful, for example, in providing more flexibility to the fusion proteins and facilitating unhindered functioning of the binding and polymerase domains.

The spacer molecule also helps to promote the interaction of the split polymerase moieties (e.g., N- and C-terminal portions) and reconstitution of a functional polymerase complex. As set forth in Examples 6-9, reconstitution of polymerase activity is facilitated by the binding of the streptavidin-split polymerase moieties to biotinylated antibodies. Binding to the biotinylated antibodies brings the N- and C-terminal portions of the polymerase into close proximity and promotes reconstitution of polymerase activity.

Due to the random position of biotin molecules in biotinylated antibodies, all of the streptavidin-biotin binding events will not necessarily lead to the reconstitution of polymerase activity. For example, some biotin molecules could be too distant from each other. Alternatively, biotin molecules could bind Streptavidin-polymerase N- and Streptavidin-polymerase C-portions facing away from each other. Using a spacer molecule helps to facilitate the reconstitution of polymerase activity, for example, by reducing steric hindrance between the split polymerase portions, particularly when the streptavidin-split polymerase fusion proteins are not facing each other or are bound to biotin molecules that are not in close proximity.

Any of the detection methods described herein may be performed in a single reaction vessel or in two or more reaction vessels (e.g., antibody binding to analyte and synthesis of an unmodified copy or template for amplification in a first reaction vessel and detection of the amplified unmodified copy or template in a second reaction vessel).

Any of the detection methods described herein may be adapted so as to be performed in a solution based assay (e.g., without a capture antibody and solid support). In these embodiments, the method generally utilizes two detector antibodies, the first operatively coupled to a polynucleotide template and the second coupled to a first nucleic acid polymerase. Similarly, in the split polymerase system, the method generally uses two detector antibodies, each independently coupled to a first and second portion of the first polymerase, respectively, and the modified polynucleotide template provided in solution. The modified polynucleotide template may be coupled to a detector antibody or to a different binding moiety, such as streptavidin, which can interact with biotinylated detector antibodies. The antibodies are designed so as to bind within close proximity to one another so as to allow the polynucleotide template and first nucleic acid polymerase to interact so as to form a template for amplification, or, in the split polymerase system, to facilitate reconstitution of polymerase activity. Such assays are described in U.S. application Ser. No. 11/546,695, filed Oct. 11, 2006 and herein incorporated by reference in its entirety.

The compositions and methods disclosed herein have broad applicability in the biotechnology and medical fields. They are useful not only for research purposes, but are also advantageously applied to the medical, veterinarian, forensic, environmental, and food testing arts as diagnostic reagents and assays. Thus, in embodiments, the present invention provides diagnostic methods for detecting substances of interest from a sample, where detection of the substances is indicative of particular diseases or disorders. For example, a method may be a diagnostic method for diagnosing cancer in a patient, where the method includes detection of a cancer-specific antigen. Likewise, for example, a method may be a diagnostic method for diagnosing a metabolic disorder, such as diabetes, by detection of a known marker of the disorder. Many markers for diseases and disorders in humans and other animals are known, and any such marker may be used within the context of a diagnostic assay according to the methods disclosed herein. It is to be noted that the marker need not be one that is 100% correlated with a particular disease or disorder, but rather may simply be known as associated with a disease or disorder in some humans or animals affected by the disease or disorder. Furthermore, it is to be understood that the marker need not be a causative agent of the disease or disorder, but rather may be any marker that is know to be associated (by its presence, absence, or level) with a disease or disorder.

The methods disclosed herein may also be used to prognose the outcome of a disease or disorder, or follow a treatment regimen for a disease or disorder. More specifically, the compositions and methods can be used to follow the presence and level of markers for diseases and disorders over time by repetition of detection assays on multiple samples taken over time. Where the presence, absence, or level of a marker is indicative of the likelihood of recovery from the disease or disorder (or the severity of the disease or disorder, etc.), the assays of the present invention can be used to predict the outcome or follow the development of the disease or disorder.

In view of the uses discussed above, in a further aspect, kits comprising the compositions of the invention are provided. In general, the kits comprise a polymerase or a first and second portion thereof coupled to a binding molecule or moiety, such as an antibody, in at least one container, in combination with packaging materials for storage and shipment of the container. Alternatively, the kits comprise a polymerase or a first and second portion thereof coupled to streptavidin or avidin in at least one container, in combination with packaging materials for storage and shipment of the container. The polymerase or portions thereof may be supplied as a pure substance or as part of a composition. Additional components may be supplied in the kit, including, but not limited to, other reagents and supplies for practicing a method of the invention, including a polynucleotide template (modified or unmodified), one or more primer, and/or a second polymerase that either cannot amplify a modified polynucleotide template or that substantially lacks 3' exonuclease activity. Those of skill in the art are aware of the various supplies and substances typically included in kits for detecting substances of interest, and any of those supplies and substances may be included in a kit according to the present invention. For example, a kit may comprise one or more solid substrates for performing a method of the invention, which can, in embodiments, be pre-bound by a capture molecule (e.g., an antibody) that can specifically bind to the analyte of interest and/or a detection reaction vessel for a catalytic reaction (e.g. a PCR reaction tube). The kit may also or alternatively contain one or more containers (e.g., bottles) holding binding solutions or wash solutions.

Detection Assays Utilizing a Modified Polynucleotide Template

FIG. 1A illustrates a solid-phase embodiment utilizing a modified polynucleotide template and a first DNA polymerase capable of copying a modified polynucleotide template (e.g., Klenow). In this embodiment, a test sample containing the analyte is first incubated with an immobilized capture antibody and then with a detector antibody that is coupled to a first nucleic acid polymerase. Alternatively, the analyte is directly bound to the well and no capture antibody is necessary.

Following the incubation, in the solid-phase assays utilizing a capture antibody, the wells are washed with a wash buffer.

An extension reaction mixture is then added to the wells containing the capture antibody-analyte-detector antibody-polymerase complex and incubated (e.g., for 30 minutes at room temperature). The extension reaction mixture includes a modified polynucleotide template, as described herein, and a reverse primer that is complementary to a portion of the modified polynucleotide template. During the incubation the primer anneals to the modified polynucleotide template and is extended by the first nucleic acid polymerase so as to form an unmodified copy of the modified polynucleotide template. The unmodified copy is then utilized in a detection reaction.

The detection reaction may be performed in the same or, preferably, a different reaction vessel as the binding/extension reaction. For example, an aliquot of the reaction mixture having the unmodified copy may be transferred to a corresponding well of a 96-well PCR plate. In this step, the unmodified copy is reacted with a detection reagent (e.g., TAQMAN® (Roche Molecular Systems Inc., Alameda, Calif.) probe, SYBR® (Molecular Probes, Eugene, Oreg.) Green dye, molecular beacon probe), a second nucleic acid polymerase that is incapable of replicating a modified polynucleotide template and one or more primers, such as a reverse and forward primer. The detection reaction mixture is subjected to reaction conditions which allow annealing of the primers, amplification of the unmodified copy and detection of the amplified unmodified copy. For example, in one embodiment the detection reaction is run in a real-time PCR device that is programmed with the appropriate times and temperatures necessary for amplification and detection. For example in a detection reaction utilizing SYBR® (Molecular Probes, Eugene, Oreg.) green, a MX3005P real-time PCR device may be utilized with the program corresponding to a SYBR® (Molecular Probes, Eugene, Oreg.) Green detection assay with dissociation curve and a 2-step cycling parameter of 95° C. for 10 minutes, followed by 40 cycles of 95° C. for 15 seconds, and 63° C. for 45 seconds. Other means of real-time PCR detection are well known in the art (e.g., TAQMAN® (Roche Molecular Systems Inc., Alameda, Calif.) detection assay, and molecular beacon detection assays) and can be adapted for use in the present embodiment. The detected signal can then be used to determine the concentration of the analyte in the sample.

Figure 1B:
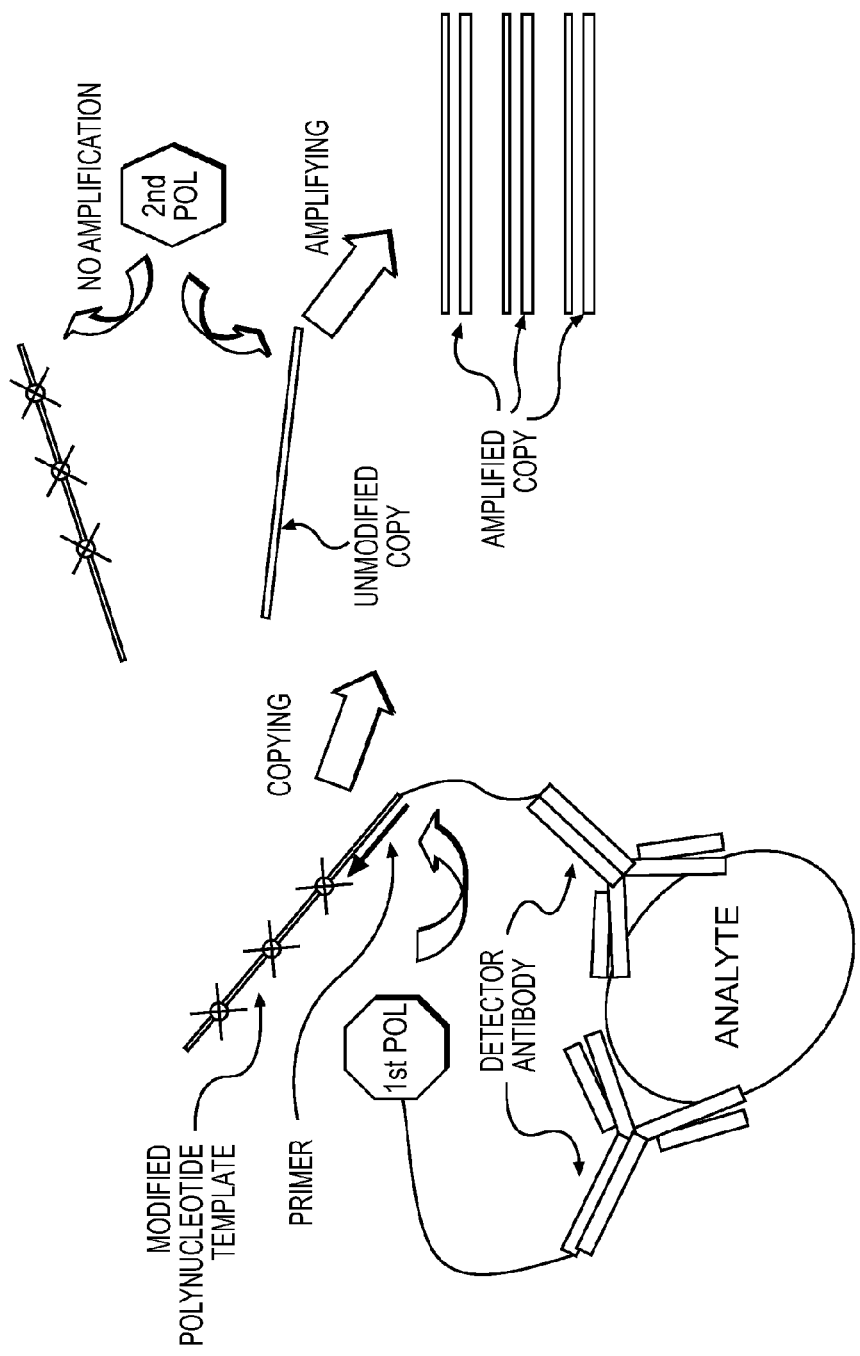
FIG. 1B illustrates one embodiment of a non-solid phase detection assay (use of a first antibody coupled to a polymerase and a second antibody coupled to a template nucleic acid) utilizing a modified polynucleotide template.

In another embodiment, an analyte, a detector antibody coupled to a first polymerase, and another antibody coupled to a modified polynucleotide template are free in solution (FIG. 1B). The detector antibody may be coupled to the first nucleic acid polymerase before they are added to the reaction mixture or may be coupled during the incubation with the analyte (e.g., biotin labeled detector antibody and added streptavidin-Klenow). Alternatively, the first nucleic acid polymerase may be bound to the detector antibody via an intermediate (e.g., second antibody) which is coupled to the first nucleic acid polymerase and binds to the detector antibody. When the analyte is free in solution, coupling the modified polynucleotide template to an antibody helps to bring the modified polynucleotide template and the first polymerase into close proximity upon binding of the antibody to the analyte. This in turn facilitates the interaction between the first polymerase and the modified polynucleotide template, helping to speed up the rate at which the first polymerase synthesizes an unmodified copy of the modified polynucleotide template. In this solution-based embodiment, the extension and detection reactions are the same as described for the solid-phase embodiment.

Detection Assays Utilizing a Primer with a 3' Flap

Figure 2A:
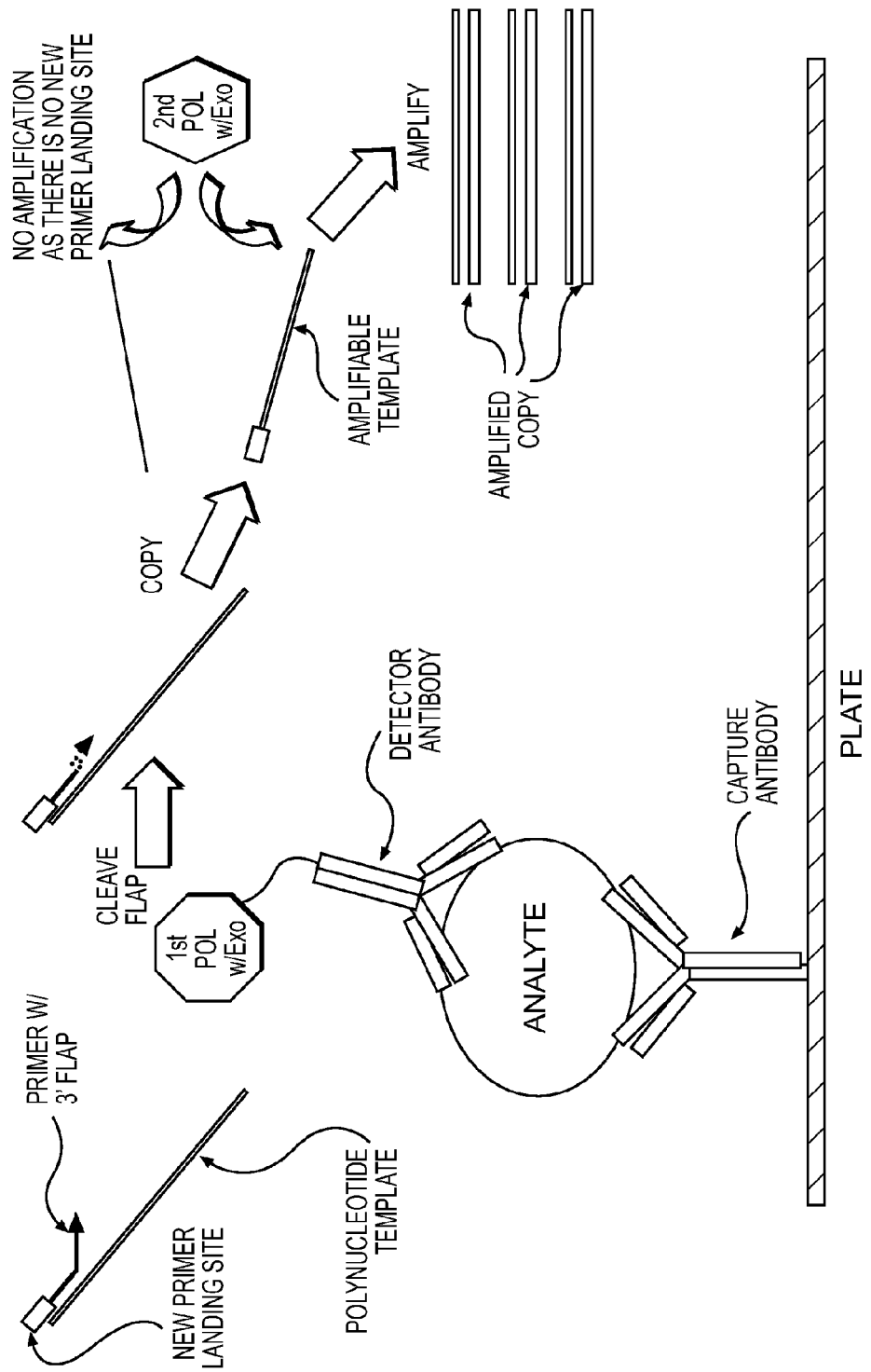
FIG. 2A illustrates an embodiment of a solid-phase detection assay utilizing a primer with a 3' flap and a 5' region that introduces a new primer binding site. The 3' exonuclease activity of the first polymerase cleaves or otherwise removes the 3' flap, and the first polymerase extends the primer to synthesize a copy of the polynucleotide template. The primer may be designed to have a lower $T_m$ than the annealing temperature for the primers used in the amplification/detection step. The polynucleotide template can be modified or unmodified.

FIG. 2A illustrates one embodiment utilizing a polynucleotide template and a first DNA polymerase with 3' exonuclease activity (Klenow (exo$^+$)). In some embodiments, the first polymerase does not have 3' nuclease activity as the 3' nuclease activity is supplied by a separate enzyme (e.g., different polymerase or a nuclease that does not necessarily have polymerase activity).

Figure 2B:
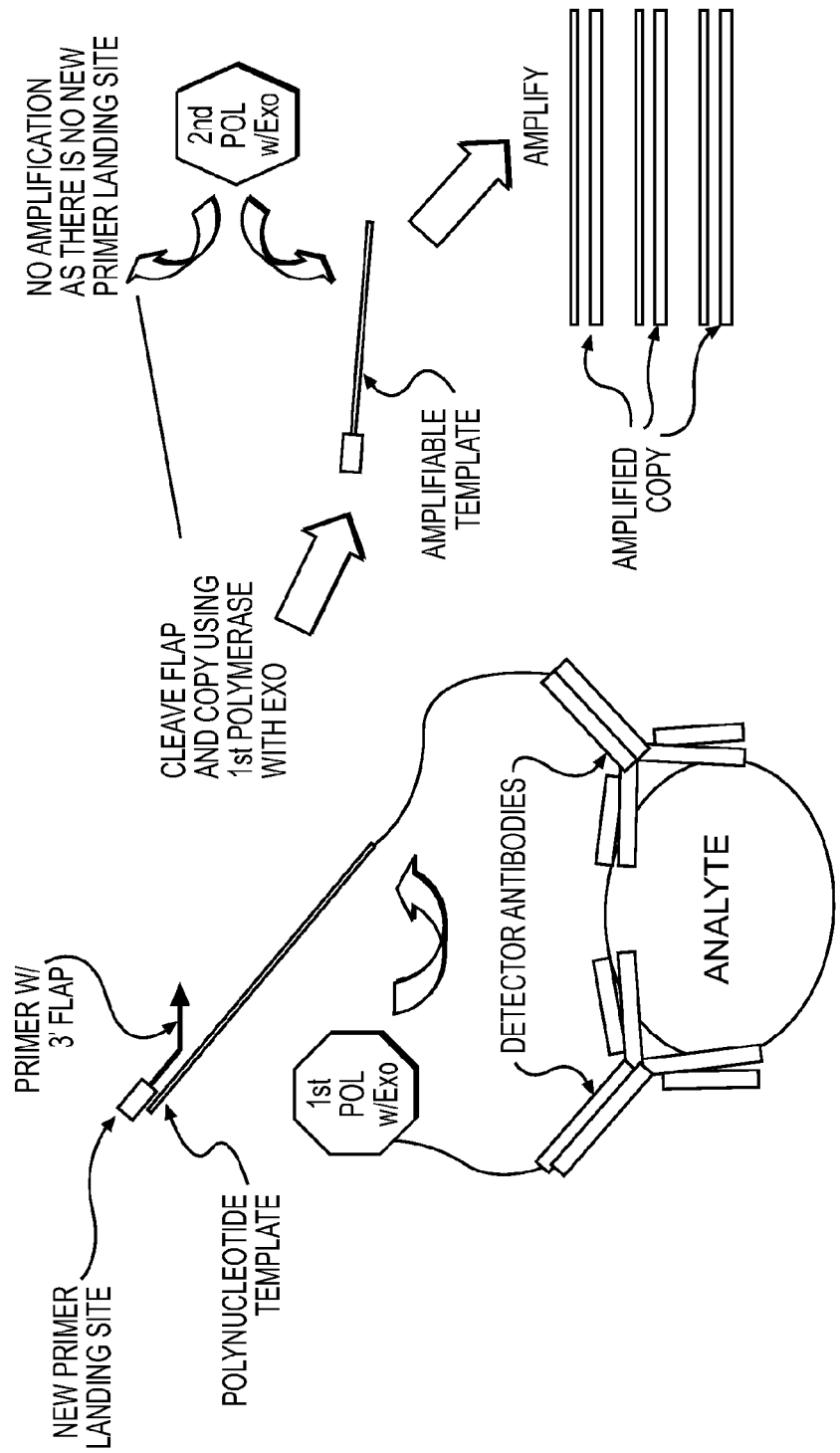
FIG. 2B illustrates an embodiment of a non-solid phase detection assay (use of a first antibody coupled to a polymerase and a second antibody coupled to a template nucleic acid) utilizing a primer with a 3' flap and a 5' region that introduces a new primer binding site. The 3' exonuclease activity of the first polymerase cleaves or otherwise removes the 3' flap, and the first polymerase extends the primer to synthesize a copy of the polynucleotide template. The primer may be designed to have a lower $T_m$ than the annealing temperature for the primers used in the amplification/detection step. The polynucleotide template can be modified or unmodified.

The test sample containing the analyte is first reacted with an immobilized capture antibody and then with a detector antibody that is coupled to a first nucleic acid polymerase. Alternatively, the analyte is directly bound to the well and no capture antibody is utilized. In another embodiment, an analyte, a detector antibody coupled to a first polymerase, and another antibody coupled to a polynucleotide template are free in solution and not bound to a solid support (e.g., solution-based assay, FIG. 2B). The detector antibody may be coupled to the first nucleic acid polymerase before it is added to the reaction mixture or may be coupled during the incubation with the analyte (e.g., biotin labeled detector antibody and added streptavidin-Klenow). Alternatively, the first nucleic acid polymerase may be bound to the detector antibody via an intermediate (e.g., second antibody) which is coupled to the first nucleic acid polymerase and binds to the detector antibody. The reaction mixture is allowed to incubate for a sufficient period of time at an appropriate temperature (e.g., 30 minutes at room temperature) so as to allow binding of the capture antibody and/or detector antibody to the analyte. After the incubation, in the solid-phase assay, the wells are washed with a wash buffer.

An extension reaction mixture is then added to the wells and incubated (e.g., for 30 minutes at room temperature). The extension reaction mixture includes a polynucleotide template, as described herein, and an extension primer with a 3' flap and a 5' region that introduces a new primer binding site upon extension. During the incubation step the primer anneals to the polynucleotide template so as to form a 3' non-complementary flap. The 3' flap is then cleaved by the first nucleic acid polymerase and extended so as to form a template for amplification comprising the new primer binding site introduced by the extension primer. In some embodiments, the first polymerase does not have 3' nuclease activity and the 3' flap is cleaved by a different enzyme (e.g., different polymerase or a nuclease that does not necessarily have polymerase activity). The template for amplification is then utilized in a detection reaction with and a second DNA polymerase substantially lacking 3' exonuclease activity, such as Pfu (exo$^-$) DNA polymerase.

The detection reaction may be performed in the same or, preferably, a separate reaction vessel as the binding/extension reaction. For example, an aliquot of the reaction mixture having the template for amplification may be transferred to a corresponding well of a 96-well PCR plate. In this step, the template for amplification is reacted with a detection reagent (e.g., TAQMAN® (Roche Molecular Systems Inc., Alameda, Calif.) probe, SYBR® (Molecular Probes, Eugene, Oreg.) Green dye), a first and second primer, one of which anneals to the new primer binding site introduced by the extension primer, and a second nucleic acid polymerase substantially lacking 3' exonuclease activity. The detection reaction mixture is subjected to reaction conditions which allow the annealing of the primers, amplification of the template for amplification and detection of the amplified template. For example, in one embodiment the detection reaction is run in a real-time PCR device that is programmed with the appropriate times and temperatures necessary for amplification and detection. For example a MX3005P real-time PCR device may be utilized with the program corresponding to a SYBR® (Molecular Probes, Eugene, Oreg.) Green detection assay with dissociation curve and a 2-step cycling parameter of 95° C. for 10 minutes, followed by 40 cycles of 95° C. for 15 seconds, and 63° C. for 45 seconds. Other means of real-time PCR detection are well known in the art (e.g., TAQMAN® (Roche Molecular Systems Inc., Alameda, Calif.) and molecular beacon detection assays) and can be adapted for use in the present embodiment. The detected signal can then be used to determine the concentration of the analyte in the sample.

Detection Assays Using a Split Polymerase and Modified Polynucleotide Template

Figure 6:
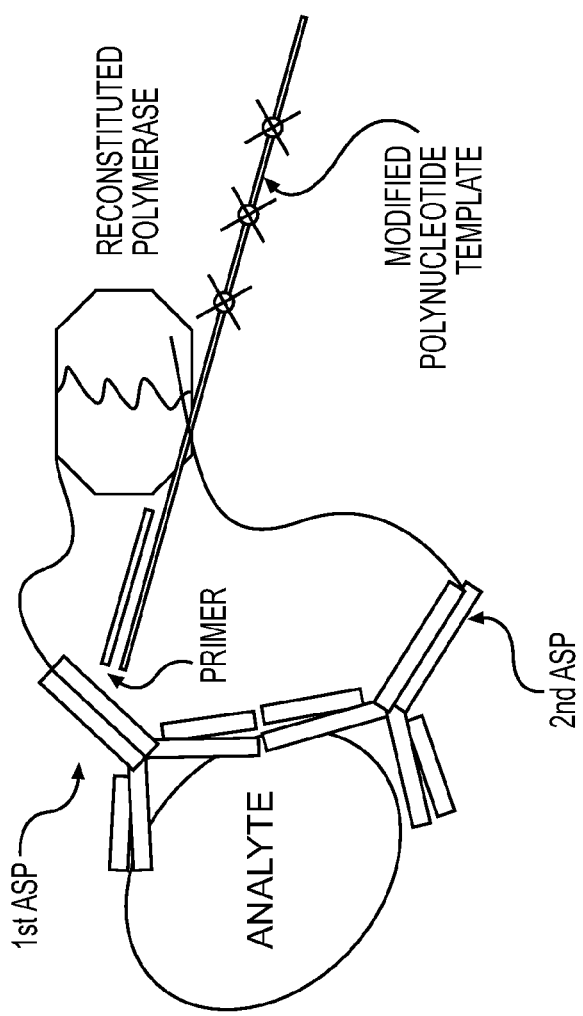
FIG. 6 illustrates one embodiment using a first antibody coupled to a first portion of Klenow and a second antibody coupled to a second portion of Klenow. In this embodiment, the split portions of Klenow interact to form a functional polymerase complex upon binding of two ASPs in close proximity.

FIG. 6 illustrates one embodiment utilizing a modified polynucleotide template, a first analyte specific probe having a first binding moiety and a first portion of a first polymerase, and a second analyte specific probe having a second binding moiety and a second portion of the first polymerase (e.g., Klenow).

In this embodiment, a test sample containing the analyte is first reacted with the first and second analyte specific probes in a binding reaction. In some embodiments, a capture antibody bound to a solid support is also present. The first and second binding moieties are coupled to the first and second polymerase portions respectively. The binding moieties may be coupled to the polymerase portions in many different ways, including, but not limited to direct linking as an antibody/polymerase fusion protein, linked via streptavidin-biotin interactions or Protein A or Protein G. When the first and second portions of the first polymerase are separated they substantially lack synthetic activity. However, when the first and second portions of the first polymerase are brought in close proximity to each other they interact so as to form a functional first polymerase complex having synthetic activity.

After binding of the ASPs and interaction of the first and second portions of the first polymerase an extension reaction proceeds. In addition to the reagents listed above, the extension reaction further includes a modified polynucleotide template and one or more additional primers that are complementary to a portion of the modified polynucleotide template. The reaction mixture is incubated (e.g., for 30 minutes at room temperature) so as to permit primer annealing and extension of the primers by the first polymerase complex, so as to form an unmodified copy of the modified polynucleotide template. The unmodified copy is then utilized in a detection reaction with a second polymerase that is incapable of replicating a modified polynucleotide template as discussed above in reference to the solid phase embodiment associated with FIG. 1A.

Analytes

The methods, compositions, and kits may be used to detect a wide variety of analytes. The binding sites for the binding molecule or each ASP can be the same or different. An analyte can be a single molecule, molecular complex, an organism or virus containing multiple reagent binding sites. Since the length of the oligonucleotides encoding the binding molecules or the ASPs can be constructed to span varying molecular distances, binding sites need not be on the same molecule. However, they may be on separate, but closely positioned, molecules. For example, the multiple binding epitopes of an organism, such as a virus, bacteria or cell can be targeted by the methods disclosed herein. In one aspect, the analyte is a protein, oligonucleotide, cell surface receptor, or receptor ligand.

Binding Molecules and Moieties

The methods disclosed herein may be adapted for the detection of any analyte by simply altering the binding molecule or binding moiety (also referred to as the capture molecule and/or the detector molecule) used in the method (e.g., the capture antibody attached to the solid support and the detector antibody coupled to a polymerase or a portion thereof) such that the capture and detector molecules utilized specifically recognize and bind the analyte for which the method is being used. In some embodiments, the analyte may be directly bound to the solid support so that a capture antibody is not necessary. In other embodiments, a capture antibody binds the analyte, an unlabeled intermediate antibody binds the analyte and a detector antibody binds the intermediate antibody.

In other embodiments, the assay is performed as a solution-phase reaction (e.g., without a capture antibody and solid-support). In these embodiments, the method generally utilizes a first detector antibody operatively coupled to a modified polynucleotide template and a second detector antibody coupled to a first nucleic acid polymerase or, alternatively, a second and third detector antibody coupled to a first and second portion of the first nucleic acid polymerase. The antibodies are designed so as to bind within close proximity to one another so as to allow the polynucleotide template and first nucleic acid polymerase to interact so as to form a template for amplification (e.g., an unmodified copy of the modified polynucleotide template). Such assays are described in U.S. application Ser. No. 11/546,695, filed Oct. 11, 2006 and herein incorporated by reference in its entirety.

The capture molecule and the detector molecule may recognize and bind the same portion or epitope of the analyte under investigation (e.g., multivalent analyte). Alternatively, the capture molecule and the detector molecule recognize and bind different portions or epitopes of the analyte. In some embodiments, the capture molecule and detector molecule may not bind to the same analyte but two different analytes that interact to form a complex. For example, a capture antibody may be specific for and bind to a receptor protein and the detector antibody may be specific for and bind to a ligand of the receptor such that the capture molecule, receptor protein, ligand and detector antibody form a complex.

The binding moieties are designed so as to bind within close proximity to one another so as to allow the first and second portions of the first nucleic acid polymerase to interact so as to form a template for amplification.

Preferably, the capture and analyte-binding detector molecules or binding moieties are monoclonal, polyclonal, or phage derived antibodies, or antibody fragments. More preferably, the capture and detector molecules or binding moieties are monoclonal antibodies.

Antibodies, whether they are polyclonal, a monoclonal or an immunoreactive fragment thereof, can be produced by customary methods familiar to those skilled in the art. Conventional monoclonal and polyclonal antibodies are of use and represent a preferred type binding molecule. Established methods of antibody preparation therefore can be employed for preparation of the immune type binding molecules. Suitable methods of antibody preparation and purification for the immune type binding moieties are described in Harlow, Ed and Lane, D in Antibodies a Laboratory Manual, Cold Spring Harbor Laboratory Press, Cold Spring Harbor, N.Y. (1988). Furthermore, the assays described herein can be used with currently available commercially available antibodies.

"Polyclonal antibodies" are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

Any method known in the art for generating monoclonal antibodies is contemplated, for example by in vitro generation with phage display technology and in vivo generation by immunizing animals, such as mice. These methods include the immunological methods described by Kohler and Milstein (Nature 256, 495-497 (1975)) and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1995)); as well as by the recombinant DNA method described by Huse et al. (Science 246, 1275-1281 (1989)). Standard recombinant DNA techniques are described in Sambrook et al. ("Molecular Cloning," Second Edition, Cold Spring Harbor Laboratory Press (1987)) and Ausubel ("Current Protocols in Molecular Biology," Green Publishing Associates/Wiley-Interscience, New York (1990)). Each of these methods is incorporated herein by reference.

The capture molecule and the detector molecule are not limited to intact antibodies, but encompass other binding molecules such as antibody fragments and recombinant fusion proteins comprising an antibody fragment.

Methods of producing chimerized, humanized, and single-chain antibodies as well as fragments thereof are disclosed in PCT Application WO 93/21319, European Patent Application No. 239,400; PCT Application WO 89/09622; European Patent Application 338,745; and European Patent Application EP 332,424. Each of these applications is incorporated herein by reference.

In addition, techniques developed for the production of "chimeric antibodies" (Morrison, et al., Proc. Natl. Acad. Sci., 81:6851-6855 (1984); Takeda, et al., Nature, 314:452-54 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Alternatively, techniques described for the production of single chain antibodies (U.S. Pat. No. 4,946,778; Bird, Science 242:423-26 (1988); Huston, et al., Proc. Natl. Acad. Sci. USA, 85:5879-83 (1988); and Ward, et al., Nature, 334:544-46 (1989)) can be adapted to produce gene-single chain antibodies. Single chain antibodies are typically formed by linking the heavy and light chain fragments of the Fv region via an amino acid bridge, resulting in a single chain polypeptide.

Non-immune binding-molecules are also contemplated for use as capture or detector molecules. These molecules include systems, wherein, two components share a natural affinity for each other, but are not antigen/antibody-like pairs. Exemplary non-immune binding-moieties include biotin/avidin or biotin/streptavidin, folic acid-folate binding protein, vitamin B12/intrinsic factor, complementary probe nucleic acids, Proteins A, G, immunoglobulins, hetero- and homodimeric polypeptide complexes, etc. Also included are non-immune binding-pairs that form a covalent bond with each other.

One could also use non-antibody protein receptors or non-protein receptors such as polynucleic acid aptamers. Polynucleic acid aptamers are typically RNA oligonucleotides which may act to selectively bind proteins, much in the same manner as a receptor or antibody (Conrad et al., Methods Enzymol. (1996), 267 (Combinatorial Chemistry), 336-367). Theses aptamers will be suitable as binding molecules or binding moieties.

By the terms "specifically binding" and "specific binding" as used herein is meant that an antibody or other binding molecule or binding moiety binds to a target such as an antigen, ligand or analyte, with greater affinity than it binds to other molecules under the specified conditions of the present invention. Antibodies or antibody fragments, as known in the art, are polypeptide molecules that contain regions that can bind other molecules, such as antigens. In various embodiments, "specifically binding" may mean that an antibody or other biological molecule, binds to a target molecule with at least about an affinity of $10^{-6}$-$10^{-10}$/M, more preferably they will have an affinity of at least $10^{-8}$/M, most preferably they will have an affinity at least $10^{-9}$/M.

Polymerases

DNA polymerases are well known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In E. coli, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Similarly, RNA polymerases typically include eukaryotic RNA polymerases I, II, and III, and bacterial RNA polymerases as well as phage and viral polymerases. RNA polymerases can be DNA-dependent and RNA-dependent.

The methods, compositions, and kits described herein can utilize at least four classes of polymerases: (1) polymerases lacking 3' nuclease activity; (2) polymerases having 3' nuclease activity; (3) polymerases capable of replicating a modified polynucleotide template; and (4) polymerases incapable of replicating a modified polynucleotide template. Nucleic acid polymerases useful in certain embodiments substantially lack 3' to 5' nuclease activity and include but are not limited to exo⁻ Pfu DNA polymerase (a mutant form of Pfu DNA polymerase that substantially lacks 3' to 5' exonuclease activity, Cline et al., 1996, Nucleic Acids Research, 24: 3546; U.S. Pat. No. 5,556,772; commercially available from Stratagene, La Jolla, Calif. Catalogue #600163), exo⁻ Tma DNA polymerase (a mutant form of Tma DNA polymerase that substantially lacks 3' to 5' exonuclease activity), exo⁻ Tli DNA polymerase (a mutant form of Tli DNA polymerase that substantially lacks 3' to 5' exonuclease activity New England Biolabs, (Cat #257)), exo⁻ E. coli DNA polymerase (a mutant form of E. coli DNA polymerase that substantially lacks 3' to 5' exonuclease activity) exo Klenow fragment of E. coli DNA polymerase I (Stratagene, Cat #600069), exo⁻ T7 DNA polymerase (a mutant form of T7 DNA polymerase that substantially lacks 3' to 5' exonuclease activity), exo⁻ KOD DNA polymerase (a mutant form of KOD DNA polymerase that substantially lacks 3' to 5' exonuclease activity), exo⁻ JDF-3 DNA polymerase (a mutant form of JDF-3 DNA polymerase that substantially lacks 3' to 5' exonuclease activity), exo⁻ PGB-D DNA polymerase (a mutant form of PGB-D DNA polymerase that substantially lacks 3' to 5' exonuclease activity) New England Biolabs, Cat. #259, Tth DNA polymerase, Taq DNA polymerase (e.g., Cat. Nos. 600131, 600132, 600139, Stratagene); UlTma (N-truncated) Thermatoga mar-

*tima* DNA polymerase; Klenow fragment of DNA polymerase I, 9° Nm DNA polymerase (discontinued product from New England Biolabs, Beverly, Mass.), "3'-5' exo reduced" mutant (Southworth et al., 1996, Proc. Natl. Acad. Sci. 935281) and Sequenase (USB, Cleveland, Ohio).

In specific embodiments, the first polymerase is Klenow coupled to a binding molecule, such as an antibody, or split into two moieties, each of which is coupled to a binding moiety, such as an antibody. Other Family A polymerases that act similarly to Klenow, e.g. complete *E. coli* DNA polymerase I, *Thermus aquaticus* DNA polymerase I, *Streptococcus pneumoniae* DNA polymerase I, T5 DNA polymerase, T7 DNA polymerase, Spo2 DNA polymerase or portions thereof can also be used. Mesophilic polymerases, such as Klenow, are preferred as the first polymerase because the extending step is typically performed at a temperature compatible with biological activity of other mesophilic proteins (antigen, antibodies) that could be present in the same mixture (e.g., a temperature ranging from about room temperature to about 37° C.). However, thermophilic polymerases, such as Taq can also be used, because they are active at mesophilic temperatures. In specific embodiments, Taq polymerase is split into a first and second portion each of which is linked to a binding moiety (e.g., antibody). In addition, the extension step with the first polymerase can be separated from analyte-binding step, and can be performed at any temperature that is optimal for the first polymerase reaction. *Thermus brockianus* polymerase, which is about 90% similar to Taq polymerase, as well as *Thermus flavus* polymerase, and *Thermus thermophilus* polymerase, having reverse transcriptase activity, may also be used. Additionally, less extremely thermophilic polymerases, such as the family A polymerase from *Bacillus stearothermophilus* can be used.

Family B polymerases such as *Pyrococcus* polymerases, e.g., Pfu polymerase, are useful as the second polymerase.

The activity of a polymerase can be measured using assays well known to those of skill in the art. For example, a processive enzymatic activity, such as a polymerase activity, can be measured by determining the amount of nucleic acid synthesized in a reaction, such as a polymerase chain reaction. In determining the relative efficiency of the enzyme, the amount of product obtained with a polymerase containing a sequence-non-specific double-stranded DNA binding domain can then be compared to the amount of product obtained with the normal polymerase enzyme.

A polymerase domain suitable for use in the methods, compositions, and kits disclosed herein can be the enzyme itself or the catalytic domain, e.g., *E. coli* DNA polymerase I, Klenow fragment of the *E. coli* DNA polymerase I ("Klenow") or a portion of Klenow with polymerase activity. The catalytic domain may include additional amino acids and/or may be a variant that contains amino acid substitutions, deletions or additions, but still retains enzymatic activity.

In one embodiment, the polymerase is divided into two portions that do not have substantial synthetic activity when separated but do have substantial synthetic activity when they interact to form a complex. The first polymerase may be split into two portions which are each coupled to a separate antibody. In one embodiment, the first polymerase is Klenow. In a preferred embodiment, the first portion of the first polymerase comprises amino acid residues 1-224 of SEQ ID NO:1 and the second portion of the first polymerase comprises amino acid residues 225-605 of SEQ ID NO:1.

The term "Klenow" refers to polypeptide polymorphic variants, alleles, mutants, and interspecies homologs that have an amino acid sequence that has greater than about 70%, 75%, 80%, 85%, 90%, preferably 91%, 92%, 93%, 94%, 95%, 96%, 97%, 98% or 99% or greater amino acid sequence identity, preferably over a region of at least about 25, 35, 50, or more amino acids, to the Klenow sequence of SEQ ID NO:1 and which display synthetic activity. In one embodiment, Klenow refers to a polypeptide sharing at least 95% amino acid identity with SEQ ID NO:1. SEQ ID NO:1 encompasses both Exo$^-$ Klenow, wherein the amino acid at position 1 is a methionine and the amino acids at positions 32 and 34 are alanine residues, and Exo$^+$ Klenow, wherein the amino acid at position 1 is a valine and the amino acids at positions 32 and 34 are aspartic acid and glutamic acid, respectively. The wild type sequences for Exo$^-$ Klenow and Exo$^+$ Klenow are publicly available as of the filing date of this application, for example, at accession numbers 1D8Y_A and 1KFD_A, respectively.

Suitable cleavage sites for constructing first and second portions of a first polymerase other than Klenow can be identified based on their sequence homology to Klenow. The test sequence can be compared and aligned with the Klenow sequence for maximum correspondence over a comparison window, or designated region as measured using one of the following sequence comparison algorithms or manual alignment and visual inspection. Percent amino acid identity can be determined by the default parameters of BLAST. For example, other Family A polymerases may be cleaved into a first portion which corresponds to amino acid residues 1-224 of SEQ ID NO:1 and into a second portion which corresponds to amino acid residues 225-605 of SEQ ID NO: 1. In yet another embodiment, the test polymerase is cleaved into two portions at an amino acid corresponding to any one of amino acids 199-310 of SEQ ID NO: 1.

As used herein, the term "corresponding to" refers to one or more amino acids in a test polypeptide sequence (Family A polymerase) that aligns with a given amino acid(s) in a reference polypeptide sequence (e.g., Klenow, SEQ ID NO: 1) when the first polypeptide and reference polypeptide sequences are aligned. Alignment is performed by one of skill in the art using software designed for this purpose, for example, BLASTP version 2.2.2 with the default parameters for that version.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l Acad. Sci. USA* 90:58735787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polymerase alignments for the Family A and Family B DNA polymerases are found in FIG. 1 of Braithwaite and Ito., *Nucleic Acids Res.* 21(4); 787-802 (1993), which is herein incorporated by reference.

Polymerases having 3'-5' exonuclease (3' nuclease) activity are preferred in practicing some embodiments of the methods disclosed herein. Polymerases having 3' nuclease activity include for example, *E. coli* DNA polymerase I, *Thermus thermophilus* (Tth) DNA polymerase, *Bacillus stearothermophilus* DNA polymerase, Vent, Deep Vent, T7, Klenow (exo+), and T4. All of which are known in the art and commercially available (e.g., New England Biolabs).

Polymerases capable of replicating a modified polynucleotide template are preferred in practicing some embodiments of the methods disclosed herein. Polymerases capable of replicating a modified polynucleotide template include Klenow (exo−) and (exo+) and T4. Other polymerases that may be suitable for replicating a modified polynucleotide template include Family A DNA polymerases, such as those disclosed in Braithwaite and Ito., *Nucleic Acids Res.* 21(4); 787-802 (1993), which is herein incorporated by reference, including Taq and T7. Such polymerases are well known in the art and can be tested in the assays described herein to determine their suitability for use in the methods described herein. For example, one may determine whether a particular test polymerase is capable or incapable of replicating a modified polynucleotide template by incubating the test polymerase with a modified polynucleotide template under conditions suitable for synthesizing an unmodified copy of the modified polynucleotide template. Such conditions are known in the art and readily accessible for commercially available polymerases. For example, suitable reaction conditions include (all conc. are final after mixing):

15 mM Tris-HCl pH 8.4
50 mM KCl
2.5 mM $MgCl_2$
3% DMSO
0.01% Tween-20
800 nM dNTPs (ACGT)
0.444×SYBR® (Molecular Probes, Eugene, Oreg.) Green (provided as 10,000×)
30 nM Rox reference dye (Stratagene Cat#600530)
Various concentrations of enzyme, e.g., 50 U/ml
100 nM Forward primer
100 nM Reverse primer
40 pM Oligo1 modified and its complementary sequence.

(SEQ ID NO: 4)
5'-TTTTTTTGCTCGACGGTGAAUGAUGTAGGUACCAGCAGUAACUCGAG

CACGUCUU 2'OMe(CG)A 2'OMe(CC)AAATCGGAUATTGCAGCCTC

GT-3'

83mer phosphodiester DNA/2'OMe, where 2'OMe indicates a 2'-O-methoxy modified nucleotide; U indicates 2' deoxyuridine A QPCR can then be performed in an MX3005P using the program for SYBR® (Molecular Probes, Eugene, Oreg.) green under reaction conditions suitable for the polymerase being tested. Detection of an amplification product indicates the polymerase is capable of replicating a modified polynucleotide template while no amplification indicates the polymerase is incapable of replicating a modified polynucleotide template.

Polymerases not capable of replicating a modified polynucleotide template are preferred in practicing some embodiments of the methods disclosed herein. Polymerases incapable of replicating a modified polynucleotide template include Pfu DNA polymerase. It is contemplated that other Family B DNA polymerases are also useful in practicing embodiments in which a polymerase not capable of replicating a modified polynucleotide template are required. Such polymerases include human α, δ and ε DNA polymerases, RB69 and Phi29 bacteriophage DNA polymerase and other Family B DNA polymerases disclosed in Braithwaite and Ito., *Nucleic Acids Res.* 21(4); 787-802 (1993), which is herein incorporated by reference.

The polymerases or portions thereof may be coupled to Streptavidin or Protein G or A. For example, Klenow or T4 may be fused to Streptavidin or Protein G. Methods of making polymerase fusion proteins are known in the art and described herein.

Additional polymerases that fall within one of the above mentioned categories are known in the art. In addition, polymerases can be tested for any of the above activities by assays known in the art and described herein. Buffer and extension temperatures are selected to allow for optimal activity by the particular polymerase. Buffers and extension temperatures useful for polymerases are know in the art and can also be determined from the vendor's specifications.

Oligonucleotides/Polynucleotides

The terms "polynucleotide", "oligonucleotide" and "nucleic acid (molecule)" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-, double-stranded and triple helical molecules. Polynucleotides may be isolated from genes, or chemically synthesized by methods known in the art.

Also provided are oligonucleotide primers and probes useful for detecting or measuring a nucleic acid, for amplifying a template nucleic acid sequence, and for forming a cleavage structure according to the methods disclosed herein.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification. In some embodiments, the primer may have a 3' flap which is cleaved by a 3' nuclease.

Oligonucleotide primers can be single-stranded DNA or RNA molecules that are hybridizable to a template nucleic acid sequence and prime enzymatic synthesis of a second nucleic acid strand. The primer is complementary to a portion of a target molecule. It is contemplated that oligonucleotide primers can be prepared by synthetic methods, either chemical or enzymatic. Alternatively, such a molecule or a fragment thereof is naturally-occurring, and is isolated from its natural source or purchased from a commercial supplier. Oligonucleotide primers and probes are 5 to 100 nucleotides in length, ideally from 17 to 40 nucleotides, although primers and probes of different length are of use. Primers for amplification are preferably about 17-25 nucleotides. Primers can be designed to have a particular melting temperature ($T_m$) by the method of melting temperature estimation. In some embodiments, the primer complementary to the polynucleotide template is designed to have a $T_m$ (e.g., 40° C.) that is lower than the $T_m$ of the effective $T_m$ of primers used in the detection/PCR reaction so as not to interfere with the detection/PCR reaction. Commercial programs, including OLIGO™ (Molecular Biology Insights, Inc., Cascade, Calif.), Primer Design and programs available on the internet, including Primer3 and Oligo Calculator can be used to calculate a $T_m$ of a nucleic acid sequence. Preferred, $T_m$'s of a primer will depend on the particular embodiment that is being practiced. For example, in one embodiment the primer will dissociate from a target at a temperature of 41° C. or more. While in other embodiments it is preferable to have a $T_m$ between about 45 and 65° C. and more preferably between about 50 and 60° C. The oligonucleotides include polynucleotide templates (modified or non-modified) and primers. The polynucleotide templates can be prepared with lengths ranging in length from at least 10 bases in length, typically at least 20 bases in length, for example, at least 30, 40, 50, 60, 70, 80, 90 or 100 bases in length. While the oligonucleotide can be large nucleic acid fragments, it is generally limited to nucleic acids of 500 bases or less.

The oligonucleotides may be free in solution or conjugated to a binding molecule. Oligonucleotides that are conjugated to a binding moiety will generally have a chemically active group (such as, primary amine group) at any point in its stretch of nucleic acids, which allows it to be conjugated.

As used herein, "modification" or "modified" refers to any change in a polynucleotide template (e.g., addition of non-conventional nucleotides) which renders the nucleic acid non-amplifiable by a specific class of polymerases (e.g., Pfu (exo⁻) but amplifiable by other polymerases (e.g., Klenow). Such modifications include replacing nucleic acid phosphates with a thiophosphates and replacing the 2' hydroxyls with 2'-β-methyl. Other suitable modifications include one or more of the following: 2'-deoxy-2'-fluoro-β-D-arabino-nucleic acid (2'F-ANA) nucleotides, locked-nucleic acids (LNAs) and ENAs: 2'-O,4'-C-ethylene-bridged nucleic acids, reversed deoxyribonucleotides, dU, hypoxanthine, 8-oxo-guanine, 8-oxo-adenine, ethenoadenine, apurinic sites, cholesterol adducts and other non-conventional nucleotides, e.g., such as those available from TriLink BioTech (San Diego, Calif.), PerkinElmer Life And Analytical Sciences, Inc. (Waltham, Mass.) and Sigma-Aldrich (St. Louis, Mo.).

A "non-conventional nucleotide" or "non-natural nucleotide" refers to a) a nucleotide structure that is not one of the four conventional deoxynucleotides dATP, dCTP, dGTP, and dTTP recognized by and incorporated by a DNA polymerase, b) a synthetic nucleotide that is not one of the four conventional deoxynucleotides in (a), c) a modified conventional nucleotide, or d) a ribonucleotide (since they are not normally recognized or incorporated by DNA polymerases) and modified forms of a ribonucleotide. These modified nucleotides can be tested via the methods described herein for their usefulness in embodiments utilizing a modified polynucleotide template.

Thus, the modified polynucleotide should not result in more than 10%, 5%, 1%, 0.5%, 0.1% and most preferably 0% of the amount of amplification product as produced with a non-modified polynucleotide template and the same polymerase (e.g., Pfu). One of ordinary skill in the art can determine whether a polymerase is capable of copying a modified polynucleotide template in assays known in the art. For example, in order to determine whether a particular polymerase is capable of amplifying a modified polynucleotide template the polymerase can be incubated with a modified polynucleotide template described herein in a primer extension reaction and the resulting product detected. The presence of amplification product indicates the polymerase is capable of copying a modified polynucleotide template while the absence of the amplification product indicates the polymerase is incapable of copying the modified polynucleotide template.

As noted above, the polynucleotide template is replicated to produce a template for amplification, usually an unmodified copy of the modified polynucleotide template. The design of the polynucleotide template is important because replication requires suitable complementary primer(s); and also because the polynucleotide template can provide for different means of detection and for flexibility in reaction conditions. For example, in some embodiments the polynucleotide template is modified.

The polynucleotide template may be double-stranded (ds), comprising a hybrid duplex of two complementary nucleic acid strands, or may alternatively, be single-stranded (ss). Either or both strands can carry modified bases.

In one embodiment, logarithmic replication can be achieved using a single-stranded polynucleotide template and a single primer. This is achieved by designing the polynucleotide template sequence to contain a primer binding sequence at one end of the ss target and a complement sequence of the primer binding site at the opposite end of the target strand. Annealing and extension of the primer will result in the formation of a complementary target strand containing the identical primer binding sites. In this way both the (+) and (−) strands of the resulting ds target contain an identical primer site at opposite ends of the target duplex, and the same primer used in combination with the polymerase and target nucleic acid promotes replication of both + and − target strands.

In other preferred embodiments, the base composition and sequence of the polynucleotide template sequence can be varied to accommodate different assay requirements. For example, the polynucleotide template may contain one or more modified nucleotides as described herein, so as to prevent replication by certain classes of polymerases (e.g., Pfu polymerase).

It is contemplated, for example, that a polynucleotide template sequence may be designed to contain a coupling linkage for the attachment of a detection molecule at the 5' end and a primer binding site at the 3' end with a variable region inserted between. Alternatively, the coupling linkage can be at the 3' end of the polynucleotide. The variable region could be of any length or composition, limited only by the requirements of the polynucleotide template amplification method. For example, an oligonucleotide can be conjugated to an antibody through a chemical coupling linkage at the 5' end. The polynucleotide template may contain a 5' binding region complementary to one of the replication primers, and a 3' site for binding the other replicated primer. The polynucleotide template may have a variable region of nucleic acid bases, which could be variable in length or in sequence, thereby providing alternative means of detection of the replicated targets based on size or other factors, including different sequences that are detected during the detection amplification reaction with specific primers and/or probes.

In another embodiment, a series of different polynucleotide templates are utilized for different analytes for use in a multi-plea assay. For example, a series of polynucleotide templates differing in either the primer binding site and/or the inner polynucleotide template region could be prepared, and coupled to different binding molecules which are capable of binding to different analytes. The replication products of each of these receptor conjugates (e.g., amplification product) could then be readily distinguished on the basis of size, or sequence in the detection reaction. For example amplification template specific primers and/or probes with different reporter molecules that can be used to distinguish a variety of different amplification products that may be present in a multi-plea reaction. Thus, multiple analytes could be detected in a real-time PCR reaction.

Coupling Polymerases and Polynucleotides to Binding Molecules or Moieties

In practicing the methods disclosed herein, two different types of linkages are contemplated. The first linking type comprises a polymerase or a portion thereof coupled covalently or non-covalently to an antibody or other binding molecule or binding moiety, including, for example, as an antibody-polymerase fusion protein or via binding through a streptavidin-biotin interaction. In a preferred embodiment, the binding molecule or binding moiety is an antibody coupled indirectly to a fusion protein comprising the first polymerase or a portion thereof fused to streptavidin or avidin. These may be prepared using methods well known to those skilled in the art. D. G. Williams, J. Immun. Methods, 79,261 (1984). Alternatively, enzyme-binding conjugates can be generated using recombinant DNA and genetic engineering techniques. I. Pastan and D. Fitzgerald, Science, 254, 1173 (1991). Enzymes suitable for use in the antibody conjugate include, but are not limited to polymerases (e.g., polymerases having 3' nuclease activity and polymerases capable of replicating a modified polynucleotide template). The choice of polymerase conjugate depends upon which embodiment is practiced.

Extensive guidance can be found in the literature for covalently linking proteins to binding compounds, such as antibodies, e.g. Hermanson, Bioconjugate Techniques, (Academic Press, New York, 1996), and the like. In one aspect, one or more proteins are attached directly or indirectly to common reactive groups on a binding molecule or binding moiety. Common reactive groups include amine, thiol, carboxylate, hydroxyl, aldehyde, ketone, and the like, and may be coupled to proteins by commercially available cross linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free mine on the binding molecule.

The second linking type consists of a polynucleotide template sequence coupled to an antibody or other binding molecule which recognizes an analyte. These can be prepared using variations of methods known to those skilled in the art for linking proteins to amino-oligonucleotides. For example, this may be accomplished using enzymatic tailing methods in which an amino-modified dent is added onto the 3' end of the nucleic acid. A. Kumar, Anal. Brioche., 169,376 (1988). Alternatively, amino-modified bases can be synthetically introduced into the nucleic acid base sequence. P. Li, et al., Nucleic Acids Res., 15, 5275 (1987). Antibodies can then be attached to amino-modified nucleic acids by substituting an antibody for an enzyme in the method of Urea. M. S, Urea, Nucleic Acids Res., 16, 4937 (1988).

In some embodiments, the nucleic acid/antibody conjugates involves the coupling of heterobifunctional cross-linkers to the DNA oligonucleotide targets which in turn are coupled to antibodies using chemistry described by Tseng et. al. in U.S. Pat. No. 5,324,650.

To facilitate the chemical attachment of the oligonucleotides to the antibodies, the oligonucleotides may be amino-modified by introducing a primary amine group at their 5' end during synthesis using cyanoethyl-phosphoramidite chemistry. The amino-modified oligonucleotides may be further modified with a hetero-bifunctional reagent that introduces sulfhydryl groups. The reagent, N-succinimidyl S-acetylthioacetate (SATA) is a heterobifunctional cross-linker agent that uses the primary amine reactive group, N-hydroxyl-succinimide (NHS) to couple to the amino-modified oligonucleotides introducing an acetyl-protected sulfhydryl group. The antibodies are modified with another NHS cross-linking agent, succinimidyl 4-(N-maleimidomethyl) cyclohexane-1-carboxylate (SMCC). The SMCC reacts with primary amine groups within the peptides (e.g., the .epsilon.-groups on lysine) of the antibody, introducing a maleimide group (a free sulfhydryl reactive group) to the antibody. The maleimide-modified antibodies are mixed with the SATA modified antibodies. The acetyl-protected sulfhydryl groups on the SATA-modified oligonucleotides are activated with the addition of hydroxylamine to produce reactive, free sulfhydryl groups (U.S. Ser. No. 07/946,247). The free sulfhydryl-containing oligonucleotides react immediately with maleimide-modified antibodies forming DNA to antibody conjugates.

The oligonucleotides can be attached to the binding molecules at the oligonucleotide's 5' nucleotide, 3' nucleotide or at an internal nucleotide. Alternatively, the oligonucleotides are attached indirectly to the binding molecule via streptavidin, protein A or protein G. For example, the oligonucleotides can be conjugated to antibodies via biotin-streptavidin.

The ASPs include a binding moiety coupled to a reactive moiety. In one embodiment, the binding moiety is an antibody and the reactive moiety is a first or second portion of a polymerase. In yet a further embodiment, the antibody and first or second portion of the polymerase is a fusion polypeptide. In a preferred embodiment, the binding moiety is an antibody coupled indirectly to a fusion protein comprising the first or second portion of the first polymerase fused to streptavidin or avidin.

Polymerase/antibody fusion proteins comprises a polypeptide chain comprising a first polypeptide sequence of an antibody of interest or an active fragment thereof and a second polypeptide sequence of a polymerase or a first or second portion thereof. The antibody-fusion polypeptides described herein can be made using methods known in the art. For example, the fusion proteins may be constructed as described in U.S. Pat. No. 6,194,177.

In general, a nucleic acid molecule encoding the antibody of interest is cloned by PCR and ligated, in frame, with a nucleic acid molecule encoding the polymerase or first or second portion thereof. The nucleic acid molecule encoding the fusion/hybrid protein is subsequently transfected into a host cell for expression. The sequence of the final construct can be confirmed by sequencing.

Nucleic acids encoding the polymerase or polymerase portions to be incorporated into antibody-polymerase hybrids can be obtained using routine techniques in the field of recombinant genetics. Basic texts disclosing the general methods of use include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Nucleic acid sequences encoding polymerases can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the polymerase sequences using a DNA or RNA template (see, e.g., Dieffenbach & Dveksler, PCR Primers: A Laboratory Manual (1995)). Alternatively, overlapping oligonucleotides can be produced synthetically and joined to produce one or more of the domains. Nucleic acids encoding polymerase can also be isolated from expression libraries using antibodies as probes.

The antibodies and polymerase or polymerase portion can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (See, e.g., Hermanson, Bioconjugate techniques (1996)). The polypeptides forming the fusion proteins may be linked C-terminus to N-terminus, although they can also be linked C-terminus to C-terminus. The different chains of amino acids in a fusion protein may be directly spliced together or may be indirectly spliced together via a chemical linking group or an amino acid linking group, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In some embodiments, the amino acid sequence of the antibody or binding fragment thereof is linked to a portion of a polymerase via a peptide linker. Exemplary peptide linkers are well known in the art and generally comprise several Gly and several Ser residues, e.g., such as GlyGlyGlySerSerGlyGlyGlySerGly (SEQ ID NO:26). In one embodiment, a peptide linker for use in a fusion protein acts as a flexible hinge.

In one embodiment, the polymerase or first or second portion of the polymerase is linked to the non-antigen binding portion of the antibody. In another embodiment, the polymerase or the first or second portion of the polymerase is linked to the C-terminus of the binding moiety.

Another embodiment is directed to binding molecule or moiety, such as an antibody, coupled to a Klenow that is 95% or more identical to the amino acid sequence of SEQ ID NO:1, wherein the Klenow retains polymerase activity.

Another embodiment is directed to a first portion of a first polymerase that is at least 95%, 98%, or 99% identical to the amino acid sequence of SEQ ID NO:2, so long as the first portion of the first polymerase forms a functional polymerase complex when it interacts with the second portion of the first polymerase.

Another embodiment is directed to a second portion of a first polymerase that is at least 95%, 98%, or 99% identical to the amino acid sequence of SEQ ID NO:3, so long as the second portion of the first polymerase forms a functional polymerase complex when it interacts with the first portion of the first polymerase.

Expression of ASPs

In certain embodiments, an ASP can be expressed using DNA molecules obtained by any of the methods described herein or those that are known in the art, which can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention comprises vectors (e.g., recombinant plasmids and bacteriophages) that include nucleic acid molecules (e.g., genes or recombinant nucleic acid molecules comprising genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived.

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast gal4 gene promoter, etc. Transcriptional initiation regulatory signals may be selected which allow for repression or activation, so that expression of the genes can be modulated.

In some embodiments, one or more DNA molecules comprising a nucleotide sequence encoding one or more polypeptide chains of a hybrid protein are operably linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use, if necessary.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express hybrid proteins. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particularly preferred method of high-yield production of the hybrid proteins is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Binding Molecules or Binding Moieties Attached to Solid Surface

In one embodiment, the method is practiced in the presence of a solid support. As used herein, a "solid support" or "solid surface" refers to any structure that provides a support for the binding molecule or binding moiety used as the capture molecule (e.g. antibody). Suitable solid supports include polystyrene, derivative polystyrene, a membrane, such as nitrocellulose, PVDF or nylon, a latex bead, a glass bead, a silica bead, paramagnetic or latex microsphere, or micro titer well. As a further example, the solid support may be a modified micro titer plate, such as a TopYield plate, which allows for covalent attachment of a capture molecule, such as an antibody, to the plate. When the solid support is a material such as a bead, paramagnetic microsphere or latex microsphere, the solid support may be contained in an open container, such as a multi-well tissue culture dish, or in a sealed container, such as a screw-top tube, both of which are commonly used in laboratories.

In one embodiment, a capture antibody is bound to a solid support. In an alternative embodiment, the analyte binds directly to the solid support.

The solid support may be modified to facilitate binding of the capture molecule to the surface of the support, such as by coating the surface with poly L-lysine, or siliconized with amino aldehyde silage or epoxysilane. The skilled artisan will understand that the circumstances under which the methods are performed will govern which solid supports are most preferred and whether a container is used.

Quantities of the capture molecule to be attached to the solid support may be determined empirically by checkerboard titration with different quantities of analyte that would be expected to mimic quantities in a test sample. Generally, the quantity of the analyte in the test sample is expected to be in the attogram to milligram range. An unknown concentration of the analyte in a test sample will be added at specified volumes, and this will influence the sensitivity of the test. If large volumes of the test sample (e.g., 200-400 µL) are used, modification of the test format may be needed to allow for the larger sample volumes. Generally, however, the concentration of the capture molecule will be about 1 to about 10 micrograms per mL.

The capture molecule can be attached to a solid support by routine methods that have been described for attachment of an analyte to plastic or other solid support systems (e.g., membranes or microspheres). Examples of such methods may be found in U.S. Pat. No. 4,045,384 and U.S. Pat. No. 4,046,723, both of which are incorporated herein by reference.

Attachment of the capture molecule to surfaces such as membranes, microspheres, or micro titer wells may be performed by direct addition in PBS, or other buffers of defined pH, followed by drying in a convection oven.

The capture molecule may be attached to the solid support by an attachment means, such as via adsorption, covalent linkage, avidin-biotin linkage, streptavidin-biotin linkage, heterobifunctional cross-linker, Protein A linkage or Protein G linkage. Each of the attachment means should permit the use of stringent washing conditions with minimal loss of the capture molecule from the surface of the solid support. As an example, the adsorption may be hydrophilic adsorption. As a further example, the heterobifunctional cross-linker may be maleic anhydride, 3-aminopropyl trimethoxysilane (APS), N-5 azido, 2-nitrobenzoyaloxysuccinimide (ANB-NOS) or mercaptosilane.

The capture molecule may be attached to the solid support though a portion of the capture molecule, such as an amino acid residue, preferably a lysine or arginine residue, a thiol group or a carbohydrate residue. When the capture molecule is an antibody, the thiol group may be a thiol group of the antibody hinge region.

The solid support may be derivatized with avidin or streptavidin, and the capture molecule may be modified to contain at least one biotin moiety, to aid in the attachment of the capture molecule to the solid support. Alternatively, the solid support may be derivatized with biotin, and the capture molecule may be modified to contain at least one avidin or at least one streptavidin moiety.

Test Sample and Analyte Binding

In practicing the methods disclosed herein, a test sample suspected of containing the selected analyte under investigation can be applied to the support containing the capture molecule. Alternatively, in a solution based assay the test sample is directly added to a reaction mixture or vessel that does not include a solid support. Depending on the identity of the support, the support may be contained within a culture device of some type. When the support is a membrane, for example, a shallow glass dish slightly bigger that the length and width of the membrane may be used. When the support is a microsphere, the microspheres may be contained in a tube, such as a polypropylene or polystyrene screw-top tube. The identity of the reaction vessel or container is not critical, but it should be constructed of a material to which the reagents used in the methods do not adhere.

The quantity of test sample used is not critical, but should be an amount that can be easily handled and that has a concentration of analyte that is detectable within the limits of the methods disclosed herein. The test sample should also be sufficient to adequately cover the support, and may be diluted if needed in this regard. For example, the quantity of the test sample may be between 0.2 µL and 2 mL. Preferably, the quantity of the test sample is between 0.2 µL and 1 mL. Most preferably, the quantity of the test sample may be between 0.2 µL and 200 µL.

While the concentration of the analyte in the test sample is not critical, it should be within the detection limits of the methods disclosed herein. The skilled artisan will understand that the concentration may vary depending on the volume of the test sample, and thus it is difficult to provide a concentration range over which a analyte may be detected. Preferably a test sample used in the methods contains between about $1 \times 10^{-6}$ and about $1 \times 10^{-18}$ g of the analyte, more preferably between about $1 \times 10^{-6}$ g and about $1 \times 10^{-15}$ g of the analyte, most preferably between about $1 \times 10^{-6}$ g and about $1 \times 10^{-18}$ g of the analyte.

The methods and kits taught herein can thus be used to detect analyte present in a sample at a concentration of, for example, about 10 pg/mL or less, about 1 ng/mL or less, about 0.7 ng/mL or less, about 0.5 ng/mL or less, about 0.1 ng/mL or less, about 0.01 ng/mL or less, about 1 pg/mL or less, about 0.1 pg/mL or less, about 0.01 pg/mL or less, about 1 fg/mL or less.

In some embodiments, a solid support and capture antibody are used. In this embodiment, the capture molecule is incubated with the solid support for a period of time sufficient to allow the capture molecule to bind the solid support. Alternatively an analyte is incubated with the solid support for a period of time sufficient to allow the analyte to bind the solid support. Preferably, the incubation proceeds from between about 10 minutes and about 60 minutes, but may proceed longer, including overnight, if appropriate.

The temperature at which each of the incubation steps of the methods is performed is also not critical. Preferably, the temperature at which the incubations occur is between about 18° C. and about 37° C. More preferably, the incubation temperature is between about 18° C. and about 30° C. Most preferably, the incubation temperature is at ambient temperature (20° C.). After addition of the analyte and capture antibody a wash is generally performed followed by a detector molecule binding reaction.

Detector Antibody Binding and Extension Reaction

In certain embodiments, the first nucleic acid polymerase and a detector molecule, such as an antibody, are added in a suitable buffer. The first nucleic acid polymerase is coupled to the detector antibody (e.g., fusion protein or a biotin-streptavidin interaction). In one embodiment, this step of the reaction utilizes a modified polynucleotide template and a first polymerase that is capable of amplifying the modified polynucleotide template. In another embodiment, this step of the reaction utilizes a first polymerase having 3' nuclease activity and a primer complementary to the polynucleotide template and having a 3' flap and a 5' region that introduces a new primer binding site upon extension. The detector antibody may be coupled to the first nucleic acid polymerase before it is added to the reaction mixture or may be coupled during the incubation with the analyte (e.g., biotin labeled detector antibody and added streptavidin-Klenow). In another embodiment, a first analyte specific probe and a second analyte specific probe are added in a suitable buffer. The first analyte specific probe has a detector molecule, such as an antibody, coupled to a first portion of a first polymerase while the second analyte specific probe has a detector molecule, such as an antibody, coupled to a second portion of the first polymerase. The first and second portions of the nucleic acid polymerase may be coupled to the detector antibodies before they are added to the reaction mixture or they may be coupled during incubation with the analyte (e.g., biotin labeled antibody and added streptavidin-first and second portions of Klenow.).

The reaction mixture is allowed to incubate for a period of time sufficient to allow the detector antibody to bind the analyte. Preferably, the incubation proceeds from between about 5 minutes to about 60 minutes, but may proceed longer, including overnight, if appropriate.

The temperature at which each of the incubation step of the methods is performed is also not critical. Preferably, the temperature at which the incubations occur is between about 18° C. and about 37° C. More preferably, the incubation temperature is between about 18° C. and about 30° C. Most preferably, the incubation temperature is at ambient temperature (20° C.). After the incubation the wells are washed with a wash buffer.

In one embodiment the analyte-detector antibody incubation reaction and extension reaction are performed simultaneously under the same reaction conditions. In a preferred embodiment, the analyte-detector antibody incubation reaction and extension reaction are performed sequentially.

An extension reaction mixture is then added to the wells. The extension reaction mixture includes a modified polynucleotide template, as described herein, and one or more reverse primers that are complementary to a portion of the modified polynucleotide template. The reaction mixture is generally incubated for 30 minutes to overnight at room temperature. In one embodiment, the polynucleotide template is modified so as to have one or more non-conventional nucleotides. During the incubation step the primer anneals to the modified polynucleotide template and is extended by the first nucleic acid polymerase or the polymerase complex formed by the interaction of the first and second portions of the first polymerase so as to form an unmodified copy of the modified polynucleotide template. The unmodified copy is then utilized in a detection reaction.

The skilled artisan will understand that the detector binding/primer extension conditions may vary depending on the nature and identity of the polynucleotide molecule and the nature and identity of the primer or primers. The skilled artisan will understand that many other DNA polymerases, having the criteria as discussed herein (e.g., having 3' nuclease activity) are available that may be used in the methods disclosed herein. Exemplary conditions are described in the Examples.

Detection Assay

After the binding/extension reaction, a detection reaction is performed. This reaction may occur in the same reaction vessel that the extension reaction occurred or in a separate reaction vessel. Preferably, the detection reaction is the polymerase chain (PCR), performed using an oligonucleotide primer or primers that is specific for the template (and/or compliment thereof) for amplification produced during the extension reaction (e.g., an unmodified copy of the modified polynucleotide template). PCR may be conducted directly on the assay system in a microwell plate, or in some other suitable container (such as when microbeads are used as the support).

PCR amplification buffer, an oligonucleotide primer or primers specific to the template for amplification (and/or compliment thereof), and the second DNA polymerase (e.g., polymerases lacking 3' nuclease activity or Pfu DNA polymerase) are incubated. The skilled artisan will understand that the amplification buffer and DNA polymerase used in the PCR may vary depending on the nature and identity of the polynucleotide molecule portion of the amplification molecule and the nature and identity of the primer or primers. In one embodiment, the second polymerase added to the reaction (e.g., Pfu DNA polymerase) is unable to amplify a modified polynucleotide template. An exemplary PCR amplification buffer/primer/DNA polymerase composition is 15 mM Tris-HCl pH 8.4, 50 mM KCl, 2.5 mM $MgCl_2$, 3% DMSO, 0.01% Tween-20, 800 µM dNTPs (ACGT), Pfu (exo⁻) 50 U/ml (Stratagene Cat#600163-81), and 100 nM of primer in a 25 µl reaction mixture. The skilled artisan will understand that many other DNA polymerases, having the criteria as discussed herein (e.g., substantially lacking 3' nuclease activity) are available that may be used in the methods disclosed herein.

In one embodiment, the second polymerase that is added to the reaction mixture substantially lacks 3' nuclease activity. In another embodiment, the second polymerase added to the reaction is unable to amplify a modified polynucleotide template. In this latter embodiment, the second polymerase may or may not exhibit 3' nuclease activity.

The PCR amplification may be carried out in any of the commercially available systems for performing PCR as long as the second polymerase falls within the criteria discussed herein (e.g., unable to amplify a modified polynucleotide template or substantially lacking 3' nuclease activity). The time and temperature of the PCR will depend on the nature and identity of the polynucleotide molecule portion of the amplification molecule and the nature and identity of the primer or primers. Exemplary conditions include 40 cycles at 95° C. (15 s) and 63° C. (45 s).

In addition to PCR amplification, the methods disclosed herein may be practiced using Strand Displacement Amplification (SDA), Rolling Circle Amplification (RCA), Transcription Mediated Amplification (TMA) or Ligase Chain Reaction (LCR). Amplification of signal may be generated in a homogeneous, closed tube environment, using Real-Time amplification. Instrumentation suitable for Real-Time amplification includes the ABI PRISM® (Applied Biosystems, Inc., Foster City, Calif.) TAQMAN® (Roche Molecular Systems Inc., Alameda, Calif.) system, LIGHTCYCLER® (Roche Diagnostic GmbH, Mannheim, Germany), RAPIDCYCLER® (Idaho Technologies, Salt Lake City, Utah), Bio-Rad's thermal cyclers, and SMARTCYCLER® (Cepheid Corporation, Sunnyvale, Calif.).

The unmodified copy or the template for amplification may be detected during a PCR reaction by various methods known in the art. The detection of the amplified product may be detected by several means including, but not limited to, (a) direct detection of a released cleavage product on a gel; (b) indirect or direct detection of a signal generated during a nucleic acid cleavage reaction (TAQMAN® (Roche Molecular Systems Inc., Alameda, Calif.) reaction); (c) fluorescent change upon a probe binding a target (molecular beacon); or SYBR® (Molecular Probes, Eugene, Oreg.) Green detection assay (e.g., see Examples). Cleavage reactions utilizing an endonuclease activity include the INVADER® detection assay (Third Wave Technologies; Madison, Wis.) which is described in U.S. Pat. No. 6,348,314 and is herein incorporated by reference in its entirety. Cleavage reaction assays encompassed by the present methods also include molecular beacon detection assays (supplied by a variety of commercial sources) and TAQMAN® (Roche Molecular Systems Inc., Alameda, Calif.) detection assays (supplied by a variety of commercial sources including Roche) which are described in U.S. Pat. Nos. 5,723,591; 5,925,517 and 5,804,375, each of which is herein incorporated by reference in its entirety. Cleavage reactions useful in certain embodiments are also described in U.S. Pat. No. 6,548,250 which is herein incorporated by reference. Such cleavage reactions may be practiced by the nuclease in the methods disclosed herein.

Between the addition of reagents in the methods disclosed herein, including, in particular, those methods using a solid support and a capture antibody, the assay system is preferably subjected to washing to reduce the incidence of non-specific binding. In the intact polymerase (non-split) or the split polymerase systems, stringent wash conditions that do not cause dissociation of the complex comprising the binding molecule, first polymerase, and analyte or the ASP-analyte and first polymerase complex can be employed. For example, heating, pH changes, or (and) the addition of formamide, detergents and salts can be used to increase the efficiency of the wash step. Too stringent conditions can lead to dissociation of the complex comprising the binding molecule, first polymerase and analyte or the ASP-analyte and first polymerase complexes or destruction of the reporter. Tolerance to stringent wash conditions will vary with the nature of the analyte, binding member, reactive moiety, polymerase, and specific reporter used. The stringent conditions, therefore, should be experimentally optimized for each assay. However, in washing to reduce non-specific binding, if some of the complexes comprising the binding molecule, first polymerase and analyte or the ASP-analyte and polymerase complexes are lost, this can be compensated for by additional target replication realized by increasing the number of temperature recycle steps or increasing the time of the primer extension step.

While the number of wash cycles and soak times is empirically determined, in general either water or a low or high molarity salt solution with a detergent such as Tween 20, Triton X-100, or NP-40 may be used as the washing solution. 1-5 or 1-8 washes, each lasting 5 or 15 seconds to 10 minutes may be performed, after incubation of each of the reagents used in the methods. The detergent concentration is typically 0 to 1% with a salt concentration of 0 to 1000 mM (e.g., NaCl). Preferably, washing takes place between each incubation step, e.g., after addition of the capture molecule to the solid support, after addition of the test sample and after addition of the detector molecule. Exemplary washing conditions are described in the Examples.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Analyte Detection Reaction Utilizing a Modified Polynucleotide Template

These reactions can be used to measure an analyte affixed directly or indirectly to a solid phase (e.g., ELISA plate).

The following assay was performed with the R&D Systems DUO SET ELISA development kits for human EGF and human VEGF (cat# DY236 & DY293B; R&D Systems, Minneapolis Minn.) to measure the amount of an analyte in a sample.

The R&D System's kits were used according to the manufacturer's instructions for overnight coating of capture antibody, blocking, analyte dilution and capture, washing and application of biotinylated detection antibody. However, after addition of the detection antibody the Streptavidin ("SAv")-horseradish peroxidase from the commercial kit was substituted with SAv-Klenow (exo⁻). SAv-Klenow (exo⁻) was diluted to 100 ng/ml in Blocking/dilution buffer.

The SAv-Klenow (exo⁻) was added to the ELISA plate at 75 μl/well and incubated for 30 min at room temperature to allow the SAv to bind to the biotinylated antibody. The solution was aspirated from the wells and wells were washed 4 times with 400 μl of TBST followed by 2 washes with water. A Klenow extension mix was added to the wells at 75 μl/well and an unmodified copy of the modified polynucleotide template was allowed to form for 30 min at room temperature. The Klenow Extension Mix included (all conc. are final after mixing):

10 mM Tris-HCl (pH 7.5)
5 mM $MgCl_2$
7.5 mM DTT
100 μg/ml BSA
500 μm dNTP (ACGT)
100 nM Alien 1-Reverse primer
40 pM Oligo1

The following oligonucleotides were also used:

```
Alien1(modified polynucleotide template) = Oligo 1:
                                     (SEQ ID NO: 4)
5'-TTTTTTTGCTCGACGGTGAAUGAUGTAGGUACCAGC AGUAACUCGA GCACGUCUU 2'OMe(CG)A 2'OMe(CC) AAATCUGGAUATTGCAGCC

TCGT-3'
```

83mer phosphodiester DNA/2'OMe, where 2'OMe indicates a 2'-O-methoxy modified nucleotide; U indicates 2' deoxyuridine

```
Alien1-Rev primer (anneals to 3' end of Oligo 1
to prime QPCR suitable strand):
                                     (SEQ ID NO: 5)
ACGAGGCTGCAATATCCAGA PCR primers:
                                     (SEQ ID NO: 5)
Alien1-Rev: ACGAGGCTGCAATATCCAGA (SEQ ID NO: 6)
Alien1-Fwd: TGCTCGACGGTGAATGATGT
```

Aliquots of the extension reactions containing the unmodified copy of the modified polynucleotide template were moved to corresponding wells of a 96-well PCR plate containing 2×QPCR Master Mix (once diluted with sample to 1× the MM) and anti-Pfu (antibody which was used to facilitate a hotstart amplification). The QPCR amplification Master Mix included (all conc. are final after mixing with sample):

15 mM Tris-HCl pH 8.4
50 mM KCl
2.5 mM $MgCl_2$
3% DMSO
0.01% Tween-20
800 μM dNTPs (ACGT)
0.444×SYBR® (Molecular Probes, Eugene, Oreg.) Green (provided as 10,000×)
30 nM Rox reference dye (Stratagene Cat#600530)
Pfu(exo⁻) 50 U/ml (Stratagene Cat#600163-81)
100 nM Alien 1-Forward primer
100 nM Alien 1-Reverse primer Samples were mixed and run in an MX3005P real-time PCR devise using the program for SYBR® (Molecular Probes, Eugene, Oreg.) green with dissociation curve and 2-step cycling parameters of [95° C. for 10 min] (1 cycle), [95° C. for 15 sec, 63° C. for 45 sec] (40 cycles).

Figure 3A:
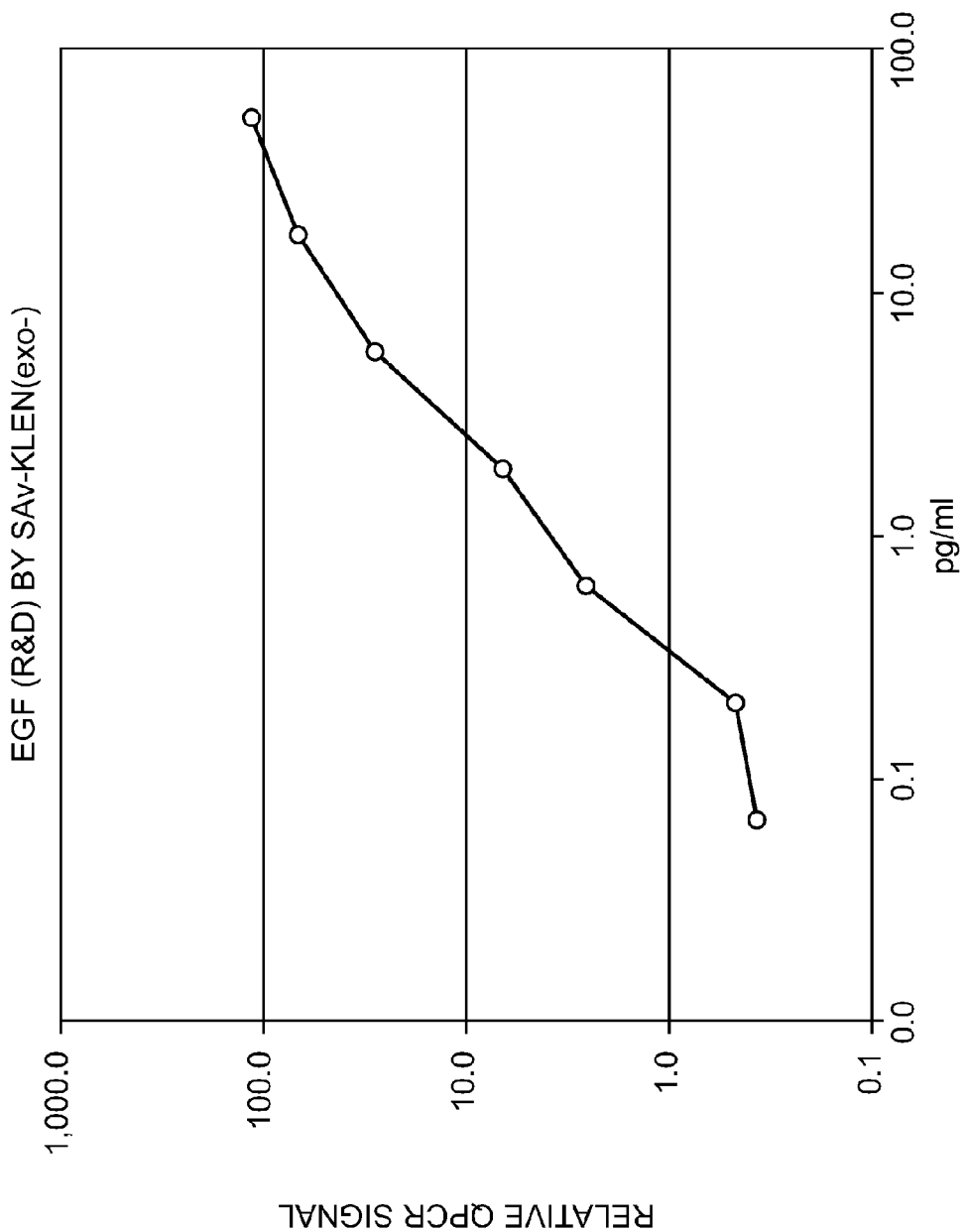
FIGS. 3A and 3B depict data obtained with a detection assay using a capture antibody and a modified polynucleotide template for EGF or VEGF.
Figure 3B:
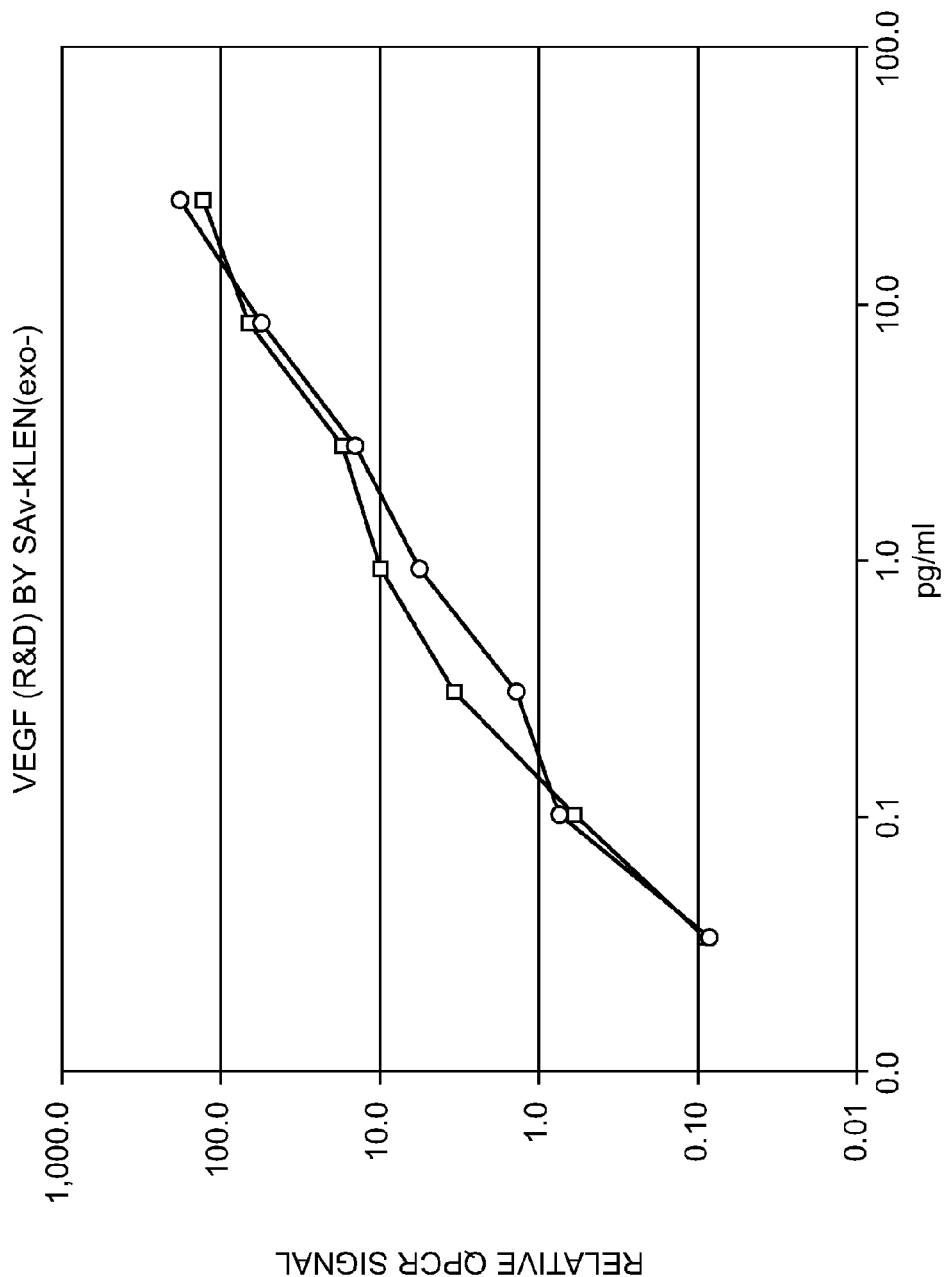

The relative QPCR signal was computed by calculating the change in Ct between the Ct at analyte concentration=0 pg/ml and the Ct at analyte concentration=X pg/ml. This was called the 'dCt from 0'. In a 100% efficient assay, a change of one Ct is equivalent to a doubling of the amount of initial usable QPCR template. To convert this logarithmic signal into a linear quantity we used the following formula 'Relative QPCR Signal'=2^(dCt from 0)-1. FIGS. 3A and 3B show the QPCR signal plotted against the concentration of analyte (pg/ml) used in a sample.

Example 2

Analyte Detection Reaction Utilizing a Modified Polynucleotide Template and No Capture Antibody The following assay was performed identical to Example 1, but with the modifications described herein.

A dust mite extract was coated onto R&D System 8-well strip tubes (Cat#DY990; R&D Systems, Minneapolis Minn.) at 40 µg/ml in carbonate buffer pH 9.6 for 16 hr at 4° C. in a 75 ul volume. Wells were washed 2× with TBST and blocked for 2 hr at 37° C. with Blocking/Dilution buffer.

Wells where then incubated for 1-2 hours at room temperature with 75 µl of serum from patients known to be either allergic, or not allergic for dust mite allergen. Dilutions of sera were carried out in normal goat serum. Wells were washed 4× with TBST followed by incubation with 75 µl Affinity Purified Goat Anti-Human IgE(Fc) Biotin Labeled (Cat#116BN; American Qualex; San Clemente, Calif.) (stock at 0.5 mg/ml in 0.01M PBS pH7.6, 1% BSA) diluted 1:10,000 in blocking/dilution buffer for 1 hr at RT. Wells were then washed 3× with TBST and once with water.

SAv-Klenow (exo$^-$) was added to the ELISA plate at 75 µl/well and incubated for 30 min at room temperature to allow the SAv to bind to the biotinylated antibody. The solution was aspirated from the wells and wells were washed 4 times with 400 µl of TBST followed by twice with water. The Klenow extension mix was added to wells at 75 µl/well and an unmodified copy of the modified polynucleotide template was allowed to form for 30 min at room temperature.

Aliquots of the extension reactions containing the unmodified copy of the modified polynucleotide template were moved to the corresponding wells of a 96-well PCR plate containing 2×QPCR Master Mix (once diluted with sample to 1× the MM). Also included was anti-Pfu antibody to facilitate hotstart amplification.

Samples were mixed then run in an MX3005P real-time PCR devise using the program for SYBR® (Molecular Probes, Eugene, Oreg.) green with dissociation curve and 2-step cycling parameters of [95° C. for 10 min] (1 cycle), [95° C. for 15 sec, 63° C. for 45 sec] (40 cycles).

Figure 4:
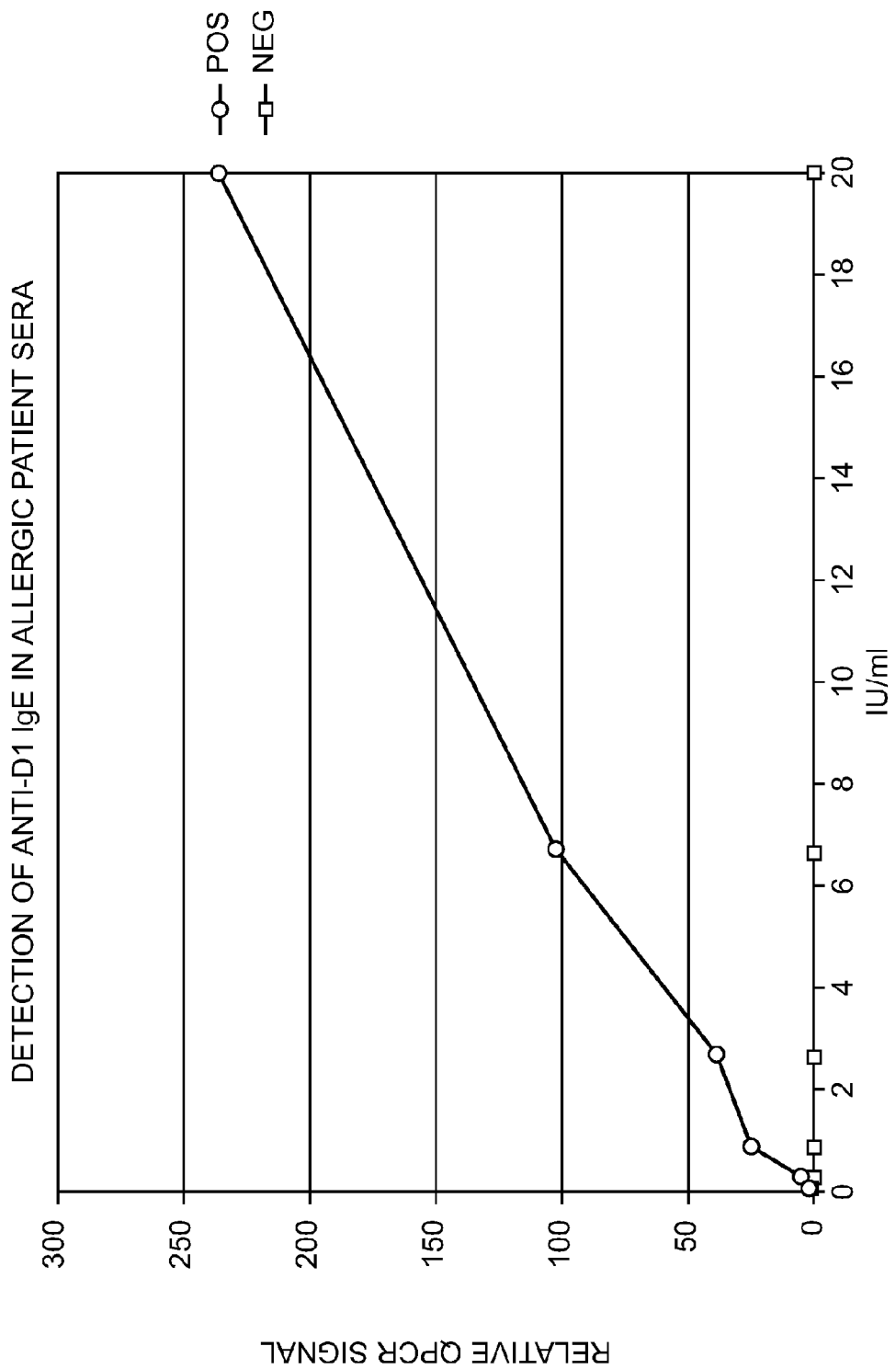
FIG. 4 depicts data obtained with a detection assay using an analyte that is directly bound to a plate and a modified polynucleotide template.

The results show that the assay is extremely effective in distinguishing an allergic patient's sera from a negative control (FIG. 4).

Example 3

Analyte Detection Reaction Utilizing, a Primer with a 3' Flap

Figure 5:
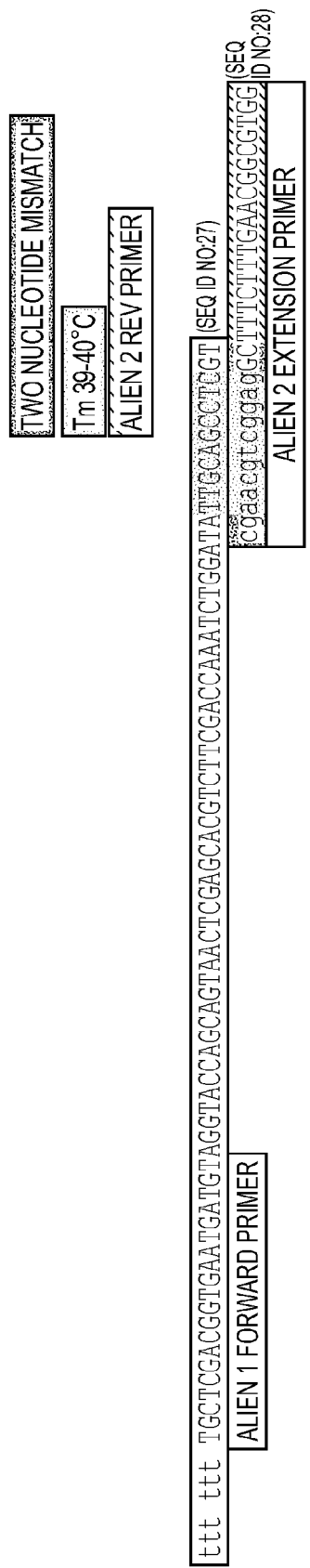
FIG. 5 illustrates a polynucleotide template (Alien 1 template) and primers that can be used in an analyte detection reaction utilizing a primer (Alien 2 extension primer) having a 3' flap and a 5' region that creates a PCR primer binding site. The Alien 2 extension primer contains two-nucleotide mismatches flanking the complementary region to inhibit extension by an exo⁻ polymerase. The Alien 2 extension primer does not anneal above 40° C. A control primer (not shown) has a two nucleotide mismatch on one end only.

In this example, a primer with a 3' flap and a 5' region that introduces a new primer binding site upon extension, a first polymerase having 3' nuclease activity and a second polymerase substantially lacking 3' nuclease activity were used. Even though the below listed protocol is a solution-phase assay (no binding of analyte or capture antibody to a solid support) it can be adopted easily by one of routine skill in the art for use in a solid-phase assays. Oligonucleotides utilized in this example are illustrated in FIG. 5.

The following reaction components were prepared (all conc. are final after mixing):
  10 mM Tris-HCl (pH 7.5)
  5 mM MgCl$_2$
  7.5 mM DTT
  100 µg/ml BSA
  500 µm dNTP (ACGT)
  40 pM Alien 2-extension primer
  40 pM Oligo 1 (modified polynucleotide template)
  Various amount of SAv-Klenow diluted from a 4 mg/ml stock (exo$^+$)

Reactions containing between 0 and 1×10$^9$ molecules of SAv-Klenow (exo$^+$) were incubated in a 25 µl volume in PCR tubes for 30 min at room temperature to allow the polymerase to create an unmodified copy of the Oligo1 template. The Alien 2-extension primer incorporated a primer binding site for the Alien 2-Reverse PCR primer into the unmodified copy of the Oligo 1 template.

After the extension reaction was complete 12.1 µl were transferred to a new tube containing 12.9 µl of a QPCR amplification Master Mix containing (all conc. are final after mixing with sample):
  15 mM Tris-HCl pH 8.4
  50 mM KCl
  2.5 mM MgCl$_2$
  3% DMSO
  0.01% Tween-20
  800 µM dNTPs (ACGT)
  0.444×SYBR® (Molecular Probes, Eugene, Oreg.) Green (provided as 10,000×)
  30 nM Rox reference dye (Stratagene Cat#600530)
  Pfu(exo$^-$) 50 U/ml (Stratagene Cat#600163-81)
  Hot-start Antibody
  100 nM Alien 1-Forward primer
  100 nM Alien 2-Reverse primer The samples were mixed and run in a MX3005P real-time PCR device using the program for SYBR® (Molecular Probes, Eugene, Oreg.) green with dissociation curve and 2-step cycling parameters of [95° C. for 10 min] (1 cycle), [95° C. for 15 sec, 63° C. for 45 sec] (50 cycles).

The results indicted that the assay can be used for the detection of an analyte.

Example 4

Reconstitution of Klenow Activity in the Presence of Biotinylated Antibody

Figure 7:
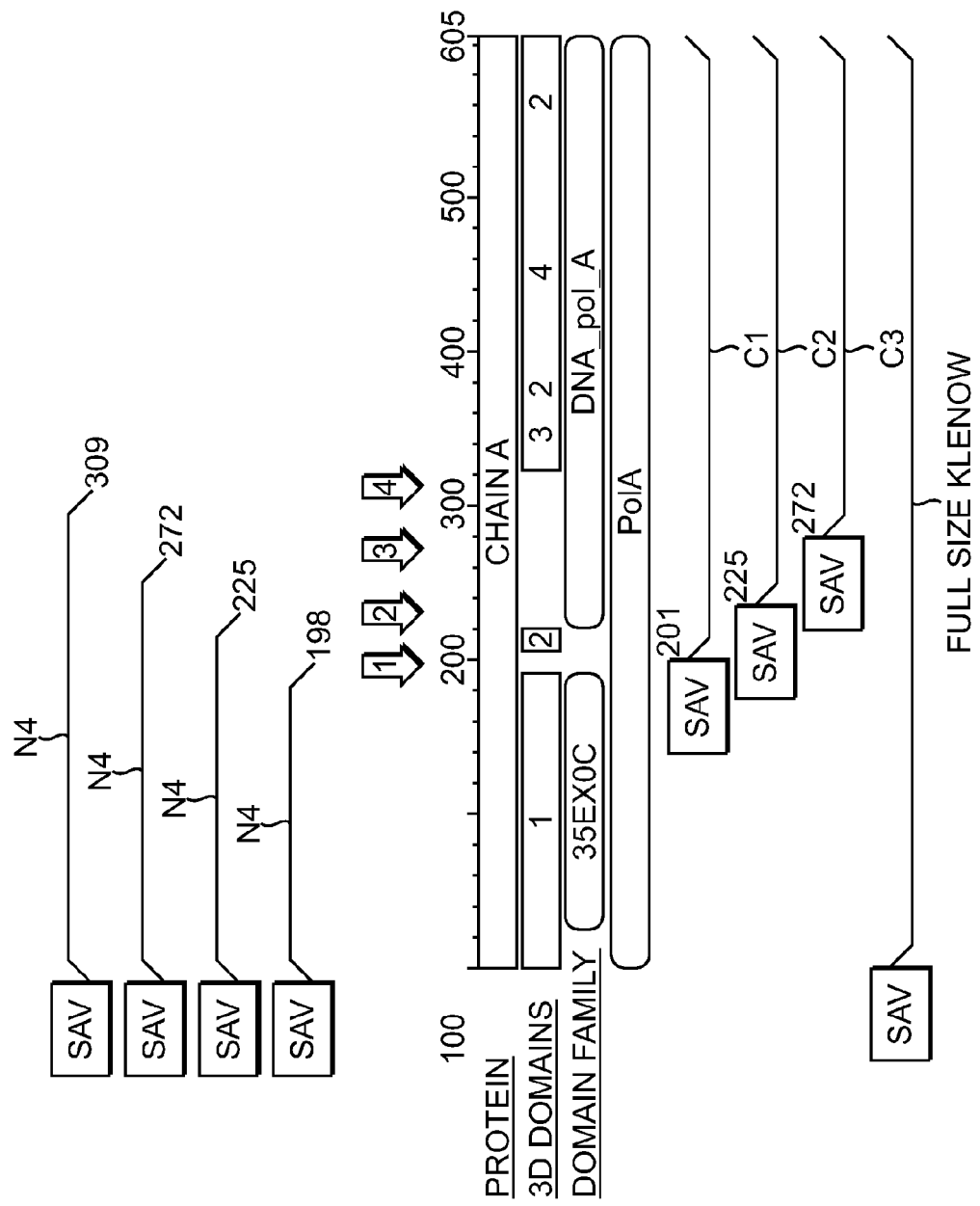
FIG. 7 illustrates the full-length Klenow enzyme and various portions that may be useful in various aspects of the invention.

The following assay was performed for each of the N-terminal/C-terminal Klenow split embodiments shown in FIG. 7 to identify the optimal constructs for use in practicing the present invention. Results and conditions for the N2/C2 split are described below.

Briefly, Klenow N2 and C2 Streptavidin-fusion proteins (See FIG. 7) were diluted in 30 mM sodium phosphate pH7.2, 50 mM NaCl, 4 mM DTT, 50% glycerol to concentrations of 0.19 mg/ml and 0.27 mg/ml respectively.

The following reaction mixtures were then prepared:
  2 µl of each of Klenow N2 and C2 fusion polypeptides
  6 µl of reaction mixture containing 16 mM Tris-HCl pH 7.5, 8 mM MgCl$_2$, 4 mM DTT,
  0.5 mM dNTPs
  0.2 mM Reverse primer:

5'-ACGAGGCTGCAATATCCAGA-3'   (SEQ ID NO: 5)

0.1 mM Oligo 1 template (modified polynucleotide template):

```
                                              (SEQ ID NO: 4)
5'-TTTTTTTGCTCGACGGTGAAUGAUGTAGGUACCAGCAGUAACUCGA

GCACGUCUU 2'OMe(CG) A 2'OMe(CC) AAATCUGGAUATTGCAGCC

TCGT-3'
```

83-mer phosphodiester DNA/2'OMe; U indicates 2'deoxyuridine biotin labeled goat anti-rabbit IGG at 25 μg/ml concentration (American Quialex, San Clemente, Calif.).

The reaction mixtures were incubated at room temperature overnight allowing the split polymerase fusion polypeptides to bind the biotinylated antibody to form a functional Klenow complex and synthesize an unmodified copy the oligo 1 template.

The next day the reaction mixtures were diluted 1:250 with water. 12.1 μl of each diluted reaction mixture was combined with 12.9 μl of a QPCR Master Mix. The QPCR amplification Master Mix included (all conc. are final after mixing with sample):

15 mM Tris-HCl pH 8.4
50 mM KCl
2.5 mM MgCl$_2$
3% DMSO
0.01% Tween-20
800 μM dNTPs (ACGT)
0.444×SYBR® (Molecular Probes, Eugene, Oreg.) Green (provided as 10,000×)
30 nM Rox reference dye (Stratagene Cat#600530)
Pfu (exo$^-$) 50 U/ml (Stratagene Cat#600163-81)

```
100 nM Alien 1-Forward primer:
5'-TGCTCGACGGTGAATGATGT-3'           (SEQ ID NO: 6)

100 nM Alien 1-Reverse primer:
5'-ACGAGGCTGCAATATCCAGA-3'           (SEQ ID NO: 5)
```

Samples were mixed and run in an MX3005P real-time PCR devise using the program for SYBR® (Molecular Probes, Eugene, Oreg.) green with dissociation curve and 2-step cycling parameters of [95° C. for 10 min] (1 cycle), [95° C. for 15 sec, 63° C. for 45 sec] (40 cycles).

Figure 8:
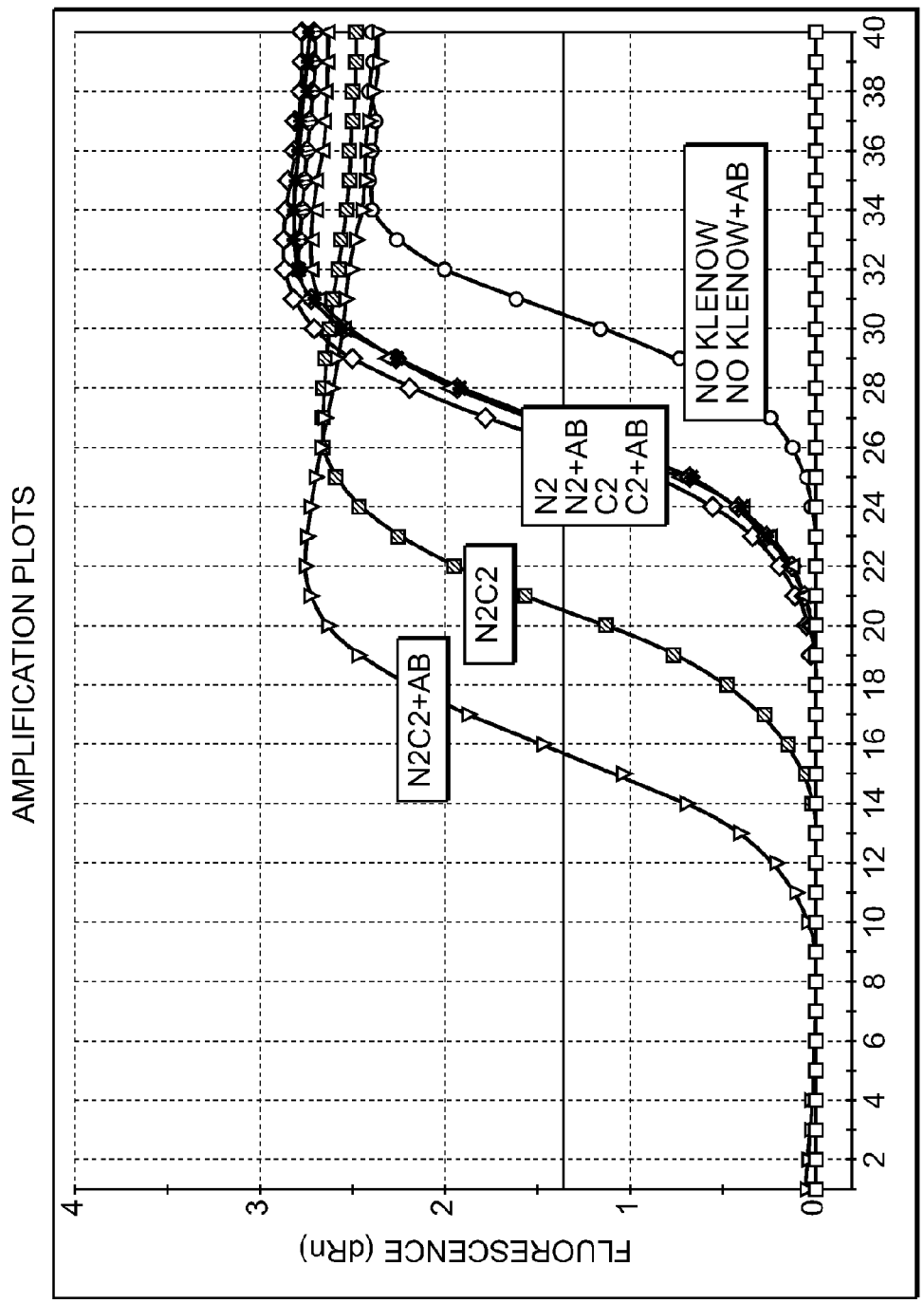
FIG. 8 depicts the results of a detection reaction using the N2 and C2 fragments of Klenow in the presence of biotinylated antibody.

The QPCR data are represented in FIG. 8. Combination of both halves of split Klenow with biotinylated antibodies (N2C2+AB) resulted in a substantially better signal than combination of both halves without the antibodies (N2C2). This indicates that proximity interaction between the two parts of split Klenow is facilitated by their binding to the antibodies and interaction of the polymerase portions.

Example 5

Optimization of Working Range

Titration of Analyte

In order to determine the optimal antibody concentration for use with the split Klenow fusion polypeptides the reaction mixtures were prepared and processed as in Example 4, except that the concentration of split Klenow portions, reverse primer and the template were 100× less, and the reactions were supplemented with 0.01% BSA (New England Biolabs, Beverly, Mass.).

To study the dose response, antibodies concentrations were varied from the 1 biotin molecules per 1 Klenow molecule (1:1 ratio) of Example 4. Biotinylated antibody concentrations were adjusted to produce biotin-to-Klenow ratios of 1:100, 1:10, 1:3.33, 1:1, 3.33:1, 10:1, and 100:1 were used.

Figure 9:
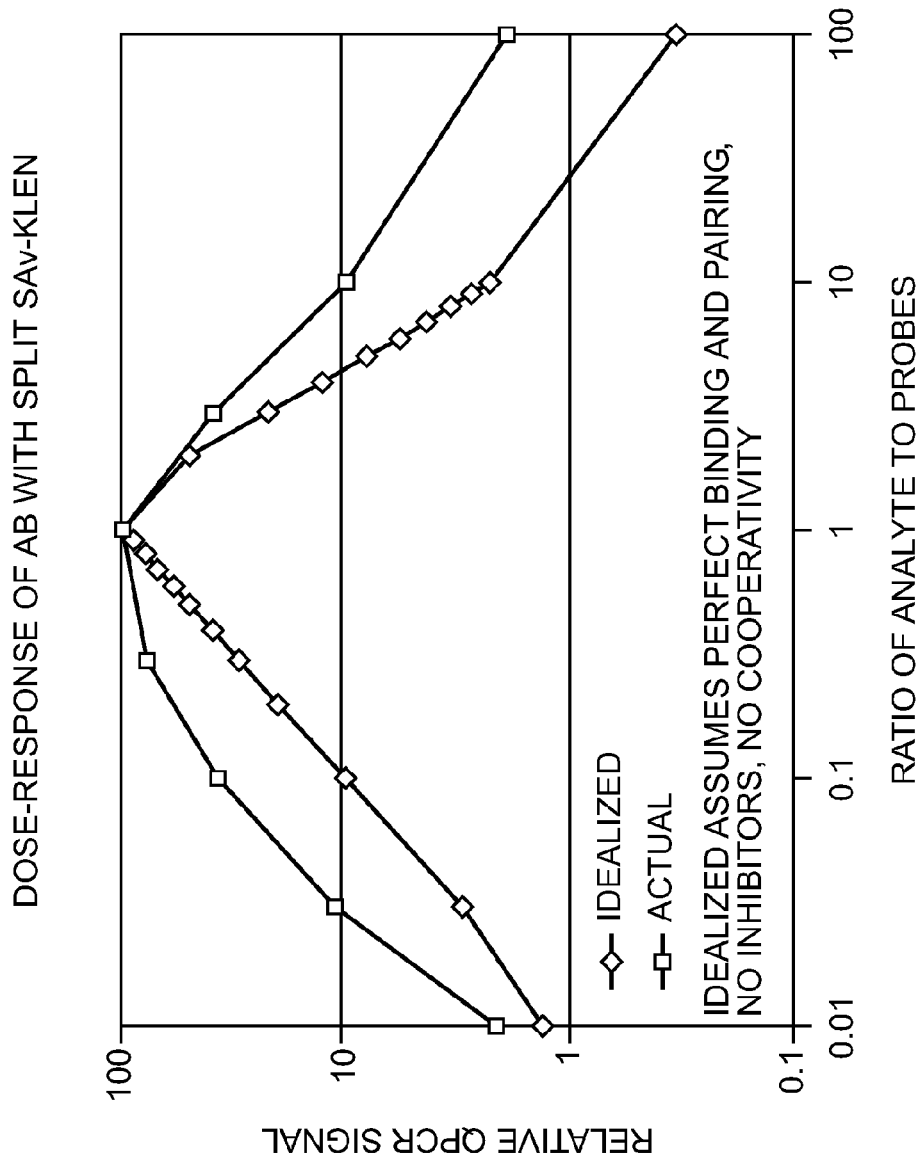
FIG. 9 depicts a dose response curve of varying concentrations of antibody in the presence of a constant amount of the N2 and C2 fragments of Klenow.

QPCR data is shown in FIG. 9. The x-axis show the ratio of analyte (biotin)-to-Klenow and the y-axis shows the 'Relative QPCR Signal'. As expected, the signal from binary binding rises as more analyte (biotinylated Ab) is added until it reaches a maximum at an approximate 1:10 ratio of biotin-to-Klenow. Further addition of analyte past the equimolar ratio reduces the number of analytes that become bound by both halves simultaneously and the signal drops.

Example 6

Construction of Long Neck Fusion Proteins

This example describes the construction of fusion proteins comprising streptavidin ("SAv") and a Klenow moiety (mature enzyme or N-terminal or C-terminal portion thereof), in which the streptavidin moiety and Klenow moiety are separated by a spacer region. These constructs are also referred to herein as Long Neck fusion proteins.

A DNA fragment encoding a mature streptavidin is obtained by PCR using *Streptomyces avidinii* DNA as a template and a pair of primers SF1 and SR:

```
SF1
GATCCGACCCCTCCAAGGACT                (SEQ ID NO: 7)

SR1
GCGCAGATCTCGAGCTGCTGAACGGCGTCGA      (SEQ ID NO: 8)
```

The PCR fragment obtained has a unique BsaI site shortly downstream of the SF1 primer sequence and unique XhoI and BglII sites encoded in the SR1 primer. The PCR fragment is cleaved at the BsaI restriction endonuclease site situated at the beginning of the nucleotide sequence encoding mature streptavidin. A double-stranded linker having the following sequence is ligated to the BsaI site:

```
                                           (SEQ ID NO: 9)
         5'-CATGGGCAGCAGCCATCATCATCATCATCAC-3'

(SEQ ID NO: 10)
         3'-CCGTCGTCGGTAGTAGTAGTAGTAGTGCGGC-3'
```

The linker encodes a polyhistidine tag and contains a NcoI sticky end on the one end and a 5'-CGGC sticky end on another end. The latter is compatible with the sticky end 5'-GCCG that was generated after cleaving the PCR fragment with BsaI. The linker is phosphorylated at the 5' protruding ends using T4 polynucleotide kinase (New England Biolabs, Beverly, Mass.), and connected to the PCR fragment at its BsaI-generated sticky end using T4 DNA ligase (New England Biolabs, Beverly, Mass.). About 10-100 times excess of the linker over the PCR fragment is recommended to ensure that majority of the PCR fragment has the linker attached. The ligation products are cleaved with NcoI and BglII restriction endonucleases, the linker-PCR fragment is separated from the linker in a 1.5% agarose gel, and the linker-PCR fragment ligation product is purified from the agarose gel, for example using QIAEX II kit (QIAGEN Sciences, Germantown, Md.) according to the manufacturer's instructions.

The purified DNA fragment is ligated into a pET-15b vector cleaved with NcoI and BamI restriction endonucleases. The ligation products are transformed into XL10 Gold competent cells (Stratagene, La Jolla, Calif.) and seeded on agar plates containing 100 µg/ml ampicillin. The ampicillin-resistant colonies emerge after incubating the plates at 37° C. overnight. The plasmid DNA is extracted by boiling a material from a colony in 1 ml of water for 3 minutes, and the released plasmids are analyzed for the presence of the insert in PCR using SF1 and SR1 primers. The insert-positive colonies are grown overnight in liquid medium, such as L-broth supplemented with 100 µg/ml ampicillin, and the plasmid DNAs are purified using STRATAPREP® Plasmid miniprep kit (Stratagene, La Jolla, Calif.). The DNA sequence of the obtained plasmids is verified by Sanger method using T7 promoter primer 5'-TAATACGACTCACTATAGG-3' (SEQ ID NO:11) that is complementary to the T7 promoter DNA sequence upstream of the insert.

The resulting pET-SAV plasmid encodes His-tagged streptavidin under the control of a T7 promoter. A unique XhoI site encoded in the SR1 primer is introduced at the end of streptavidin open reading frame to facilitate the cloning of DNA sequences encoding a spacer and a polymerase into the pET-SAV plasmid.

A synthetic flexible spacer region that is rich with small amino acids, such as glycine, serine, alanine, and threonine, is introduced into the plasmid. The following double-stranded oligonucleotide "GS" that encodes small amino acids glycine and serine is synthesized:

```
                                       (SEQ ID NO: 12)
5'-TCGACGGATCGGGCGGTGGCTCCGGTGGCGGCAGCGGCC-3'

(SEQ ID NO: 13)
3'-GCCTAGCCCGCCACCGAGGCCACCGCCGTCGCCGGAGCT-5'
```

The pET-SAV plasmid is cleaved with XhoI endonuclease at the end of the nucleotide sequence encoding the streptavidin open reading frame and the GS oligonucleotide, flanked by XhoI sticky ends (5'-TCGA), is ligated into that site. The resulting clones are sequenced using the T7 promoter primer, and the clones having the GS oligonucleotide in the correct orientation (in-fusion with SAv open reading frame) are selected for further work. A selected clone was designated pET-SAV-GS. This clone has a unique XhoI site at the end of the GS sequence since the XhoI sticky end at the beginning of the GS does not result in a complete XhoI site when ligated into the plasmid. The unique XhoI site can be used to add further moieties downstream of SAv-GS fusion gene. This approach, i.e. inserting polynucleotide sequences that result in unique XhoI site at the end of the inserted sequence, permits the repeated addition of other polynucleotide sequences encoding moieties of interest.

Instead of or in addition to the GS spacer oligonucleotide, a naturally occurring flexible unstructured region can be used. Such regions can be selected from abundantly expressed proteins, for example from L7/L12 ribosomal protein (Bocharov et al., "From structure and dynamics of protein L7/L12 to molecular switching in ribosome," J. Biol. Chem., 2004 279 (17):17697-706).

A PCR fragment encoding a flexible unstructured region of the protein is obtained using E. coli K12 DNA as a template and L73F and L71R pair of primers:

```
L73F
GCGCGTCGACGAAGAAAAATTCGGTGTTTCC   (SEQ ID NO: 14)

L71R
GCGCCTCGAGCTTTTCTTCAGCAGCTTCAACC  (SEQ ID NO: 15)
```

The L73F primer encodes a SalI restriction site and the L71R primer encodes an XhoI restriction endonuclease site. The resulting L7 PCR fragment has a SalI site at the beginning and an XhoI site at the end of the partial L7/L12 open reading frame that is encoded in the fragment. The fragment is cleaved with XhoI and SalI restriction endonucleases and ligated into a pET-SAV-GS plasmid cleaved with XhoI. The plasmids with the correct orientation of the insert are selected using DNA sequencing as above. The resulting plasmid is designated pET-SAV-GS-L. Several tandem copies of L7 fragment can be inserted into the spacer region using this approach. The resulting plasmids with 2, 3, 4, 5, 6, 7, or 8 L7 copies were designated pET-SAV-GS-Lx2, pET-SAV-GS-Lx3, pET-SAV-GS-Lx4, pET-SAV-GS-Lx5, pET-SAV-GS-Lx6, pET-SAV-GS-Lx7, and pET-SAV-GS-Lx8. The obtained plasmids with one or more L7 inserts have a unique XhoI site at the end of the SAV-GS-L7x(n) open reading frame. This unique XhoI site is used to add a Klenow moiety downstream of the fusion gene. Collectively, these plasmids are referred to as pET-SAV-GS-Lx(n), where n is a number of tandem copies of the L7 fragment.

The Klenow fragment of DNA polymerase I is cloned at the end of the above-described fusion genes. A PCR fragment encoding the Klenow fragment of DNA polymerase I was generated using E. coli DNA as a template and the following pair of primers:

```
KlinF
                                              (SEQ ID NO: 16)
GCGCGTCGACGGTGGCGGTGGCTCGGTGATTTCTTATGACAACTACGTC
A-3'

KWR
                                              (SEQ ID NO: 17)
5'-GCGCAAGCTTAGTGCGCCTGATCCCAGTTTTC-3'
```

The resulting PCR fragment is designated KL and encodes the entire Klenow open reading frame preceded by several codons encoding glycines and serines that were designed in the KlinF primer to provide additional spacer distance. The fragment is cut at both ends at the SalI and HindIII sites provided in the primers and cloned into any of the above-described plasmids following the spacer sequence. The resulting plasmids are designated pET-SAV-GS-KL and pET-SAV-GS-Lx(n)-KL.

In addition, PCR fragments encoding N-terminal or C-terminal portions of Klenow are cloned into one of the above-described SAv-spacer fusion constructs. A PCR fragment encoding an N-terminal portion of Klenow is obtained using KlinF primer and the following reverse primer SN2R:

```
                                              (SEQ ID NO: 18)
SN2R  5'-GCGCAAGCTTAATCGATCTTCACACCGTTAC-3'
```

The obtained PCR fragment is designated N2.

A PCR fragment encoding a C-terminal portion of Klenow is obtained using reverse primer KWR and the following forward primer SC2F:

```
                                              (SEQ ID NO: 19)
SC2F  5'-GCGCGTCGACGGTGGCAGCGATCCGAAAGTCCTGCACAA-3'
```

The obtained PCR fragment is designated C2.

N2 and C2 fragments are cleaved with SalI and HindIII restriction endonucleases and cloned into XhoI and HindIII digested plasmids that encode an SAv-spacer fusion protein. The resulting plasmids are designated pET-SAV-GS-Lx(n)-

N2 and pET-SAV-GS-Lx(n)-C2, where n is a number of tandem copies of the L7 fragment.

An affinity purification tag can also be added at the end of the fusion genes. The C-terminal tag provides for tandem affinity purification (TAP) in combination with the His-tag that was introduced at the N-terminus of streptavidin. There are many tags known to one of skill in the art that can be used for TAP, including those that are based on 1) binding to their natural or modified small ligand or a protein binding partner, or 2) binding to immobilized tag-specific antibodies. By way of example, FLAG, His, CBP, CYD (covalent yet dissociable NorpD peptide), Strep II, HPC (heavy chain of protein C) peptide tags, and the GST and MBP can be combined for TAP.

To provide a FLAG tag on the C-terminus of the Klenow moiety, the following double-stranded oligonucleotide F encoding two FLAG tags followed by a stop codon is synthesized:

```
                                            (SEQ ID NO: 20)
5'-ACTAGTGATTATAAGGATGACGATGACAAAGATTACAAAGATGATGA
CGATAAGTAG-3'

(SEQ ID NO: 21)
5'-CACTAATATTCCTACTGCTACTGTTTCTAATGTTTCTACTACTGCTA
TTCATCTTAA-5'
```

Oligonucleotides encoding less than two or more than two FLAG tags can also be used. To remove a stop codon at the end of the Klenow open reading frame, the Klenow DNA template is amplified with the following pair of primers:

```
XhoF
CGTGCACTCGAGTTGCTAAA                 (SEQ ID NO: 22)

SpR
GCGCACTAGTATGCGCCTGATCCCAGTTTTC      (SEQ ID NO: 23)
```

The PCR fragment thus obtained has a unique internal XhoI site that resides in the Klenow polynucleotide sequence and a unique SpeI site that was introduced at the end of the Klenow open reading frame before the stop codon using the SpR primer. The fragment is cleaved with XhoI and ligated into any of the pET-SAV-GS-KL, pET-SAV-GS-Lx(n)-KL, pET-SAV-GS-Lx(n)-C2 and pET-SAV-GS-Lx(n)-N2 plasmids cleaved with XhoI at the same internal site. Next, T4 DNA ligase is inactivated by incubation at 65° C. for 20 minutes. The ligation products are cleaved with SpeI and EcoRI restriction endonucleases according to the manufacturer's instructions, separated in 1% agarose gel, and the largest DNA fragment, containing the entire pET-15b DNA sequence between the NcoI and EcoRI sites and a fusion gene connected at the NcoI site to the plasmid, including the Klenow gene up to the SpeI site at the end of it was purified, for example using QIAEX II kit (QIAGEN Sciences, Germantown, Md.) according to the manufacturer's instructions.

Oligonucleotide F that is flanked by SpeI and EcoRI sticky ends is ligated with the purified fragment having the same sticky ends. The ligation products are transformed into XL10 Gold competent cells (Stratagene, La Jolla, Calif.) and seeded on the agar plates containing 100 µg/ml ampicillin. The ampicillin-resistant colonies emerge after incubating the plates at 37° C. overnight. The plasmid DNA is extracted by boiling material from a colony in 1 ml of water for 3 minutes, and the released plasmids are analyzed for the presence of the insert in PCR using XhoF and FR (CTACTTGTCATCGTCATC-CTTAT) (SEQ ID NO:24) primers.

The insert-positive colonies are grown overnight on liquid medium, such as L-broth supplemented with 100 µg/ml ampicillin, and the plasmid DNAs are purified using STRATAP-REP® Plasmid miniprep kit (Stratagene, La Jolla, Calif.). The presence of double FLAG tag at the end of the fusion genes is verified by the Sanger method using MfeF (CGGCA-GAAGTGTTTGGTTTG) (SEQ ID NO:25) primer.

Example 7

Production and Purification of Long Neck Fusion Proteins

E. coli strains harboring any of the plasmids encoding the SAv-polymerase fusion proteins described in Example 6 can be used to produce the SAv-spacer-Klenow fusion proteins encoded by the plasmids. Routinely, E. coli BL21 DE3 strain (Stratagene, La Jolla, Calif.) is used, however any E. coli strains that express T7 RNA polymerase are suitable for this purpose since the expression of the fusion proteins is driven by a T7 promoter residing in the pET-15b vector. Of course, one of skill in the art would recognize that other vectors and other promoters, for example tac promoter, can be used to produce these fusion proteins. Cultivation of recombinant E. coli for expression of proteins under control of T7 promoter is performed essentially as disclosed in U.S. Pat. No. 4,952,496 (Studier). The cells are harvested by centrifugation at 5,000 rpm for 15 min at 4° C. in JA-10 rotor using J2-21 centrifuge (Beckman Coulter, Fullerton, Calif.). The cells from 250 ml culture are resuspended in 10 ml of buffer A (50 mM Tris-HCl, pH 8, 150 mM NaCl, 5 mM ditiothreitol) supplemented with 1% triton X-100 and a set of protease inhibitors Complete (Roche Diagnostics GmbH, Mannheim, Germany), and disrupted by constant sonication for 1.5 min using Sonifier 250 at output 3 setting (Branson Ultrasonics Corporation, Danbury, Conn.).

The disrupted cells are centrifuged at 20,000 rpm for 15 min at 4° C. in JA-20 rotor using J2-21 centrifuge (Beckman Coulter, Fullerton, Calif.). Streptavidin fusion proteins form inclusion bodies and are found predominately in the pellet. However, significant amounts of soluble proteins could be recovered, especially if streptavidin and an enzyme are separated by long flexible unstructured regions. Nevertheless, purification from the insoluble fraction is preferred since the pellet is enriched in the fusion proteins as compared to supernatants, the fusion proteins in the pellet are less prone to protein degradation, and most importantly, they need to be denatured anyway to remove endogenous biotin. The pellet is resuspended in 10 ml of buffer A by sonication as described above, diluted in buffer A to 40 ml and centrifuged again at 20,000 rpm for 15 min at 4° C. in JA-20 rotor on J2-21 centrifuge.

The pellet is resuspended in 7.5 ml of buffer A and a 300 µl aliquot of the resuspension is used to purify the fusion proteins. The rest of the resuspended pellet is stored at −80° C. for future use. The 300 µl aliquot of the resuspended inclusion bodies is centrifuged for 15 minutes at 14,000 rpm/min, the supernatant is discarded and the pellet is resuspended in 2.8 ml of 6M GdHCl pH 1.5 and transferred into two 1.5 ml tubes. The tubes are rotated at 4° C. for 1 h and then centrifuged for 15 min at 14,000 rpm/min.

The supernatant is collected and dialyzed against 300 ml of 6M GdHCl pH 1.5 for overnight at room temperature in order to remove endogenous biotin that was bound to the streptavidin moiety. Further dialysis steps are performed at 4° C.

Next, the sample is dialyzed against 300 ml of 6 M GdHCl, 0.5 M NaCl, 20 mM Na—P pH 7.4 for 4 hours, and then further dialyzed against three changes of the same volume of buffer B (20 mM sodium phosphate pH 8, 150 mM NaCl, 2 mM dithiothreitol) for at least 2 hours each change.

The sample is removed from the dialysis bag, centrifuged for 15 min at 14,000 rpm/min, and the supernatant is collected into 1.5 ml microtubes. Imidazole is added to the supernatant at a 10 mM concentration, after which 100 µl of the 50% slurry of Ni-NTA agarose beads (QIAGEN Sciences, Germantown, Md.) equilibrated in buffer B is added to each 1.4 ml of the supernatant.

The supernatant is rotated with the beads at 4° C. for 15 minutes, after which the beads are pelleted by centrifugation at 2,000 rpm/min for 2 minutes, washed thrice with 1.5 ml of the buffer B supplemented with 10 mM imidazole, pelleted as described above and the supernatant completely removed. The adsorbed fusion proteins are eluted with 250 mM imidazole in buffer B and dialyzed overnight against at least 100 volumes of buffer containing 30 mM sodium phosphate pH 7.2, 50 mM NaCl, 4 mm DTT, 50% glycerol. The purified fusion protein is stored at −20° C.

Example 8

Detection of Analyte Using Long Neck Fusion Proteins in Solid-Phase Assay

An ELISA was used to test the ability of the Long Neck fusion proteins to detect the presence of biotinylated anti-GST antibody binding to GST in a solid-phase detection reaction. The adsorption, blocking, washing, and incubation steps were all standard for a typical ELISA. After addition of the biotinylated anti-GST detection antibody, a streptavidin-spacer-Klenow protein of Example 6 is added.

First, the fusion protein is diluted to 100 ng/ml in Blocking/dilution buffer containing 0.2% fish skin gelatin, 2% heat inactivated normal goat serum, 10 mM Tris-HCl pH 8.0, 200 mM NaCl, 0.02% Tween-20. The diluted fusion protein is added to the ELISA plate at 75 µl/well and incubated for 30 minutes at room temperature to allow the SAv moiety to bind to the biotinylated antibody. Then the solution is aspirated from the wells and the wells were washed 4 times with 400 µl of TBST buffer (25 mM Tris-HCl pH 8.0, 125 mM NaCl, 0.1% Tween-20), followed by 2 washes with deionized water.

A Klenow extension mixture is then added to the wells to facilitate formation of an unmodified copy of the modified polynucleotide template.

Klenow Extension Mixture (all Concentrations are Final after Mixing):
10 mM Tris-HCl (pH 7.5)
5 mM MgCl$_2$
7.5 mM DTT
500 µM dNTPs (ACGT)
100 µg/ml BSA
100 nM Alien1-Reverse primer
40 pM Oligo1 (modified oligonucleotide template)

Oligo1 has the following sequence, where 2'OMe indicates a 2'-O-methoxy modified nucleotide and U indicates 2'-deoxyuridine:

```
                                      (SEQ ID NO: 4)
5'-TTTTTTTGCTCGACGGTGAAUGAUGTAGGUACCAGC AGUAACUCGA

GCACGUCUU 2'OMe(CG)A 2'OMe(CC) AAATCUGGAUAUUGCAGCC

TCGT-3'.
```

The Alien1-Rev primer anneals to the 3' end of Oligo1 to prime the Klenow reaction and has the following sequence:

```
5'-ACGAGGCTGCAATATCCAGA-3'    (SEQ ID NO: 5)
```

The reaction is allowed to proceed for 0.5-16 hours at room temperature. During the reaction, Klenow polymerase produces a copy of the Oligo1 template that has no 2'-Me or 2'-deoxyuridine modifications.

Next, a 2×QPCR Master Mix is added to the wells to provide for the following concentrations of the components of PCR reaction:
15 mM Tris-HCl pH 8.4
50 mM KCl
2.5 mM MgCl$_2$
3% DMSO
0.01% Tween-20
800 µM dNTPs (ACGT)
0.444×SYBR® (Molecular Probes, Eugene, Oreg.) Green (provided as 10,000×)
30 nM Rox reference dye (Stratagene Cat#600530)
Pfu(exo⁻) 50 U/ml (Stratagene Cat#600163-81)

```
100 nM Alien 1-Forward primer
(5'-TGCTCGACGGTGAATGATGT-3')     (SEQ ID NO: 6)

100 nM Alien 1-Reverse primer
(5'-ACGAGGCTGCAATATCCAGA-3')     (SEQ ID NO: 5)
```

After mixing the samples, they are run in an MX3005P using the program for SYBR® green with dissociation curve and 2-step cycling parameters of 95° C. for 10 minutes (1 cycle), 95° C. for 15 seconds, 63° C. for 30 seconds (40 cycles). The relative QPCR signal is computed by calculating the change in Ct between the Ct at analyte concentration=0 pg/ml and the Ct at analyte concentration=X pg/ml. This is called the "dCt from 0." In a 100% efficient assay, a change of one Ct is equivalent to a doubling of the amount of initial usable QPCR template. To convert this logarithmic signal into a linear quantity the following formula "Relative QPCR Signal"=2^(dCt from 0)−1 is used. Finally, relative QPCR Signal is plotted against the concentration of analyte (pg/ml) used in a sample.

Figure 10:
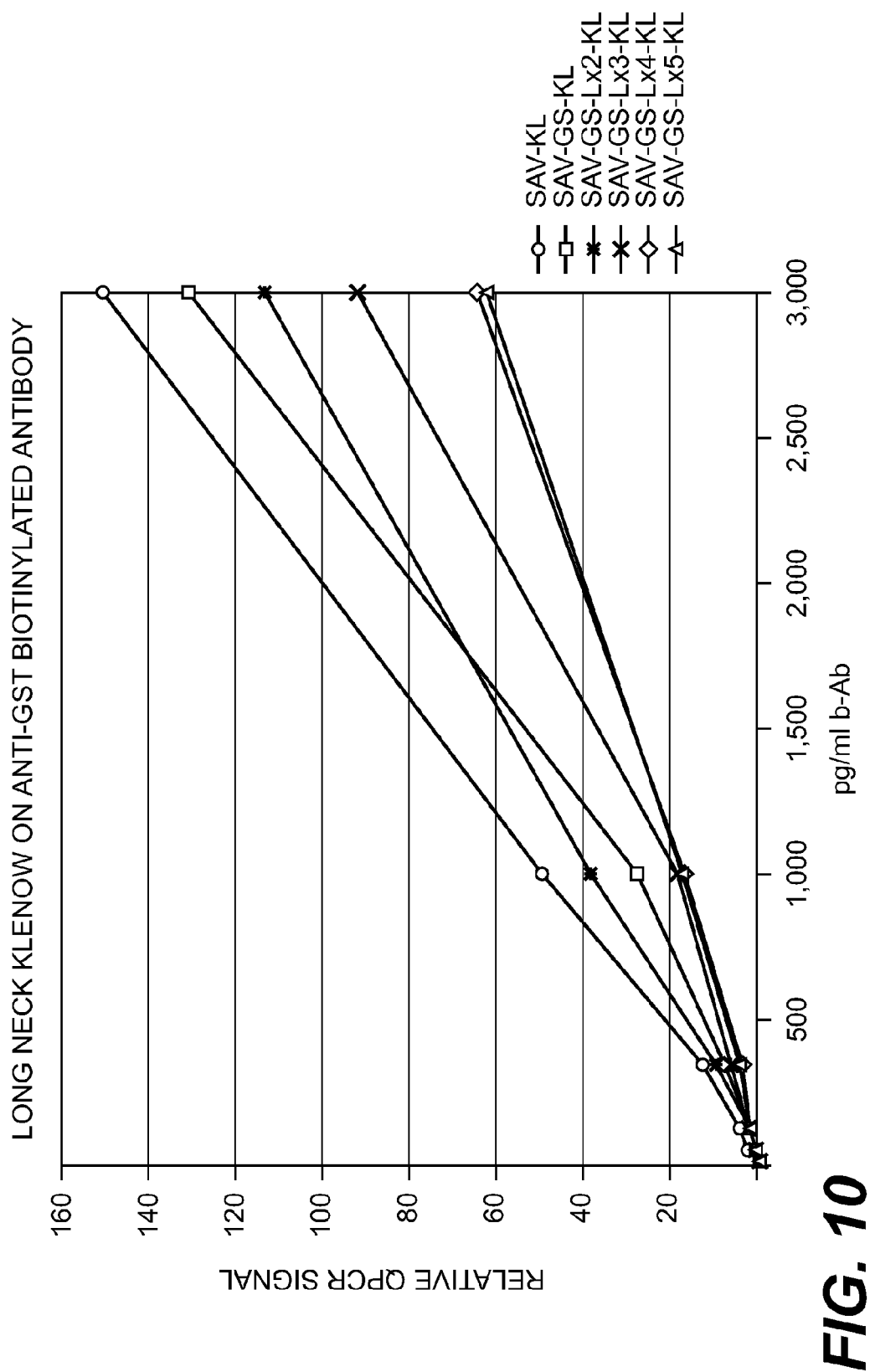
FIGS. 10 and 11 depict the results of a solid phase detection reaction using various Long Neck fusion proteins comprising a streptavidin moiety, different polypeptide linkers, and a Klenow moiety to detect the presence of biotinylated anti-GST antibody binding to GST.
Figure 11:
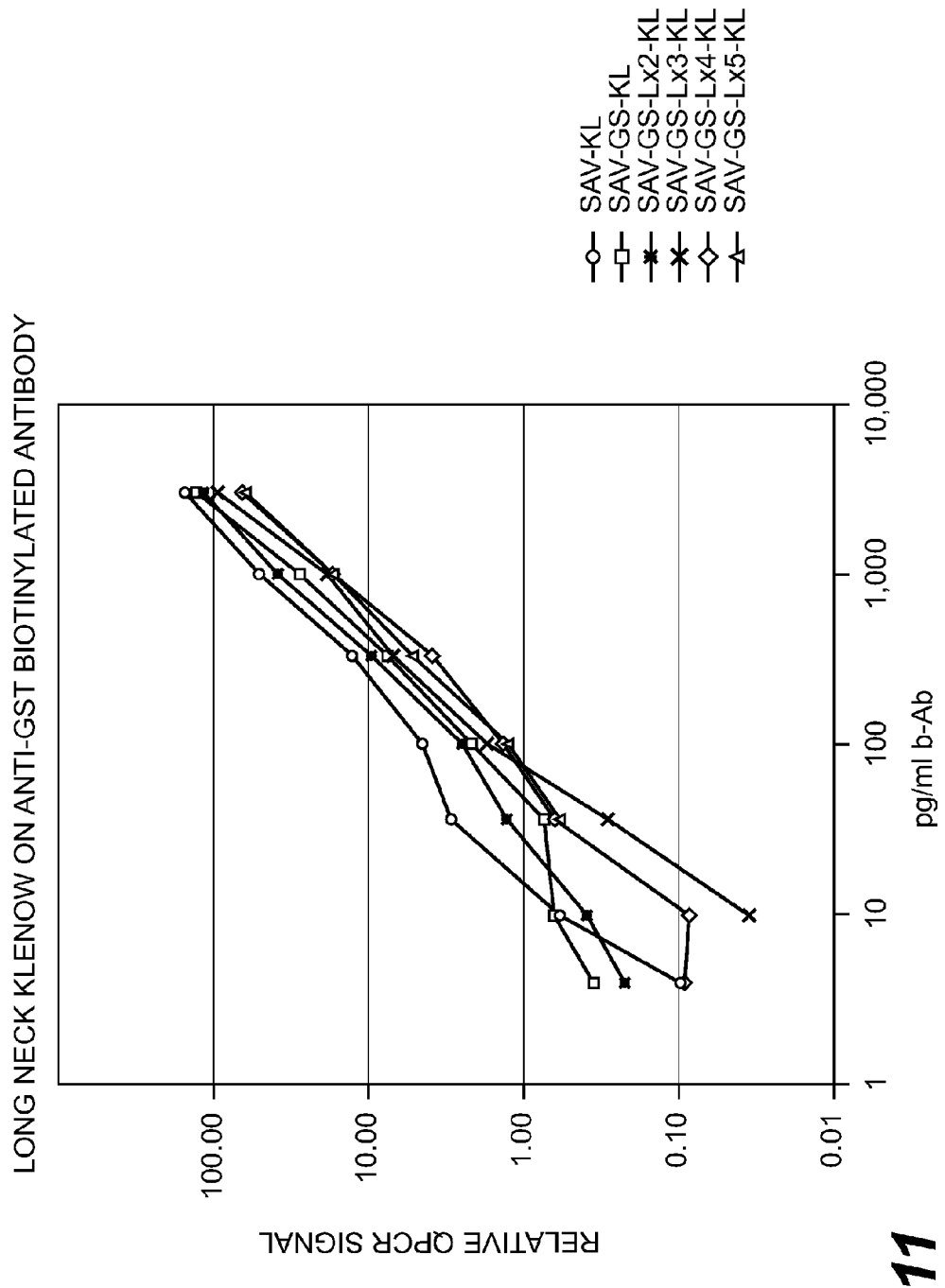

Several versions of the SAv-spacer-Klenow fusion proteins were tested for activity in this assay, including SAv-KL, SAv-KL, SAv-GS-Lx2-KL, SAv-GS-Lx3-KL, SAv-GS-Lx4-KL, and SAv-GS-Lx5-KL. FIGS. 10 and 11 show the results of this assay. All fusion proteins were active and all were useful in measuring the titration of the analyte (biotinylated anti-GST antibody). As shown in FIGS. 10 and 11, adding a spacer region to these fusion protein constructs generally enhanced the relative QPCR signal in this assay.

Example 9

Detection of Analyte Using Long Neck Fusion Proteins in Solution-Based Assay

Figure 12:
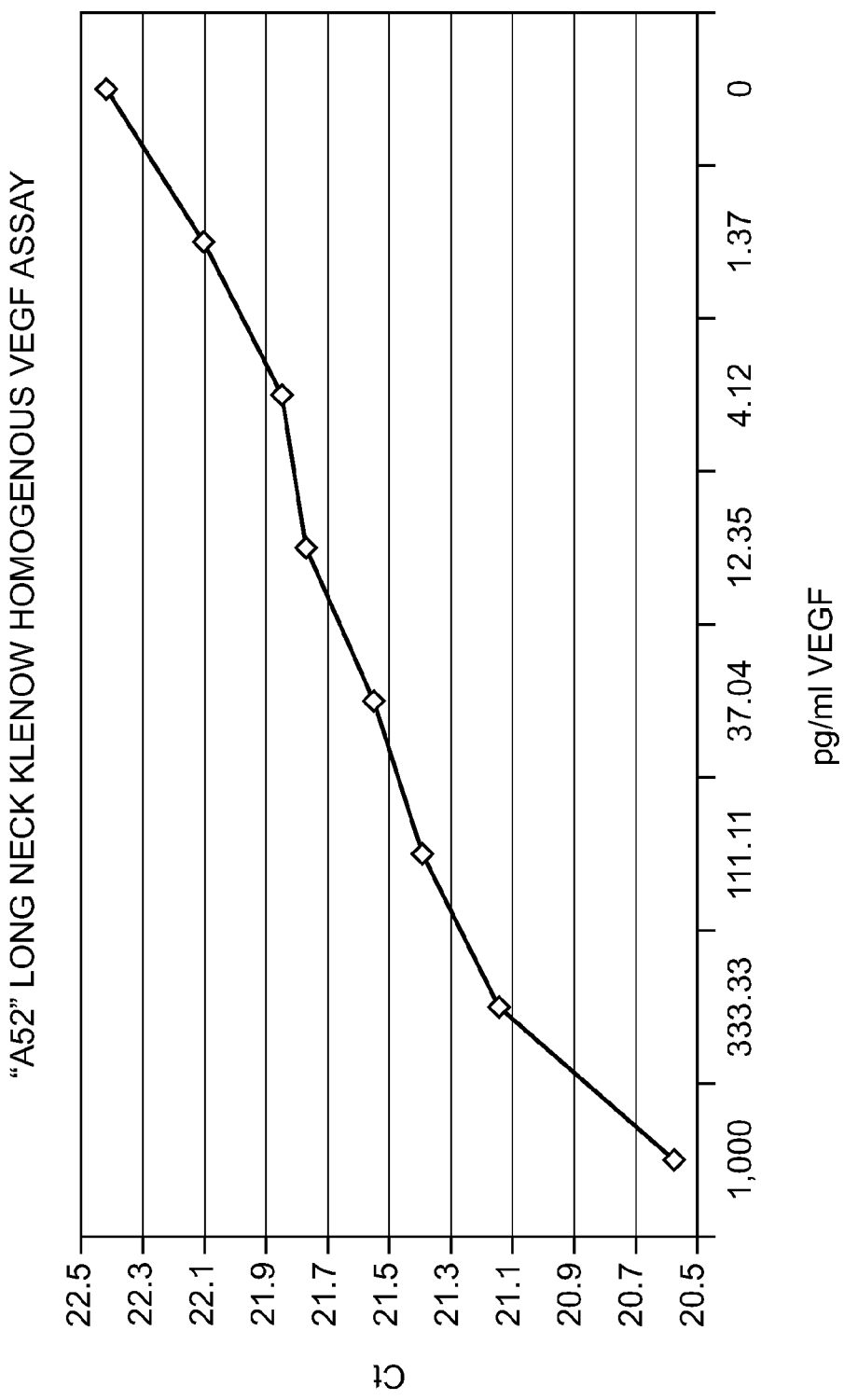
FIG. 12 depicts the results of a solution-based (homogenous) detection reaction using a Long Neck fusion protein comprising a streptavidin moiety, a polypeptide linker, and a Klenow moiety (SAv-GS-Lx4-KL) to detect the presence of biotinylated anti-VEGF antibody binding to VEGF.

A polyclonal biotinylated anti VEGF antibody was split into two pools. One pool was labeled with the SAv-GS-Lx4-KL fusion protein of Example 6. The other pool was labeled with streptavidin that had been chemically coupled to a modified polynucleotide template containing dUTP and 2'-O-methoxy modified nucleotides. The labeling reactions were quenched by the addition of 1 mM D-biotin. A 100 pM solution of the probes combined in equal parts was prepared and 4 μl was dispensed to QPCR reaction tubes. One microliter each of a 3-fold dilution series of recombinant human VEGF was added to the 4 μl of probe mixture and incubated at room temperature for 1 hour. Forty five microliters of Klenow extension buffer was then added to each sample and incubated for 10 minutes at 37° C. The Klenow was then heat killed for 20 minutes at 75° C. Five microliters of the heat killed extension reaction was transferred to a new tube containing a SYBR® (Molecular Probes, Eugene, Oreg.) green QPCR master mix containing Pfu (exo⁻) polymerase and then analyzed by QPCR. The results are shown in FIG. 12, indicating that the QPCR signal was proportional to the amount of VEGF analyte added to each reaction.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. A composition comprising:
   a modified polynucleotide template having one or more modified nucleotides and a 3' terminal nucleotide;
   a binding molecule coupled to a first polymerase which amplifies the modified polynucleotide template; and
   a second polymerase uncapable of amplifying the modified polynucleotide template but capable of amplifying an unmodified copy of the modified polynucleotide template.

2. The composition of claim 1, wherein the 3' terminal nucleotide of the modified polynucleotide template is not a modified nucleotide.

3. The composition of claim 1, wherein the binding molecule is an antibody and the first polymerase is a Klenow or T4 polymerase.

4. The composition of claim 1, wherein the modified polynucleotide template comprises one or more deoxyuracils and/or 2'O-methyl modifications.

5. The composition of claim 3, wherein the antibody is linked to the first polymerase by a biotin-streptavidin interaction.

6. The composition of claim 3, wherein the antibody is biotinylated and the first polymerase is linked to streptavidin or avidin.

7. The composition of claim 1, wherein the modified polynucleotide template is not coupled to the binding molecule.

8. A method for detecting an analyte in a sample, the method comprising:
   a) contacting a sample with the composition of claim 1, wherein the binding molecule is capable of binding to the analyte, so as to permit:
      binding of the binding molecule to the analyte,
      annealing of a first primer to the modified polynucleotide template, and
      extending of the primer with the first polymerase thereby synthesizing a copy of the modified polynucleotide template,
      wherein the copy does not have any of the one or more modified nucleotides ("unmodified copy"); and
   b) amplifying the unmodified copy with the second polymerase; and
   c) detecting the amplified unmodified copy, wherein detection of the amplified unmodified copy is indicative of the presence or amount of the analyte in a sample.

9. The method of claim 8, wherein the binding molecule is an antibody.

10. The method of claim 8, wherein the first polymerase is Klenow or T4.

11. The method of claim 9, wherein the antibody is coupled to the first polymerase by a biotin-streptavidin interaction.

12. The method of claim 11, wherein the antibody is biotinylated and the first polymerase is coupled to streptavidin or avidin.

13. The method of claim 8, wherein the modified polynucleotide template comprises one or more deoxyuracils and/or one or more 2' O-methyl modifications.

14. The method of claim 8, wherein the second polymerase is a thermostable polymerase.

15. The method of claim 14, wherein the thermostable polymerase is a Pfu or a Taq polymerase.

16. The method of claim 12, wherein a polypeptide linker couples the streptavidin or avidin and the first polymerase.

* * * * *

UNITED STATES PATENT AND TRADEMARK OFFICE
CERTIFICATE OF CORRECTION

PATENT NO. : 9,291,627 B2
APPLICATION NO. : 12/375570
DATED : March 22, 2016
INVENTOR(S) : Alexander Belyaev et al.

It is certified that error appears in the above-identified patent and that said Letters Patent is hereby corrected as shown below:

On The Title Page

On page 2, in column 1, under "Other Publications", line 24, delete "S01;it" and insert -- Split --, therefor.

In The Specification

In column 8, line 19, delete "nonspecific" and insert -- non-specific --, therefor.

In column 9, line 1, delete "Polymerase" and insert -- polymerase --, therefor.

In column 10, line 5, delete "Bacteoriol," and insert -- Bacteriol, --, therefor.

In column 12, line 34, delete "Archaeglobus" and insert -- Archaeoglobus --, therefor.

In column 16, line 40, delete "analyte," and insert -- analyte. --, therefor.

In column 18, line 6, delete "know" and insert -- known --, therefor.

In column 24-25, line 67 (column 24), line 1 (column 25), delete "Thermatoga martima" and insert -- Thermotoga maritima --, therefor.

In column 29, line 12, delete "know" and insert -- known --, therefor.

In column 30, line 27, delete "2'-β-methyl." and insert -- 2'-O-methyl." --, therefor.

In column 31, line 55, delete "multi-plea" and insert -- multi-plex --, therefor.

In column 31, line 66, delete "multi-plea" and insert -- multi-plex --, therefor.

In column 32, line 36, delete "mine" and insert -- amine --, therefor.

In column 32, line 44, delete "dent" and insert -- dNTP --, therefor.

In column 32, line 45, delete "Brioche.," and insert -- Biochem., --, therefor.

In column 36, line 25, delete "micro titer" and insert -- microtiter --, therefor.

In column 36, line 26-27, delete "micro titer" and insert -- microtiter --, therefor.

In column 36, line 65, delete "micro titer" and insert -- microtiter --, therefor.

In column 45, line 11, delete "Quialex," and insert -- Qualex, --, therefor.

Signed and Sealed this
Fourteenth Day of June, 2016

Michelle K. Lee
*Director of the United States Patent and Trademark Office*

CERTIFICATE OF CORRECTION (continued)
U.S. Pat. No. 9,291,627 B2

In column 45, line 35, delete "-3'" and insert -- -3 --, therefor.

In column 49, line 11, delete "H is," and insert -- His, --, therefor.

In The Claims

In column 69, line 19, in claim 4, delete "2'O-methyl" and insert -- 2'-O-methyl --, therefor.

In column 70, line 25, in claim 13, delete "2' O-methyl" and insert -- 2'-O-methyl --, therefor.